United States Patent
Suryanaraya et al.

(10) Patent No.: US 11,624,090 B2
(45) Date of Patent: Apr. 11, 2023

(54) MANIPULATING THE TRANSLATION OF DNA STRANDS ACROSS AND THROUGH NANOPORE SEQUENCING SYSTEMS USING RAMAN SIGNATURES TO IDENTIFY DNA BASES AND METHODS

(71) Applicant: ARMONICA TECHNOLOGIES, INC., Albuquerque, NM (US)

(72) Inventors: Anupama Suryanaraya, Albuquerque, NM (US); Olga Amosova, Albuquerque, NM (US); Yuliya Kuznetsova, Albuquerque, NM (US); Alexander Neumann, Albuquerque, NM (US); Xin Jin, Albuquerque, NM (US); Steven Roy Julien Brueck, Albuquerque, NM (US); Jeremy S. Edwards, Albuquerque, NM (US)

(73) Assignee: Armonica Technologies, Inc., Carlsbad, CA (US)

( * ) Notice: Subject to any disclaimer, the term of this patent is extended or adjusted under 35 U.S.C. 154(b) by 473 days.

(21) Appl. No.: 16/741,154

(22) Filed: Jan. 13, 2020

(65) Prior Publication Data
US 2020/0224263 A1 Jul. 16, 2020

Related U.S. Application Data

(60) Provisional application No. 62/793,079, filed on Jan. 16, 2019, provisional application No. 62/793,084, filed on Jan. 16, 2019.

(51) Int. Cl.
| | |
|---|---|
| C12Q 1/6869 | (2018.01) |
| G01N 27/447 | (2006.01) |
| G01N 21/65 | (2006.01) |
| B82Y 15/00 | (2011.01) |
| B82Y 5/00 | (2011.01) |

(52) U.S. Cl.
CPC .......... C12Q 1/6869 (2013.01); G01N 21/65 (2013.01); G01N 27/44791 (2013.01); B82Y 5/00 (2013.01); B82Y 15/00 (2013.01); C12Q 2565/619 (2013.01); C12Q 2565/632 (2013.01)

(58) Field of Classification Search
CPC .......... C12Q 1/6869; C12Q 2565/619; C12Q 2565/632; C12Q 2563/116; C12Q 2565/628; C12Q 2565/631; G01N 21/65; G01N 27/44791; G01N 21/658; G01N 2021/653; B82Y 5/00; B82Y 15/00; B82Y 30/00
See application file for complete search history.

(56) References Cited

U.S. PATENT DOCUMENTS

| | | |
|---|---|---|
| 9,927,397 B1 | 3/2018 | Brueck et al. |
| 10,060,904 B1 | 8/2018 | Brueck et al. |
| 2003/0187237 A1 | 10/2003 | Chan et al. |
| 2008/0032308 A1 | 2/2008 | Su et al. |
| 2008/0239307 A1 | 10/2008 | Talley et al. |
| 2011/0136676 A1 | 6/2011 | Greene |
| 2013/0164191 A1 | 6/2013 | Coursey |
| 2013/0260472 A1 | 10/2013 | Holt |
| 2014/0335269 A1 | 11/2014 | Bond et al. |
| 2017/0253910 A1 | 9/2017 | Brown et al. |
| 2019/0227050 A1 | 7/2019 | Brueck et al. |

OTHER PUBLICATIONS

Mendoza et al, Electrophoretic plasmonic nanopore biochip genome sequencer, 2019, Optics and Laser Technology, 109, 199-211 , publicly available on Aug. 10, 2018. (Year: 2019).*
Belkin et al., Plasmonic Nanopores for Trapping, Controlling Displacement, and Sequencing of DNA, ACS Nano, Nov. 24, 2015, 9(11):10598-10611.
International Search Report and Written Opinion issued in International Application No. PCT/US2020/013325, dated May 14, 2020, 17 pages.
Rand et al., Mapping DNA Methylation with High Throughput Nanopore Sequencing, Nat Methods, Feb. 20, 2017, 14(4):411-413.

\* cited by examiner

*Primary Examiner* — Narayan K Bhat
(74) *Attorney, Agent, or Firm* — Withers Bergman LLP; Thomas C. Meyers

(57) ABSTRACT

Nucleic acid sequencing methods and systems, the systems including nanochannel chip including: a nanochannel formed in an upper surface of the nanochannel chip and; a roof covering the nanochannel and comprising nanopores and a field enhancement structure; and a barrier disposed in the nanochannel. The method including: introducing a buffer solution including long-chain nucleic acids to the nanochannel chip; applying a voltage potential across the nanochannel chip to drive the nucleic acids through the nanochannel, towards the barrier, and to translocate the nucleic acids through nanopores adjacent to the barrier, such that bases of each of the nucleic acids pass through the field enhancement structure one base at a time and emerge onto an upper surface of the roof; detecting the Raman spectra of the bases of the nucleic acids as each base passes through the electromagnetic-field enhancement structure; and sequencing the nucleic acids based on the detected Raman spectra.

28 Claims, 25 Drawing Sheets

(Without BSA Treatment)

(BSA Treatment)

(Lipid Treatment)

A) t = 360 s  B) t = 610 s (a)

(b)

MANIPULATING THE TRANSLATION OF DNA STRANDS ACROSS AND THROUGH NANOPORE SEQUENCING SYSTEMS USING RAMAN SIGNATURES TO IDENTIFY DNA BASES AND METHODS

CROSS-REFERENCE TO RELATED APPLICATIONS

This application claims priority to, and the benefit of, U.S. Provisional Application No. 62/793,079, filed Jan. 16, 2019, and U.S. Provisional Application No. 62/793,084, filed Jan. 16, 2019, the contents of each of which are incorporated by reference herein in their entireties.

BACKGROUND

The rapid determination of the nucleotide sequence of single- and double-stranded DNA and RNA is a major goal of researchers seeking to obtain the sequence for the entire genome of an organism. The ability to determine the full sequence of nucleic acids in DNA or RNA has additional importance in identifying genetic mutations and polymorphisms.

The dominant technologies in use today rely on massive parallel "shotgun" sequencing of short (~200 bp) genomic fragments, created by breaking the original genome into pieces and then amplifying these pieces with a polymerase chain reaction (PCR) and reading them in a parallel process by either fluorescence or electrical means. Assembling these short reads into a genome-length sequence requires sophisticated software and, usually, a "reference" genome sequence. The three biggest problems of the current approach are: its inability to correctly piece together repeated regions; to associate segments with specific chromosomes; and de novo assembly without a reference genome.

SUMMARY

Various embodiments are disclosed that are directed to methods and systems for long read, label-free, nanopore-based long chain molecule sequencing with optical readout. In general, the disclosed embodiments describe a novel sequencing technology based on the integration of nanochannels to deliver single long-chain sample molecules through widely spaced (>wavelength), ~1-nm aperture "tortuous" nanopores that slow translocation sufficiently so as to provide massively parallel, single base resolution readout using optical techniques. A novel, self-directed assembly nanofabrication scheme using readily available colloidal nanoparticles may be used to form the nanopore arrays atop nanochannels, in which the long chain molecules spontaneously unfold. At the surface of the nanoparticle array, strongly localized electromagnetic fields in engineered plasmonic/polaritonic structures allow for single base resolution using optical techniques. Surface Enhanced Coherent Anti-Stokes Raman Spectroscopy (SECARS) is one such technique that has the advantage of not requiring labeling of the bases. Fluorescence techniques with labeled bases provide an alternative possibility.

According to various embodiments of the present disclosure, a method for sequencing nucleic acids is disclosed, comprising the operations of introducing a buffer solution comprising long-chain nucleic acids to a nanochannel chip. The nanochannel chip comprising: a nanochannel formed in an upper surface of the nanochannel chip and configured to receive the buffer solution; a roof covering the nanochannel and comprising nanopores and an electromagnetic-field enhancement structure configured to spatially localize incident electromagnetic fields to a spatial scale of about 1 $nm^3$; and a barrier disposed in the nanochannel. The method for sequencing nucleic acids further comprising the operations of applying a voltage potential across the nanochannel chip to drive the nucleic acids through the nanochannel in a first direction, towards the barrier, and to translocate the nucleic acids through nanopores adjacent to the barrier, such that bases of each of the nucleic acids pass the electromagnetic-field enhancement structure one base at a time and emerge onto an upper surface of the roof; detecting the Raman spectra of the bases of the nucleic acids as each base passes the electromagnetic-field enhancement structure; and sequencing the nucleic acids based on the detected Raman spectra.

According to various embodiments of the present disclosure, provided is a nanochannel chip comprising: a substrate; nanochannels formed on an upper surface of the substrate; wells disposed on the substrate and fluidly connected to opposing open ends of the nanochannels; a nanoparticle layer covering the nanochannels and comprising nanopores; pillars disposed on an upper surface of the nanoparticle layer; a cover disposed on the pillars, such that a gap is formed between the cover and the upper surface of the nanoparticle layer; and an adhesive layer disposed between the cover and the pillars.

According to various embodiments of the present disclosure, provided is a nanochannel chip comprising: a substrate; nanochannels formed on an upper surface of the substrate; wells disposed on the substrate and fluidly connected to opposing open ends of the nanochannels; a nanoparticle layer covering the nanochannels and comprising nanopores; an alignment layer disposed on the nanoparticle layer and comprising a porous crystalline material; and an electromagnetic-field enhancement layer disposed on the alignment layer and configured to spatially localize incident electromagnetic fields to a spatial scale of about 1 $nm^3$, wherein the alignment layer has a higher pore density and a smaller average pore size than the nanoparticle layer.

According to various embodiments of the present disclosure, provided is a sequencing system comprising: a nanochannel chip comprising: a substrate; nanochannels formed on an upper surface of the substrate; wells disposed on the substrate and fluidly connected to opposing open ends of the nanochannels; a nanoparticle layer covering the nanochannels and comprising nanopores; an alignment layer disposed on the nanoparticle layer and comprising a porous crystalline material; and an electromagnetic field layer disposed on the alignment layer and configured to spatially localize incident electromagnetic fields to a spatial scale of about 1 $nm^3$, wherein the alignment layer has a higher pore density and a smaller average pore size than the nanoparticle layer; a coherent light source configured to illuminate a linear region of the nanochannel chip; a spectrometer configured to separate light emitted from the linear region into Raman spectral components; an objective configured to focus light emitted from the linear region on an inlet of the spectrometer; a camera configured to generate image data using the Raman spectral components output from the spectrometer into image data; and a processor configured to sequence the nucleic acids based on the image data.

BRIEF DESCRIPTION OF THE DRAWINGS

FIG. 14A shows the image ~360 s after introduction of the ssDNA. FIG. 14B shows the same region 250 s later at a total time since introduction of 610 s.

FIGS. 23A-22C illustrate the impact of adding a large particle to one end of the ssDNA in the nanochannels. The particle dimension is small enough to fit through the nanochannels but too large to transit the tortuous nanopore, resulting in a tethered ssDNA strand that cannot completely translocate the nanopore. Application of an electric field can stretch/compress the ssDNA moving different bases into the electromagnetic hot spot.

FIG. 43B shows OliGreen-dyed λ-ssDNA generated from lambda exonuclease digestion of the λ-dsDNA in situ, and introduced through the porous roof of the chip and FIG. 43C shows a corresponding histogram (of the λ-ssDNA of FIG. 43B) illustrating a size distribution of the λ-ssDNA length relative to a number of measured molecules of a given size range.

DETAILED DESCRIPTION

Figure 1:
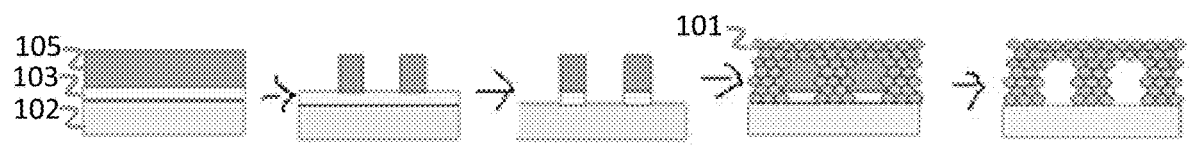
FIG. 1 is a schematic illustration of an exemplary method of nanochannel fabrication.

For complete sequence determination, the entire chromosome landscape must be decoded, including complex structural variants in the genome (i.e., aneuploidy (euploidy—extra sets of chromosomes; aneuploidy—missing/extra chromosomes; deviation from 46 chromosomes in human genome), translocations, inversions, duplications, loss of heterozygosity (dominant/recessive gene pairing)), etc. For example, balanced translocations (exchange of genetic information between non-homologous chromosomes) occur in approximately 1 in 500 individuals, trisomy 21, a specific instance of aneuploidy, occurs in as many as 1 in 650 live births, and extensive genome instability occurs in many cancers. Accordingly, complete genome sequencing ideally is able to identify all complex genome variants.

While the cost of genome sequencing has decreased dramatically, conventional technologies are still unable to completely sequence a human genome. There remain numerous regions of the human genome that are still unsequenced in the GRCh37 version of the genome, which consists of 249 scaffolds. Additionally, conventional technologies still require a reference genome for a high quality assembly. While de novo genome assemblies may be possible with short read technologies, the quality is low relative to resequencing projects. These problems limit the ability of next generation sequencing platforms to identify certain variants, such as large structural changes and repeated regions.

High throughput, long-read sequencing technologies will be essential for resolving the complexities of the human genome. The human genome is diploid, meaning that there are both maternal and paternal copies of 22 autosomes and two sex chromosomes (XX or XY), and a genome sequence is not complete unless all polymorphisms or variants are phased and assigned to specific chromosomes. Long read sequencing technologies will be essential to phase the genetic variants that are unique to each of the homologous chromosomes. Additionally, repetitive regions in the genome make complete sequencing impossible with short reads.

Recent advances in next generation sequencing technologies, along with the development of robust analytical methods, have given researchers the ability to determine the role of sequence variations in a variety of human diseases. However, the vast majority of these technologies produce results that are limited to finding polymorphisms while neglecting the importance of haplotypes. Today, the most commonly studied variations are single-nucleotide polymorphisms (SNPs) and small insertions and deletions (InDels). This is because conventional sequencing technologies, while proficient in identifying heterozygous loci, are unable to assign polymorphisms to one of the two homologous chromosomes, thus complicating the search for gene/disease associations. The HapMap and other projects are developing a haplotype (set of genes inherited from a single parent) map, but new technologies are required to address the cis and trans relationships in variants that occur in rare genotypes (e.g., novel somatic mutations) or in altered genomes (e.g., cancer). Without the context of knowing whether variants in intergenic regions are linked in cis and/or through long-range chromatin interactions to affected genes, it is not possible to predict whether such variants are detrimental. The principal advantage of haplotype resolved sequencing over standard whole genome sequencing (WGS) is that all polymorphisms are assigned to a specific chromosome (e.g., maternal vs. paternal), and links are established between mutations (or variants) in distant regulatory elements and cis-linked genes on the same chromosome.

The limitations associated with direct haplotype (set of maternal or paternal chromosomes) sequencing primarily revolve around the relatively short read-length and 'phase insensitivity' of the current platforms. There have been a few approaches to generate haplotype resolved sequences, but these are not consistent with the $1,000 genome goal, due to the complexity and additional cost associated with the processes upstream of sequencing. Thus, the various embodiments disclosed herein seek to provide long-read sequencing devices and methods that overcome the problems associated with conventional technologies.

As noted above, three significant problems of conventional genome "short-read" sequencing technologies are the inability to correctly piece together repeated regions; correct placement of segments within a haplotype; and de novo assembly without a reference genome. Long-read technologies (i.e., determining the sequence of long strands and/or fragments) are disclosed herein to overcome these difficulties. Various embodiments disclosed herein that passes a long single-stranded DNA (ssDNA) molecule through a small hole (a nanopore) with dimensions comparable to the size of the DNA (<1 nm diameter) and reads each base as it passes through the pore may be an attractive alternative to short read technologies. Such long, continuous reads offer the additional advantages of: single molecule measurements, reducing or eliminating the need for amplification; and high speed operation.

Nanopore-based long-read analysis methods may involve passing a ssDNA (or related molecules such as RNA), through a nanoscopic opening (i.e., a nanopore) while monitoring a signal to detect signatures of the various DNA components: adenine (A), cytosine (C), guanine (G), and thymine (T). A nanopore may be designed to have a size that allows the polymeric molecule to pass only in a sequential, single file order. As the polymeric molecule passes through the nanopore, various embodiment techniques may be used to obtain signature signals that allow for the identification of the various bases of a DNA molecule (i.e., sequence), most often nonspecific electrical measurements (e.g. current blockage or capacitance) have been reported.

Nanochannel Chip Fabrication

Figure 2:
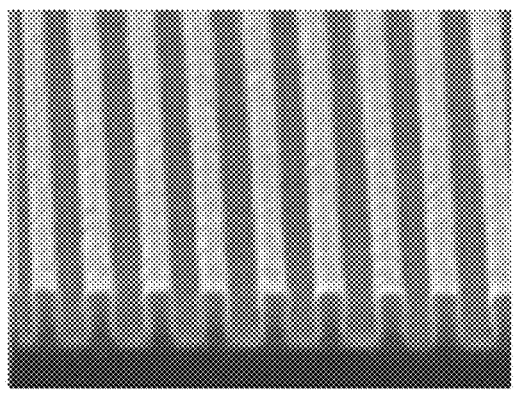
FIG. 2 is a scanning electron microscope (SEM) image showing a photoresist pattern for forming nanochannels having a 1 μm pitch.

FIG. 1 is a schematic illustration of an exemplary method of fabricating nanochannels of a nanochannel chip, according to various embodiments of the present disclosure. Referring to FIG. 1, it can be seen that in the depicted embodiment, nanochannel fabrication includes multiple steps. First, a substrate 102 (for example, quartz or fused silica) may be spin-coated with a bottom antireflection coating (ARC) 103 and then a photoresist layer 105. Next, lithography may be performed on the photoresist layer 103 to define the nanochannels with a spacing that is larger than the optical resolution of the readout system (see, e.g., FIG. 2). For example, a period of ~1 µm and a linewidth of 100- to 300-nm might be used. However, it will be appreciated that both smaller and larger periods and linewidths are readily available. According to the embodiment shown in FIG. 2, interferometric lithography may be used to form the nanochannels, and these dimensions are well within the capabilities of even one or two generation old lithographic tools, offering a ready extension to volume manufacturing. After exposure, the pattern is developed to provide a periodic array of lines and spaces where the photoresist (105) is present in the lines and has been removed in the spaces to expose the underlying ARC layer (103). Next, the antireflection layer 103 may be etched to expose the substrate 102. Alternatively, a developable ARC can be used wherein the parameters of the ARC are controlled such that the ARC layer is removed during the develop process to expose the substrate (102). Colloidal nanoparticles 101 (for example, silica nanoparticles) may then be spin-coated on the developed photoresist layer pattern 105, thus depositing them in a layer-by-layer fashion first in the spaces between the photoresist lines to form the nanochannel sidewalls and finally extending over the photoresist layer 103 to form the nanochannel roofs.

Figure 3:
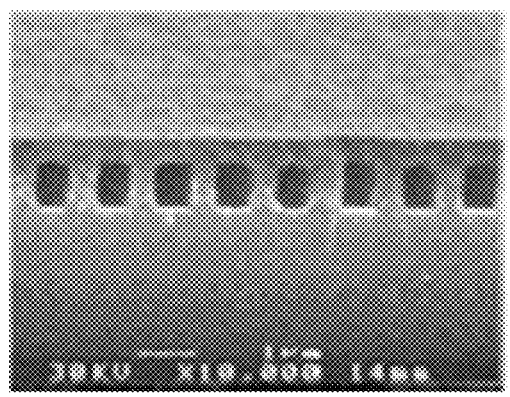
FIG. 3 is an SEM image showing 1D enclosed channels formed using the techniques described herein.
Figure 4:
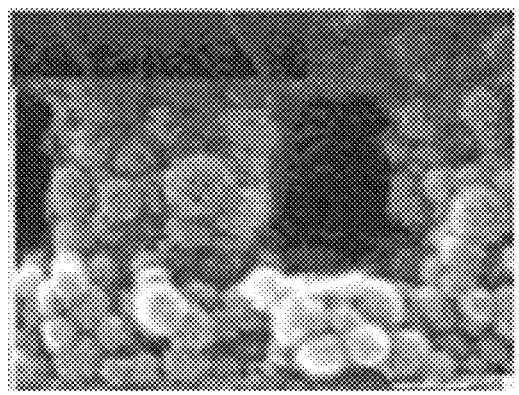
FIG. 4 is an SEM image of 500 nm wide channel walls formed by 50-nm diameter silica nanoparticles.
Figure 5:
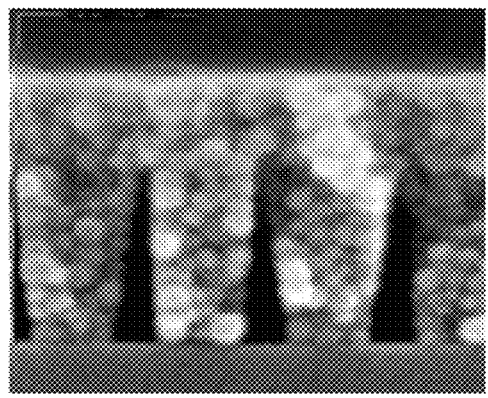
FIG. 5 is an SEM image of 100 nm wide channels formed using the techniques described herein.

As easily seen in the SEM images shown in FIGS. 3-5, the nanoparticles 101 may form both the sidewalls and the roofs of the nanochannels, with the nanoparticles in the roof stacking to form tortuous nanopores, which should a fluidic sample containing DNA molecules in a buffer solution be placed in the nanochannels, the DNA molecules would have to traverse the pores in order to reach the roof and vice versa. According to some embodiments, 50-nm-diameter silica nanoparticles may be used, but both the size and the material structure are flexible. Capillary forces during deposition may force the nanoparticles (NP) into a hexagonal close-packed geometry. As a rough estimate, this means that the spaces between nanoparticles are ~NP diameter/3 or ~17 nm. The pores may be complex, 3D paths, similar to the spacing and open paths created when oranges are piled up in the local supermarket. However, it should be understood that the actual structure may be highly complex due to the significant dispersion in nanoparticle sizes which is under the control of the nanochannel fabricator. For the purposes of the present disclosure, the spacing and open paths created by the nanoparticles may be referred to as "tortuous nanopores." In layer-by-layer deposition, steric effects due to the NP size dispersion may create a range of nanopore sizes.

After spin-coating of the nanoparticles, the structure may then be calcined (~800° C. in an air ambient) to remove the remaining hydrocarbon films (photoresist and ARC), to sinter the nanoparticles for additional mechanical strength, and to prepare the nanoparticles in a hydrophilic state that allows simple capillary filling of the nanochannels with buffer/sample solution.

It will be readily understood that this is a very flexible nanochannel fabrication process. For silica nanoparticles, a simple dry etch step allows for reservoirs (wells) with access to entry ports of the nanochannels and to provide electrodes for electrophoretic transport and stretching. Porous barriers composed of the same porous materials can be inserted along the nanochannels with an additional exposure in the initial level of photoresist before the ARC-etch and particle spin-on steps. As discussed below, these barriers may be used to accumulate sample molecules of interest in the sample and localize the translocation of those molecules through the roof. An additional feature is the ability to stack several nanochannels with either parallel or perpendicular nanochannel directions, simply by repeating the above sequence of processes prior to the calcination. See, e.g., FIG. 6, which shows stacked nanochannels. In this particular case, both sets of nanochannels are in the same direction; however, it is possible to define the second set of nanochannels at any angle with respect to the first set, in particular, an orthogonal direction may have some advantages in introducing reagents in specific positions along the first set of nanochannels. In addition to the nanochannel structure it may often be desirable to introduce a secondary roof spaced away from the nanochannel roof. This ensures a flat surface for the buffer solution that moves from the nanochannels to the roof, provides a channel for directing the sample molecules away from the pore and allows an additional electrode for controlling the translocation velocity.

Figure 7A:
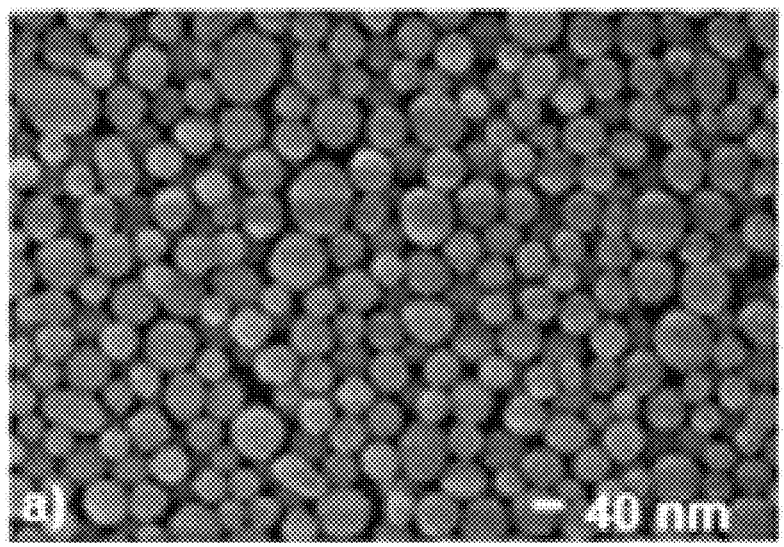
FIG. 7A is a high resolution SEM image of the top surface of the nanochannel roof.

FIG. 7A shows a high-resolution SEM image of the top of the roof of the nanochannel chip following the calcination step. The range of sizes both of the nanoparticles and of the spacing between the nanoparticles (i.e., nanopore size) that form the exits of the tortuous nanopores can be clearly seen. Note that the nanopores are not uniform throughout the roof and the smallest constriction may not be observed in this top-down image.

Figure 7B:
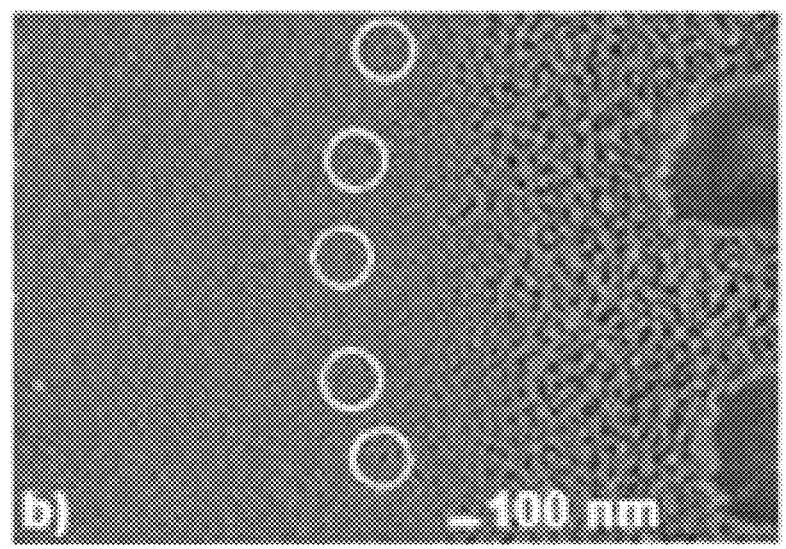
FIG. 7B is a high resolution SEM of the top of the nanochannel chip after CVD deposition (left side) and partial etching (right side).

FIG. 7B shows a high resolution SEM image of the top surface of the roof following an optional deposition of a chemical vapor deposition (CVD) film (e.g., $Si_3N_4$) and reactive ion etching (RIE) to open wells for introducing samples into the nanochannels. The left side of the image was masked during the etch, the $Si_3N_4$ film clearly covers the spaces between the nanoparticles that are evident in FIG. 7B. At the right side of the SEM image in FIG. 7B, the RIE etching has proceeded to the point that the roof over the channels has been removed. The CVD film has largely covered the larger scale (~10's of nm linear dimension) nanochannel pores, but some of the larger pores are beginning to be evident in the transition region between the as-deposited and the etched regions as marked by the white circles. The density and dimensions of these pores may be controlled by: adjusting the nanopore size dispersion; the use of atomic layer deposition (ALD) before the CVD step to seal a subset of the pores in the nanopore roof; and/or the use of different overlayers (either dielectric or metal prior to the active metal layer).

Figure 8A:
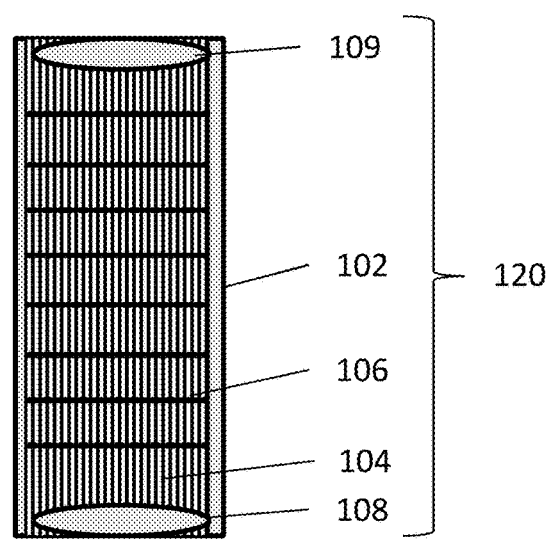
FIG. 8A is a top view of a nanochannel chip, according to various embodiments of the present disclosure.
Figure 8B:
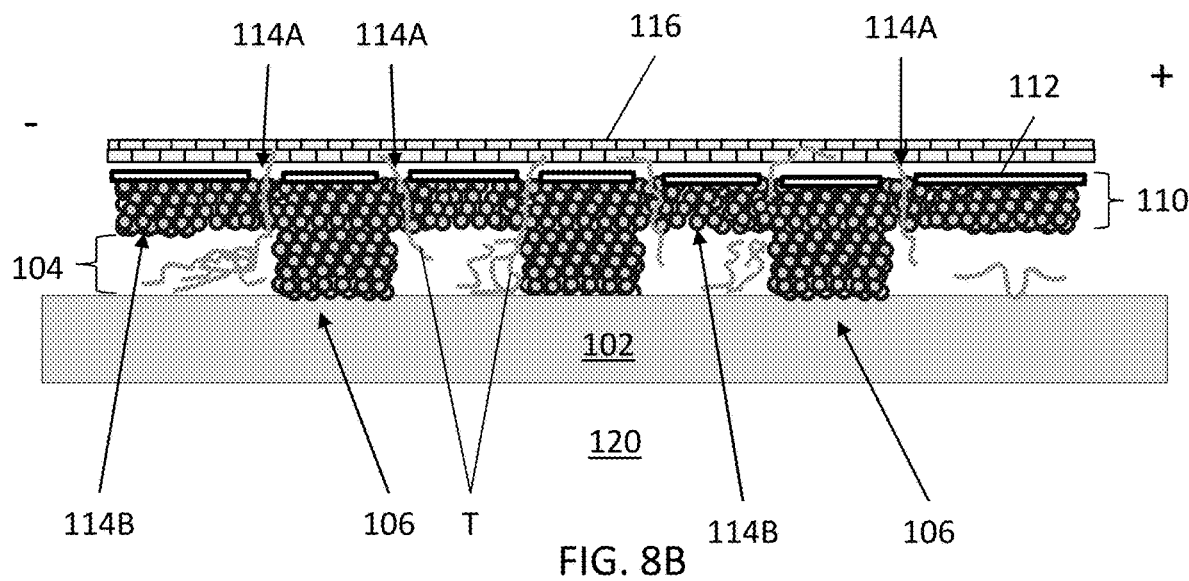
FIG. 8B is a cross section of the nanochannel chip of FIG. 8A.
Figure 8C:
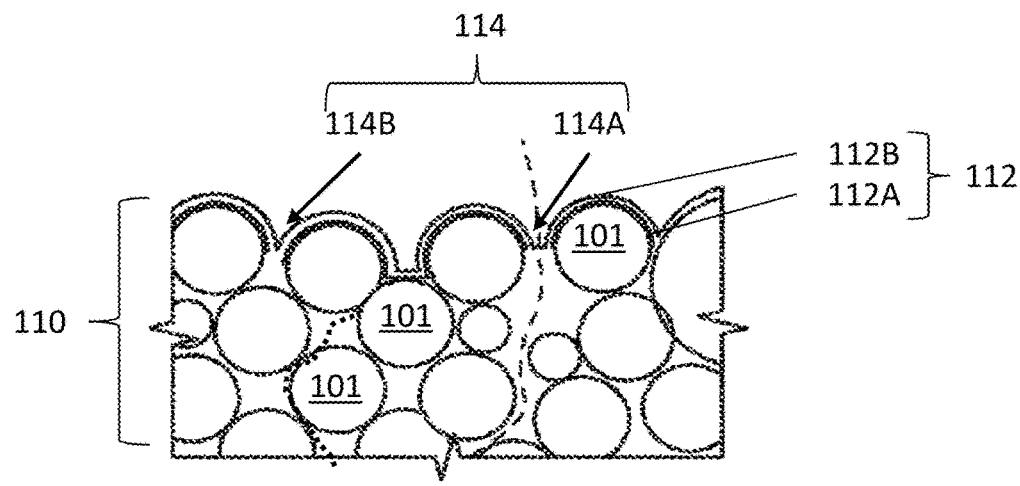
FIG. 8C is a magnified view of the roof of the chip of FIG. 8B.

FIG. 8A is a top view of a nanochannel chip 120, FIG. 8B is a cross section of the nanochannel chip 120 along one of the nanochannels, and FIG. 8C is an enlarged view of a portion of the roof of FIG. 8B. Referring to FIGS. 8A-8C, the nanochannel chip 120 may include nanochannels 104 disposed on a substrate 102. The nanochannel chip 120 may also include a first well 108 and a second well 109 fluidly connected to opposing ends of the nanochannels 104. A number of porous barriers 106 may be disposed in each of the nanochannels 104. In some embodiments, the nanochannel chip 120 may include additional wells that are fluidly connected to additional nanochannels.

The barriers 106 may be disposed perpendicular to the nanochannels 104 and may be configured to partially block the nanochannels 104. In some embodiments, the barriers 106 may be disposed equidistantly along the lengths of the nanochannels 104. In other embodiments, the spacing of the barriers 106 may be varied. The barriers 106 may have substantially the same width or the width of the barriers 106 may vary. For example, thin barriers 106 may be disposed at the beginning of the nanochannels 104 and wider barriers 106 toward the ends of the nanochannels 104. The barriers 106 may be formed of the nanoparticles 101, as discussed above.

Referring to FIGS. 8B and 8C, the nanochannel chip 120 may include a porous roof 110 covering the nanochannels 104. The roof 110 may comprise a layer of deposited nanoparticles 101 as discussed above, such that the tortuous nanopores 114 (i.e., 114A and 114B) may be formed between the nanoparticles 101. The roof 110 may be substantially thinner than the barriers 106. For example, the thickness of the barriers 106 may be on average ten or more times thicker than the roof 110.

By controlling the speed, direction, and ease at which sample DNA strands translate over and through the various nanopores 114 of a nanochannel chip 120, the accuracy and efficiency of the optical sequence read in an embodiment optical system 100, 160 (See FIGS. 11A and 11B) may be improved. Various modifications to both the nanochannel chip 120 may impact the size, density and alignment of the nanopores 144, which in turn may impact the speed, direction, and ease at which sample DNA strands translate over and through the various nanopores 114 of a nanochannel chip 120. Further treatments to the nanoparticles 101 as well as the applying an electrical field may also impact the speed, direction, and ease at which sample DNA strands translate over and through the various nanopores 114 of a nanochannel chip 120. As above, by modifying the speed, direction, and ease at which sample DNA strands translate over and through the various nanopores 114 of a nanochannel chip 120, the accuracy and efficiency of the optical sequence read may be improved.

Reducing the Density and Size of Nanopores

In an embodiment, the tortuous nanopores 114 in the roof 110 of a nanochannel chip 120 may be partially sealed with an ALD process that uniformly coats the exterior and interior surfaces of the nanoparticle roof 110. Since the size dispersion of the nanoparticles 101 results in a size dispersion of the tortuous nanopores 114, a process that uniformly shrinks all of the nanopores 114 will seal some of the pores while reducing the size of others that start out with larger dimensions. Accordingly, the nanopores 114 may be referred to as unsealed nanopores 114A and sealed nanopores 114B.

Alternatively, the ALD process may be configured to coat only the exposed top surface of the nanoparticle roof 110 by using an ion-assisted ALD deposition process. Any number of materials may be used for the ALD process including, but not restricted to: $SiO_2$, $Al_2O_3$, $HfO_2$ and Ag.

For example, the nanoparticle roof 110 may include a film 112 disposed on an outer surface of the layer of nanoparticles 101. The film 112 may be configured to partially seal the roof 110. In particular, the film 112 may include at least a nanopore sealing layer 112A that may be configured to seal a portion of the nanopores 114. Accordingly, the nanopores 114 may be referred to as unsealed nanopores 114A and/or sealed nanopores 114B dependent upon whether a given nanopore is sealed via the film 112 or unsealed. The film 112 may be formed by chemical vapor deposition (CVD), atomic layer deposition (ALD), electron beam evaporation, a combination thereof, or the like. For example, CVD may be used to form an 80- to 120-nm layer of $Si_3N_4$ or $SiO_2$ over the roof 110. A further application of 10- to 20-nm ALD layer of silica ($SiO_2$) or alumina ($Al_2O_3$) over the CVD deposition layer may further reduce the roof pore size. Other possible approaches utilize $HfO_2$ and $Al_2O_3$, which can be, for example, deposited using standard semiconductor protocols for ALD.

Referring to FIG. 8C in particular, according to various embodiments of the present disclosure, the nanoparticle roof 110 is shown to include nanoparticles 101 of three different diameters to represent the dispersion in nanoparticle size. The nanoparticles 101 may form a close-packed quasi-hexagonal lattice disturbed by steric effects as a result of the size dispersion, giving rise to a non-uniform set of tortuous pathways through the nanoparticle roof 110.

The present disclosure provides for the formation of tortuous nanopores 114 (114A and 114B) in the nanoparticle roof 110 that can be further decreased in size and density by standard film deposition processes such as e-beam evaporation, sputtering, CVD and/or conformal ALD. The film deposition both forms the sealed nanopores 114B and also decreases the sizes of the unsealed nanopores 114A, allowing only a single long chain molecule to transit through the nanopore 114A at a time. In other words, the sample molecules S may pass through the unsealed nanopores 114A in single file, such that only one sample molecule S emerges from each unsealed nanopore 114A at a time.

The CVD can be adjusted to deposit a porous layer, much like a blanket of snow, over the nanopores 114. This CVD process can be tuned for varying degrees of film porosity by variation of the deposition conditions. An example of the process parameters used for the CVD deposition of silicon nitride include: T=300° C.; pressure of 600 mTorr; RF power of 50 W; and flow rates of [$SiH_4$] 30 ccm, [$NH_3$] 50 ccm, [$N_2$] 15 ccm. In various embodiments, the opening dimension of a nanopore is not necessarily the tightest constriction along the pore.

Wells

The wells 108, 109 may be formed by etching through the roof 110 and the sidewalls of the nanochannel chip 120 to provide ports for introduction of various fluids to the nanochannels 106. In one embodiment a buffer solution containing DNA may be introduced to one well (e.g., 108) and a similar buffer solution without DNA may be introduced through an opposing well (e.g., 109) on the opposite end of the nanochannels 106. Electrodes may also be introduced to the wells and the current monitored to assure continuous filling of the nanochannels 104.

Barriers

In various embodiments, the barriers 106 may be configured to direct sample molecules, such as long chain nucleic acids or proteins, into the adjacent unsealed nanopores 114A. For example, when an electric field is applied to the nanochannels 104, the sample molecules (i.e., DNA strands) may be driven towards the barriers 106, such that the sample molecules aggregate adjacent to the nanopores 114A. As such, the probability that the sample molecules may enter the nanopores 114A may be increased in the vicinity of the barrier 106 edges.

Secondary Roof/Cover

Figure 9A:
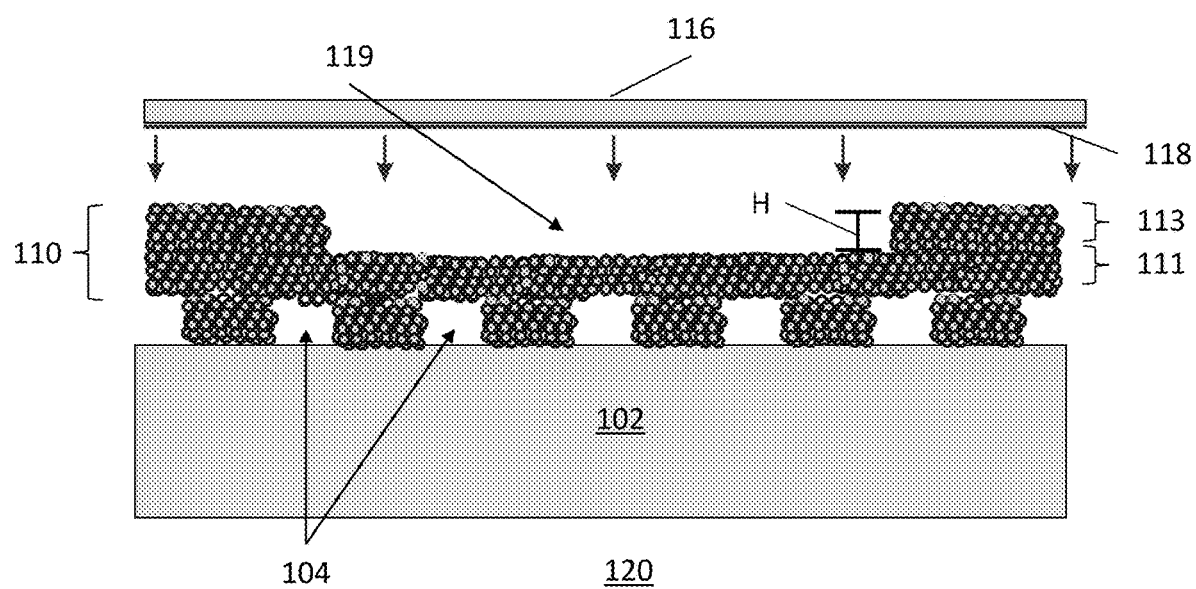
FIG. 9A shows a schematic illustration of a process for forming a cover over the porous nanoparticle roof.

Referring to FIG. 9A, in some embodiments, the nanochannel chip 120 may include a non-porous cover 116 disposed above the nanoparticle roof 110 (including film 112). The cover 116 may be optically transparent and may be made of a material such as glass or plastic. In other embodiments, the cover 116 may be optically transparent and electrically conductive. For example, the cover 116 may be made of a material such as an optical glass covered with a thin film of indium tin oxide (ITO) or the like to allow application of an electrical potential.

The cover 116 may provide multiple enhancements to the nanochannel chip 120. For example, the cover 116 may provide a micro- or macro-flow channel for the buffer/molecular solution on exiting the nanopores 114A to allow removing them from the region of the nanopores and controlling the local humidity at the nanopores (e.g., control evaporation rates). The cover 116 may provide an optical quality surface for far-field optical measurements. When electrically conductive, the cover 116 may allow for further manipulation of the quasi-static electric fields in the vicinity of the tortuous nanopores 114A to control the translocation of sample molecules. Additionally, the volume of buffer solution in the region between the nanoparticle roof 110 of the nanochannels 104 and the bottom of the cover 116 may be adjusted to be comparable to the volume of buffer in the porous wall/roof nanochannels which is important for the use of an applied voltage to control the DNA translocation as described below. Additionally, this configuration separates the DNA-containing buffer from a liquid atop the cover allowing the use of immersion microscope objectives offering higher resolution than air-based imaging approaches.

Figure 9B:
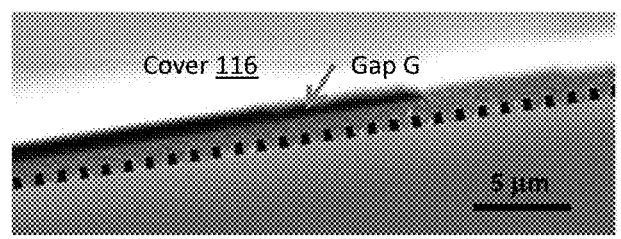
FIG. 9B is a SEM image of a fabricated two level structure with a porous nanoparticle roof and a secondary solid roof.

FIG. 9A is a sectional view showing the assembly of the cover 116 on corresponding structures of the nanochannel chip 120, according to various embodiments of the present disclosure. FIG. 9B is a micrograph showing the assembled nanochannel chip 120 of FIG. 9A. Referring to FIGS. 9A and 9B, the cover 116 may be formed of a transparent material such as silicon, quartz, or fused silica. The nanoparticle roof 110 may include a nanoparticle layer 111 and one or more support pillars 113 formed on an upper surface of the nanoparticle layer 111. The nanoparticle layer 111 may be formed by depositing nanoparticles 101 as discussed above. Accordingly, the nanoparticle layer 111 may include nanopores 114 that extend there through.

The cover 116 may be attached to the support pillars 113. For example, the cover 116 may be attached to the pillars 113 by an adhesive layer 118 formed on the cover 116. The pillars 113 may be formed using a method similar to the method for forming the sidewalls of the channels 104. For example, the pillars 113 may be formed by controlling the spin-coating method, such that the pillars 113 form sidewalls of channels 119 disposed on an upper surface of the nanoparticle roof 110. A distance between adjacent pillars 113 (i.e., a width of the channels 119) may range from about 0.5 µm to about 2.0 µm, such as from about 0.75 µm to about 1.5 µm, or about 1 µm, and no roof is formed on the pillars 113. Accordingly, the distance between adjacent pillars 113 may be, for example, 1000× greater than a width of the channels 104.

The pillars 113 may have a height H ranging from about 0.25 µm to about 1 µm, such as about 0.5 µm. Accordingly, the pillars 113 may be configured to separate the cover 116 and the upper surface of the nanoparticle layer 111, by a distance substantially equal to the height H of the pillars 113.

The adhesive layer 118 may be prepared by spin-coating one side of the cover 116 with a dilute polydimethylsiloxane (PDMS) solution, which may include a mixture of PDMS and Hexane. Next, the adhesive layer 118 side of the cover 116 may be pressed gently onto the top of the pillars 113, and annealed on a hot plate at about 175° C., for about 5 minutes. The cover 116 should be flexible enough to accommodate any bending of the chip substrate 102 and provide a uniform spacing between an upper surface of the nanoparticle roof 110 and the bottom of the PDMS coated cover 116.

Electromagnetic Enhancement Structures

As previously described herein, the nanoparticle roof may include a film 112 (depicted in FIG. 8C) disposed on an outer surface of the layer of nanoparticles 101. In one embodiment, the film 112 may be configured to, or may include structures configured to, localize and enhance electromagnetic fields. Additionally, or alternatively, in other embodiments, an additional film (not shown) may be added to film 112 and may be configured to, or may include structures configured to, localize and enhance electromagnetic fields.

For example, the film 112 may be a single layer structure including a metallic film and/or dielectric layer. Yet still, in other embodiments, the film 112 may be a multilayer structure including one or more metallic and/or dielectric layers disposed on a nanopore sealing layer, such as a silicon nitride layer or a silicon dioxide layer. Accordingly, in addition to the nanopore sealing layer 112A, the film 112 may include an electromagnetic-field enhancement structure 112B. For example, in some embodiments, the electromagnetic-field enhancement structure 112B includes at least one metal film. In some embodiments, the electromagnetic-field enhancement structure 112B includes at least one metal film and an insulating layer or structure. Yet still, in another embodiment, the structure 112b may include up to three layers, including an insulator layer disposed between two metal layers to thereby form the electromagnetic-field enhancement structure 112B. Accordingly, the structure 112B may include a metal-insulator-metal (MIM) film.

In some embodiments, at least a metallic layer of the electromagnetic-field enhancement structure 112B may be deposited with a directional process such as, but not limited to, electron beam evaporation. Accordingly, by using such a process of deposition, the metallic layer may be conformal with the fine structure of the nanoparticle roof 110, and in particular will have holes (apertures, openings, etc.) that are aligned with and on the scale of the openings of the tortuous nanopores 114 at the top of the nanoparticle roof 110. This is a self-aligned process, guided by the directional deposition and the topology of the nanoparticle roof 110, so no lithography step is required.

In the alternative, localized metal structures may be included, such as: a nanoscale pillar, a dipole structure (two metal triangles pointed at each other with a small gap between them) or a "C" aperture (a metal loop with a small gap). Each of these produces large fields under optical excitation. These structures are defined by a lithographic step, so they are appropriate for situations in which the location of the nanopore is known a priori such as in the case of manufactured nanopores produced by processes such as electron-beam lithography or ion-beam milling. Alternatively, there is a stress associated with the metal deposition that can shift the underlying particles and lead to self-alignment of pores with the edges of the metal structures.

In some embodiments, the electromagnetic-field enhancement structure 112B may include a metallic layer plasmonic structure that locally enhances electromagnetic fields and provides single base measurement capability (e.g., together with the nanopore, spatially localizes incident electromagnetic fields to a spatial scale of about 1 $nm^3$). Accordingly, herein the electromagnetic-field enhancement structure 112B may be referred to herein as a "MIM layer" or a "field enhancement structure". The MIM layer 112B may be self-assembled to the nanopores 114, providing a simple, inexpensive, and self-aligned fabrication process. The <1 nm insulator thickness provides the necessary base-level resolution and the wide pore spacing allows for independent far-field optical readout, providing a massively parallel sequencing capability. Furthermore, both labeled (fluorescence) and unlabeled (SECARS) optical readout mechanisms can be used with this system.

The electromagnetic enhancement is related to the surface-enhanced Raman scattering that is observed in small gaps that form in aggregated colloidal Au and Ag nanoparticle systems, which gives rise to single molecule detection sensitivity. The film, which includes the MIM layer 112B, may also add a magnetic dipole resonance to the electric dipole resonance formed in the colloidal system which further extends the electromagnetic resonance. The physics of this interaction is related to the creation of metamaterials that exhibit both negative permittivity (free electrons in a metal moving to oppose the applied electric field of an electromagnetic wave) and negative permeability (current loops between two metal surfaces opposing the applied magnetic field of an electromagnetic wave).

Mesoporous (Alignment) Layers

As noted above, there are several options related to the electromagnetic field-enhancement structures. There is an enhancement associated with a localized surface plasma wave resonance (LSRP) with either a localized metallic structure or a hole in an otherwise uniform metallic structure. Above a method is described for self-aligning holes (e.g., apertures, openings, etc.) in a MIM structure with unsealed pores 114A in the nanoporous roof 110. In a second embodiment, the MIM structure can be formed on an intermediate alignment layer with a high density of nanoscale pores such as a mesoporous silica layer or a graphene or other 2D material layer. In a third embodiment, the MIM layer can be formed with larger scale nanostructures (~100-200 nm) specifically designed to be resonant with the electromagnetic fields of the incident optical fields. Then the issue becomes aligning these larger structures with the tortuous nanopores in the roof of the nanochannels. This is also a self-aligned process in that the polymer molecules generate image charges in the metal of the MIM structure and emerge from pores close to the edge of the lower metal layer. Additionally, stress effects associated with the metal deposition can lead to localization of the pores just at the edges of the metal structure.

Figure 10:
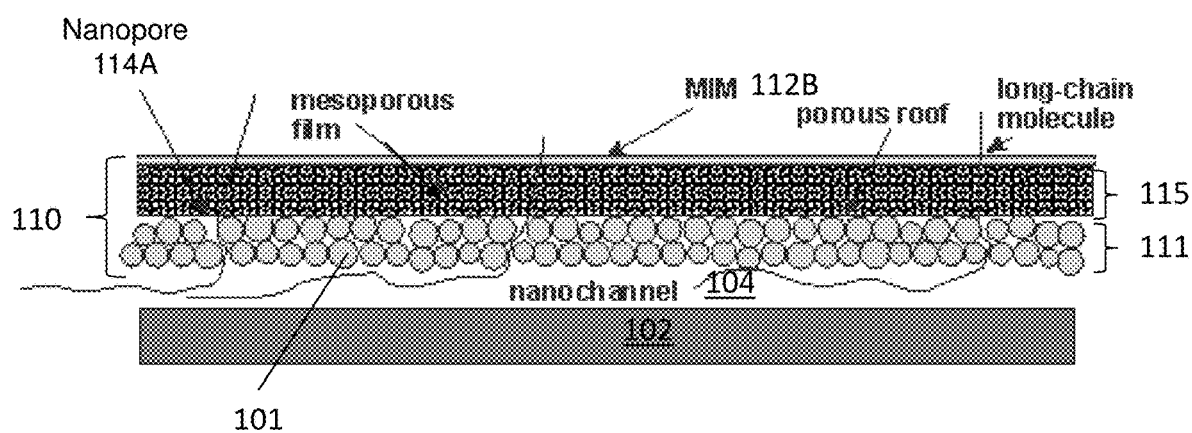
FIG. 10 is a sectional schematic view of an addition of a mesoporous film disposed atop a porous roof, according to various embodiments of the present disclosure.

FIG. 10 is a sectional view of a modified version of the nanochannel chip 120, according to various embodiments of the present disclosure. Referring to FIG. 10, the nanoparticle roof 110 may include a nanoparticle layer 111 comprising deposited nanoparticle particles 101 as described above, an alignment layer 115 disposed on the nanoparticle layer 111, and an electromagnetic-field enhancement layer 112B disposed on the alignment layer 115. In particular, the alignment layer 115 may be deposited on the nanoparticle layer 111, and the electromagnetic-field enhancement layer 112B may be deposited on the alignment layer 115.

For example, the alignment layer 115 may be formed by depositing a microporous or mesoporous crystalline material on the nanoparticle layer 111. In various embodiments, the alignment layer 115 may be formed after partially sealing the nanoparticle layer 111 using a nanopore sealing layer 112A (see FIG. 8C). The alignment layer 115 may be formed of mesoporous silica or a substantially two-dimensional (2D) material such as graphene. The alignment layer 115 may have a high density of uniform, crystalline nanoscale pores, with dimensions of the pores corresponding to atomic bond lengths that are at the nm level. For example, the alignment layer 115 may have a uniform porosity and an average pore size ranging from about 0.3 nm to about 3 nm. Accordingly, the alignment layer 115 may have a smaller average pore size and a higher pore density than of the nanoparticle layer 111 of the roof 110.

The electromagnetic-field enhancement layer 112B may be formed on the alignment layer 115 by depositing a first metal layer using a deposition process such as ALD. As a result, the structure elements of the alignment layer 115 may be covered by the first metal layer. Then a top down process such as a plasma-assisted ALD may be used to selectively cover the first metal layer with an electrically insulating layer, such as a silica layer. Finally a directed deposition process, such as e-beam deposition, may be used to form a second metal layer on the electrically insulating layer, to complete the MIM layer 112B.

Accordingly, the alignment layer 115 may operate as a template for the formation the electromagnetic-field enhancement layer 112B, such that pores of the electromagnetic-field enhancement layer 112B may be formed around and/or aligned with pores of the alignment layer 115. In other words, the first metal layer and the insulator layer of the MIM layer 112B may be formed conformally with the pores of the alignment layer 115. The top metal layer may be formed with a top-down process so as not to block the pores.

It may be difficult to ensure that the edges of electromagnetic-field enhancement layer 112B are aligned with the open nanopores 114 of the nanoparticle roof 110 of a nanochannel chip 120, such as when a electromagnetic-field enhancement layer 112B is formed directly on a partially sealed nanoparticle layer of a nanoparticle roof 110. As such, either the movement of sample molecules through the nanochannels 114 of the nanoparticle roof 110 and into the pores 114 of MIM layer 112B may be impeded due to pore misalignment or the electromagnetic hot spot may not be aligned with the unsealed tortuous nanopores.

The porosity of the alignment layer 115 may be configured to be high enough to ensure self-alignment of the pores of the electromagnetic-field enhancement layer 112B and the tortuous nanopores 114 of the nanoparticle layer 111, while providing isolation for optical monitoring of individual pores of the electromagnetic-field enhancement layer 112B. Accordingly, the alignment layer 115 may be provided to fluidly connect open nanopores of the nanoparticle layer 111 with pores or openings in the electromagnetic-field enhancement layer 112B, thereby improving sample throughput.

In some embodiments, the electromagnetic-field enhancement layer 112B may include films engineered so that small holes or pores supporting localized electromagnetic resonances self-align with the tortuous nanopores. Alternatively, the electromagnetic-field enhancement layer 112B can be structured to enhance the electromagnetic resonances. Typically, but not always, this takes the form of metal disks of ~100 nm diameter. Using a mesoporous film assures that the path from the nanochannel through the tortuous nanopore and then through a crystalline pore of the mesoporous material is not blocked. The electromagnetic resonances are concentrated at the edges of the metal structures. There is an attraction due to image forces between the negatively charged DNA in the nanochannel and the overlying metal film makes the pores just at the metal edges the preferred places for DNA translocation.

The structure of the electromagnetic-field enhancement layer 112B may be defined by several parameters: a) the overall structure should be resonant at the pump, Stokes and anti-Stokes wavelengths; b) the insulating gap width should be about 1 nm, which is commensurate with the size of a single base; c) the field enhancement is not uniform throughout the electromagnetic-field enhancement structure but is largest near the edges and is dependent on the polarization of the incident beams and the orientation of the base relative to the incident beams. The resonance wavelengths are also weakly dependent on the shape of the electromagnetic-field enhancement structure. The location of the nanopores where the ssDNA translocation will occur is just before the edge of the barrier. Ellipsoidal structures aligned with the edge of a barrier may be used, which may be roughly the scale of the resonance for the near-IR wavelengths (e.g., about 100 to about 200 nm in diameter), so that several features can fit in the 1-μm spacing between nanochannels.

Optical Detection Systems

Figure 11A:
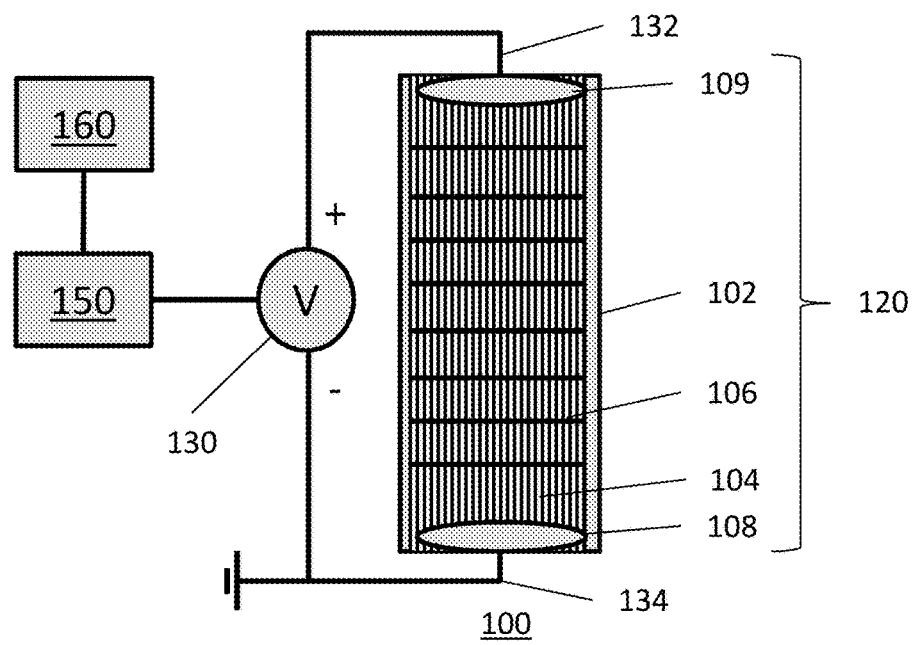
FIG. 11A is a schematic view of an optical detection system, according to various embodiments of the present disclosure.
Figure 11B:
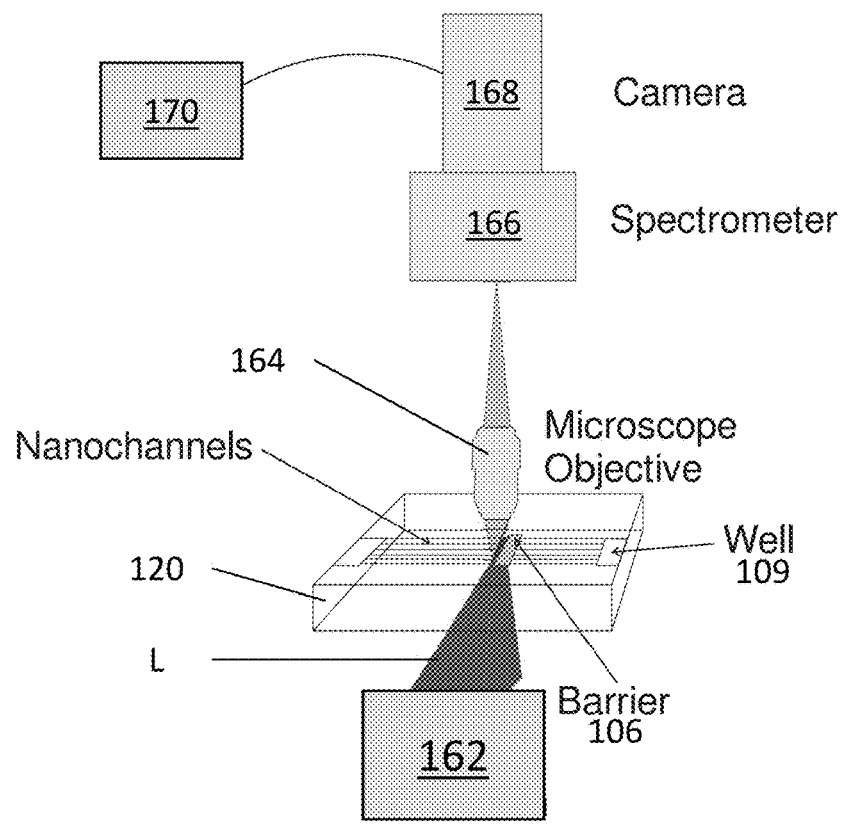
FIG. 11B is a schematic view showing components of the system of FIG. 11A.

FIG. 11A is a schematic view of a sequencing system 100, according to various embodiments of the present disclosure, and FIG. 11B is a schematic diagram including components of an optical system 160 of FIG. 11A. Referring to FIGS. 11A and 11B, the system 100 may include the nanochannel chip 120, a voltage source 130, a controller 150, and the optical detection system 160. The voltage source 130 may apply a voltage across electrodes 132 and 134 coupled to opposing ends of a nanochannel chip 120. The controller 150 may include a central processing unit and a computer readable memory.

The optical system 160 may include a light source 162, a microscope objective 164, a spectrometer 166, a camera 168, and a data processor 170. The light source 162 may be a coherent light source configured to illuminate one or more regions of the nanochannel chip 120. In some embodiments, the light source 162 may be disposed below the nanochannel chip 120 and may be configured to direct laser light L through the nanochannel chip 120 to illuminate at least one region of the nanochannel chip 120, such as a rectangular region of the upper surface of the nanoparticle roof 110 of the nanochannel chip 120. The 2D region may be disposed adjacent to a barrier 106 of the nanochannel chip 120, such that samples emerging from nanopores 114 of the nanoparticle roof 110 of the nanochannel chip 120 may be illuminated and detected. The long dimension of the rectangular area covers many nanochannels (spaced at, for instance, 1 μm), while the short dimension of the rectangular area is close to the barrier region which has the highest likelihood of a translocating long-chain molecule.

The light source 162 may include one or more laser sources. For example, the light source 162 may use a single laser source to generate high brightness coherent illumination. In other embodiments, the light source 162 may include two or more laser sources. For example, the light source 162 may include two narrow band laser sources having a frequency difference tuned to the Raman frequency, or the light source 162 may include one narrow band laser source having a smaller wavelength range that the characteristic Raman linewidth, and one broadband laser source having a wavelength range that encompasses the entire range of Raman shifts of interest.

The objective 164 may be a microscope objective configured to collect light from the illuminated 2D region that includes Raman signals generated when the coherent light interacts with single nucleotide bases disposed in the field enhancement structures located at the ends of unsealed nanopores. In particular, the objective 164 may be configured to magnify the light collected from the focal region of the sample onto an inlet slit of the spectrometer 166. The optics may be configured such that the long dimension of the illuminated 2D rectangular area is imaged along the inlet slit of spectrometer 166 such that different positions along the slit correspond to different nanopores in different nanochannels.

The camera 168 may be configured to image a focal plane located at an outlet of the spectrometer 166. A slit normally disposed at the outlet may be removed. As a result, the camera 168 may generate a 2D image, where a lengthwise direction along the 2D image corresponds the position of the active molecules coming through multiple tortuous nanopores, and a widthwise direction corresponds to either the Stokes (for Raman scattering) or the anti-Stokes (for CARS) signature of the base currently passing through the electromagnetic hot spots generated by illumination of the electromagnetic-field enhancement structure. Accordingly, the camera may be configured to generate image data including Raman spectra data for individual bases of one or more long chain polymeric molecules.

This concept may be extended by illuminating multiple linear regions and by including multiple parallel slits at the entrance of the spectrometer 166. The illuminated regions may be separated by a sufficient distance to allow monitoring to the Raman spectra between adjacent regions.

The images generated by the camera 168 may include full wavelength range Raman spectrum data and may be output to the electronic processor 170. The data processor 170 may include a central processing unit and a memory comprising a computer readable medium. The optical processor 170 may include a central processing unit configured to analyze the images provided by the camera 168 to detect individual bases as nucleic acids translocate through the nanochannels of the chip 120, based on the corresponding Raman spectra, as discussed in detail below.

Accordingly, the optical system 160 may be configured to monitor a multiplicity of tortuous nanopores 114, while providing positive identification of the Raman spectra of individual nucleotide bases, using spectral information from several different Raman bands. In addition, the optical system 160 may be configured to detect a full wavelength Raman spectra range, such as a Raman spectra range ranging from a wavenumber of about 400 $cm^{-1}$ to a wavenumber of about 1800 $cm^{-1}$, such as a Raman spectra range ranging from a wavenumber of about 500 $cm^{-1}$ to a wavenumber of about 1700 $cm^{-1}$.

Chip Passivation

According to various embodiments of the present disclosure, channel to channel transport uniformity may be improved by applying a passivation agent to the nanochannel chip 120. For example, a passivation agent, such as lipids or bovine serum albumin (BSA) may be applied to the channels 104 of the nanochannel chip 120. The passivation agent may operate to ensure that most of the nanochannels 104 are active and are not blocked as a result of fabrication issues.

As fabricated, nucleotide transport in the nanochannels 104 may not be uniform across an array of nanochannels. This is likely due to random asperities and chemical impurities introduced from the starting nanoparticle materials, as well as from contaminants associated with the as-received DNA. Adding a passivation element such as a lipid bilayer or bovine serum albumin (BSA) decreases the trapping interactions with the walls associated with these inhomogeneities and provides a more uniform DNA transport across many channels.

Figure 12A:
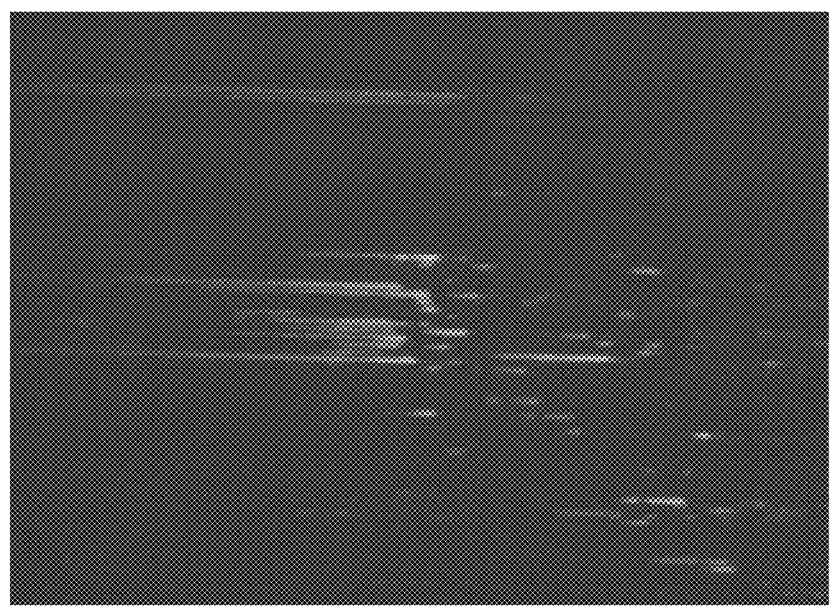
FIGS. 12A, 12B, and 12C show the difference in homogeneity of dsDNA loading for an unpassivated chip (FIG. 12A), a BSA passivated chip (FIG. 12B), and sonicated lipid bilayer passivated chip (FIG. 12C).
Figure 12B:
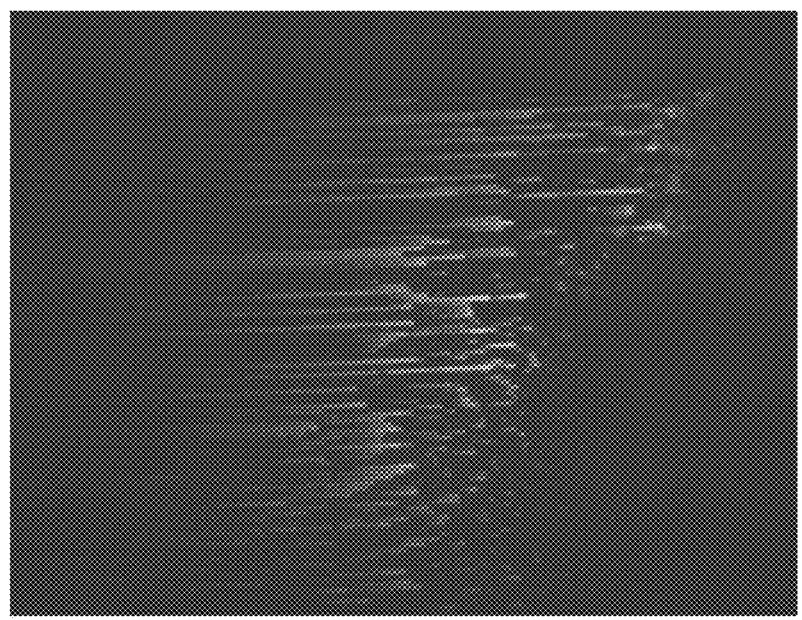

FIG. 12A is a photograph showing DNA propagation through nanochannels of a comparative non-passivated nanochannel chip, and FIG. 12B is a photograph of DNA propagation through nanochannel channels of a nanochannel chip that is passivated with BSA. The passivated nanochannel chip used to generate the photo in FIG. 12B was soaked for 12 hours, at 4° C., in a solution containing 800 μg/ml BSA diluted 100× diluted tris/borate/EDTA (TBE) buffer. Then the nanochannel chip was rinsed with the TBE buffer for 5 min on a shaker. The same treatment was applied to the comparative nanochannel chip 120 used to generate the photo in FIG. 12A, except that the BSA was not included in the solution.

λ-phage DNA intercalated with YOYO dye was introduced into wells of nanochannel chip. An electric field was applied along the nanochannels of chip. As shown in FIGS. 12A (unpassivated chip) and 12B (passivated chip), the passivated chip exhibited higher DNA penetration and movement uniformity through the nanochannels is evident in the image of the passivated chip of FIG. 12B as compared with the unpassivated chip image FIG. 12A.

Figure 12C:

FIG. 12C is a photograph showing a nanochannel chip passivated with a lipid bilayer treatment. Fluorescein-labeled phospholipid DHPE and unlabeled lipids (POPC lipids) were used to passivate the nanochannels. Green fluorescence is seen due to the formation of uniform lipid bilayers (LBL) in the nanochannels. 1% lipids (DHPE+POPC) were dissolved in 500 μl of methanol. Once completely dissolved, methanol was evaporated using a spinner and nitrogen chamber. Evaporated lipid was suspended in 500 μl of 100×-diluted TBE buffer and sonicated. Sonication was carried out at 130 W/30 KHz @20% amplitude with 20 pulses for 3 times on ice. Sonicated lipid was diluted by 20× in TBE and was deposited at the edge of the chip near the wells. Lipid vesicles enter the nanochannels to form uniform lipid bilayers. LBL was subsequently allowed to spread in the nanochannels.

ssDNA Introduction

Another objective of the invention is to provide techniques for introducing single stranded DNA (ssDNA) to the nanochannels and tortuous nanopores 114.

For sequencing applications, use of ssDNA may ensure that a single base dominates the Raman spectrum and avoids ambiguities that result due to the association of the detected bases with both strands of the double helix. The ssDNA may be formed either by heating (melting) of a dsDNA solution at 95° C. for 10 minutes and snap cooling (rapidly reducing the temperature by immersing the sample in an ice water bath). The snap cooling prevents the re-formation of the ssDNA back into dsDNA and retains the individual ssDNA. Alternatively, an exonuclease may be used to successively remove bases from both 5'-ends of the dsDNA. For the heat treatment, two ssDNA molecules of the same contour length (~16 µm for λ-phage) as the original dsDNA may be formed. For the exonuclease treatment two half-length segments (~8 µm for λ-phage) may be formed with the other half segments reduced to individual deoxynucleotide monophosphate molecules by the action of the exonuclease. Both of these processes may be done either before (ex-situ) or after (in situ) introduction of the DNA into the nanochannels 104 of a nanochannel chip 120. For the ex-situ case, the introduction of the ssDNA may be either through wells at the edges of the nanochannel chip 120 or through tortuous nanopores 114 in the nanoparticle roof 110 of the nanochannel chip 120. The ssDNA in the nanochannels 104 may be observed using OliGreen a fluorescent dye that binds preferentially to ssDNA. In contrast to the extensive literature on dsDNA in nanochannels, there are very few publications on conformation and transport of ssDNA in nanochannels.

ssDNA is both much more flexible than dsDNA and can find self-complementary regions along the strand that leads to a more tightly balled-up structure that is potentially more difficult to linearize in the nanochannels.

Figure 13:
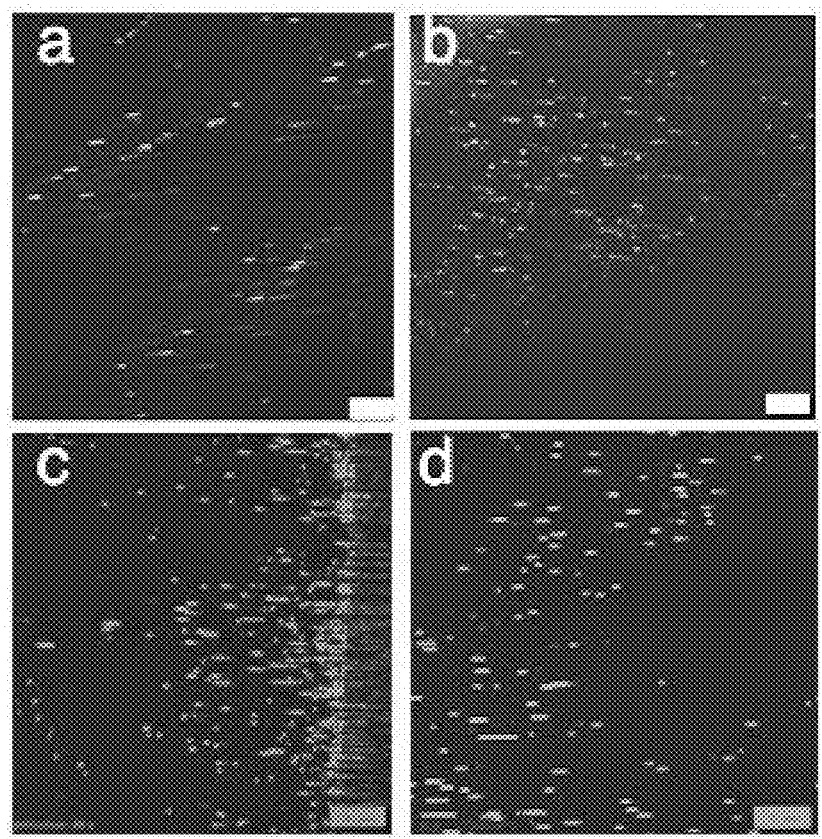
FIG. 13 shows results for OliGreen dyed ssDNA (λ-phage) in the nanochannels, including: panel a) in-situ exonuclease digestion; panel b) ex-situ exonuclease digestion introduction through tortuous nanopores; panel c) ex-situ exonuclease digestion introduction through wells etched into nanochannels (wells are at right side of figure); and panel d) which is the same as panel c) after ssDNA has stretched in the nanochannels. In each panel, the marker is 20 μm.

FIG. 13 shows the results for exonuclease digestion. Panel a) shows the results for in-situ formation of the ssDNA. For the in situ preparation and staining of λ-ssDNA, 1- to 2 µl of 5-ng/µl λ-dsDNA was first introduced through the roof of the nanochannels, and the chip was heated at 95° C. for 10 min covered with 0.01×TE buffer. After 10 min, the chip was quickly transferred onto a pre-chilled to 0° C. Petri dish for snap-cooling for 2 min, washed once with 0.01×TE buffer and stained with OliGreen or YOYO-1 dye by incubation with the dye solutions for 1-hour at room temperature in the dark. After the incubation, the chip was washed with 0.01× TE buffer twice for 5 minutes to remove any excess dye.

FIG. 13, panels b and c show exonuclease digested ssDNA prepared in solution and introduced to nanochannels through roof and wells of chip, respectively. The markers represent a length of 20 µm; the observed ssDNA lengths are consistent with the full ~10 µm contour length of the exonuclease digested λ-phage DNA. Panel b) shows the results of ex-situ digestion and introduction of the ssDNA through the porous roof, demonstrating that the ssDNA transits the tortuous nanopores. Panel c) shows ex-situ formed ssDNA introduced into the nanochannels through wells observed on the right side of the image. This image shows many small bright dots corresponding to folded ssDNA near the entry port. These dots gradually stretch out in the nanochannels after ~10- to 15-minutes as seen in panel d) (scale bar is 20 µm).

Figure 14:
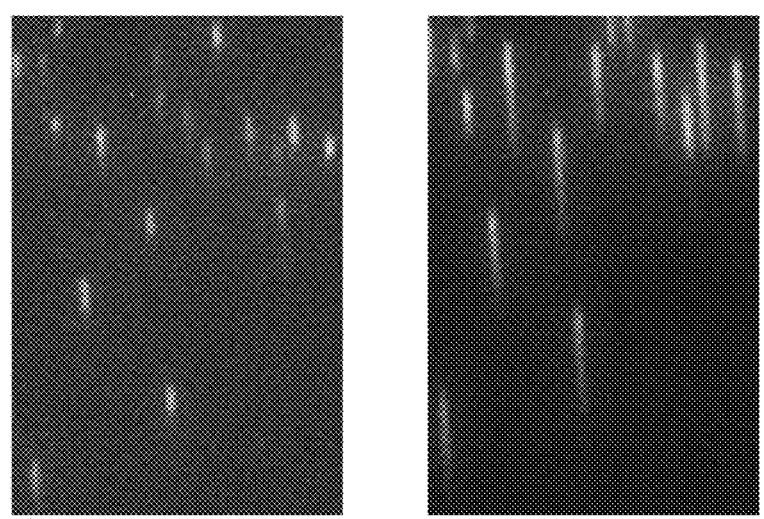
FIG. 14 shows two frames of a movie that was used to monitor the length of exonuclease ssDNA introduced from wells at the edge of a chip into the nanochannels. It takes about 6 min. to introduce the DNA, mount the chip in the microscope, and adjust the image.

FIG. 14 shows time lapse images of the ex-situ, exonuclease generated ssDNA introduced through the wells of the chip. It takes about 360 s to introduce the DNA, mount the chip in the microscope and image the ssDNA in the channels. FIG. 14A was taken at about 360 seconds after introduction of the ssDNA; FIG. 14B was taken after an additional 250 seconds. Note the correspondence of the individual DNA strands between the two figures as well as the much longer ssDNA strands in the later image.

Figure 15:
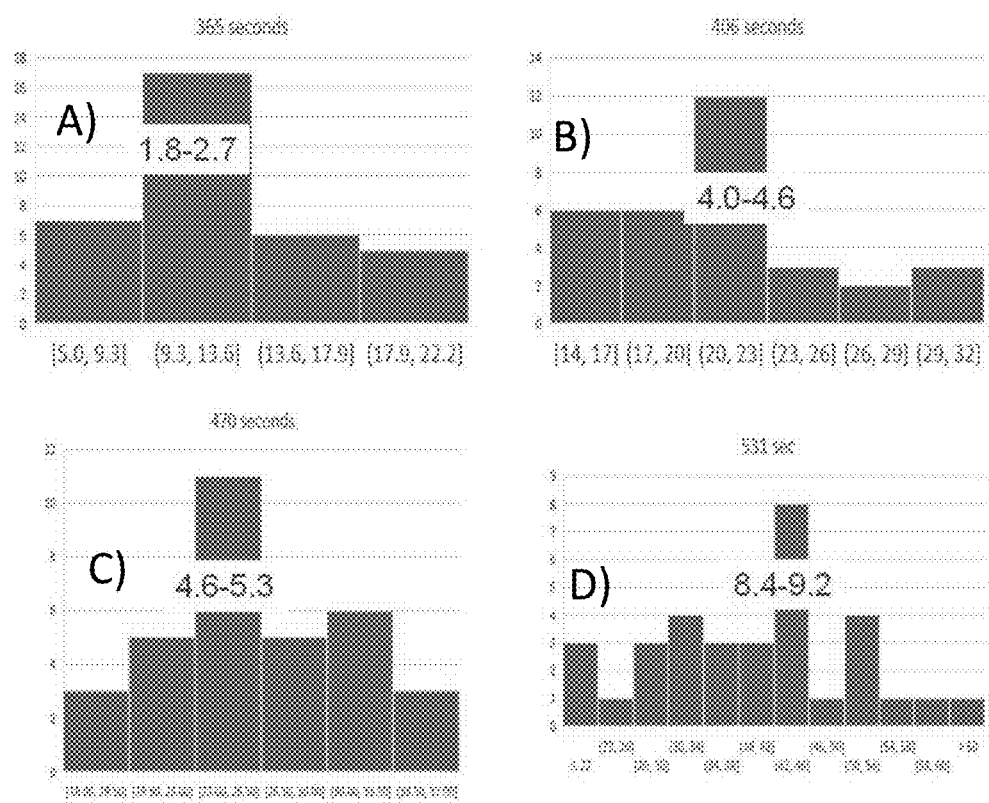
FIG. 15 shows histograms of the ssDA length measured at different times from the introduction, the gradual lengthening of the ssDNA is clearly observed.
Figure 16:
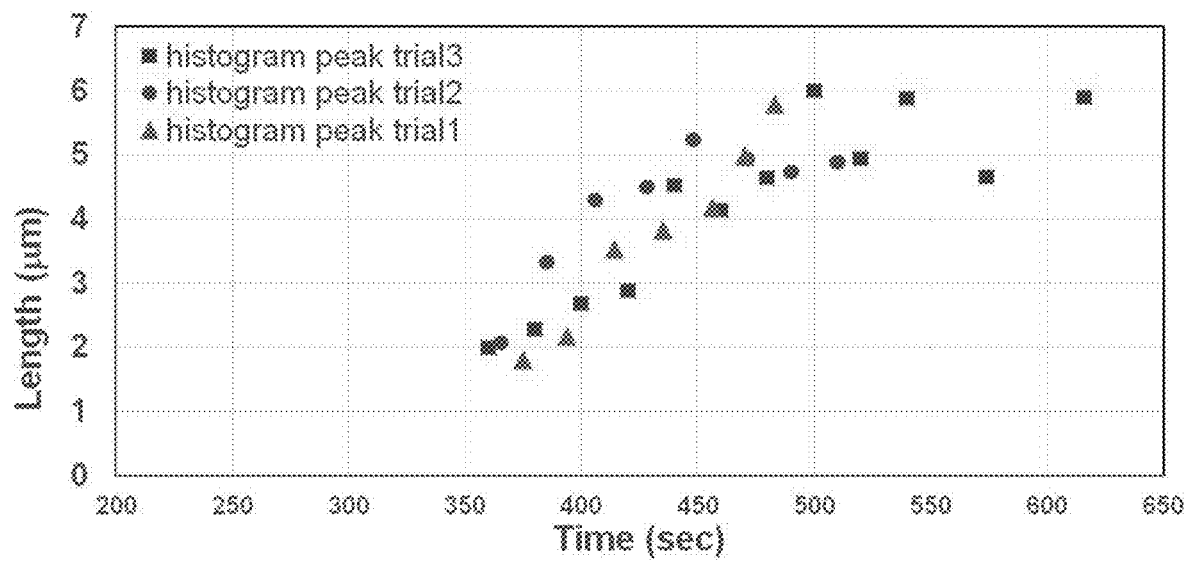
FIG. 16 shows plots of the histogram maxima vs. time for three different introductions of exonuclease produced lambda ssDNA (λ-ssDNA) into the nanochannels.

This is quantified somewhat in FIG. 15, which shows histograms of the length of 30 individual ssDNA molecules vs. time, and in FIG. 16, which plots the peak length vs. time. The ssDNA stretches out to approximately a full contour length over time. A very dilute buffer (TBE/100) was used, so the screening length was longer than the channel width. Since the SiO$_2$ walls are negatively charged, and the ssDNA is negatively charged the ssDNA is forced to the center of the wells and there is an effective pressure that leads to the unfolding of the ssDNA. There are many self-complementary sections of the lambda ssDNA that most likely account for the time scale of the unfolding.

Figure 17:
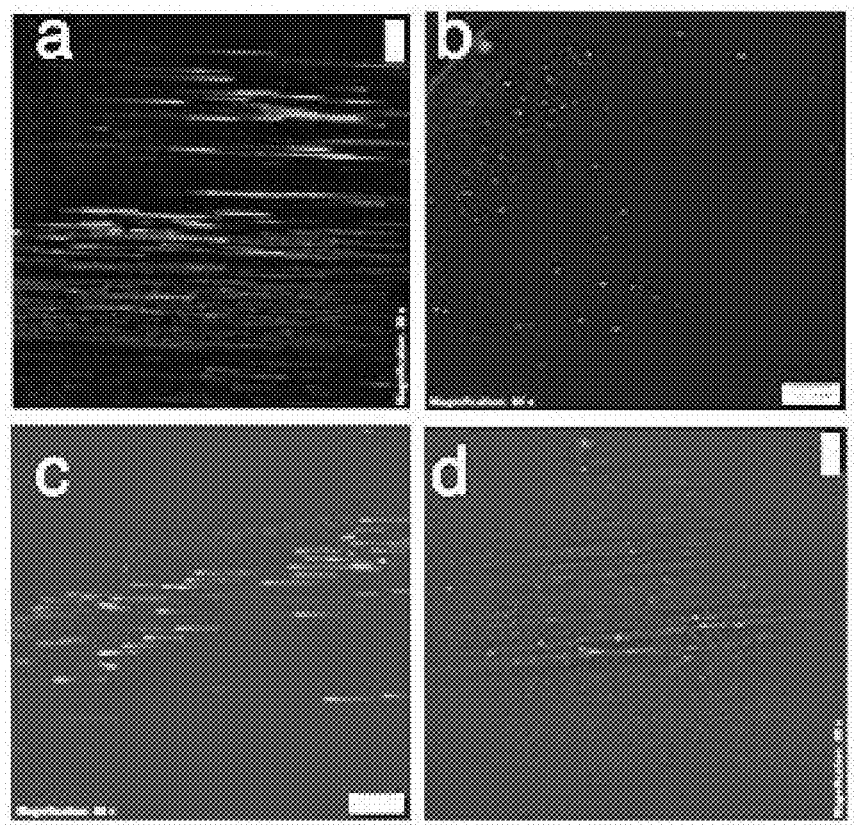
FIG. 17 shows results for heating and snap cooling to form ssDNA, including panel a) in-situ in the nanochannels; panel b) ex-situ formation and introduction through tortuous nanopores; panel c) ex-situ formation and introduction through wells etched into nanochannels; and panel d) which is same as panel a) but dyed with YOYO (specific to dsDNA) to show that the majority of the dsDNA has been converted to ssDNA. In each panel, the marker is 20 μm.

FIG. 17 shows OliGreen stained ssDNA generated from heating and snap-cooling of ds-DNA. Panel a) shows in-situ formation of ssDNA in the nanochannel chip 120. Here, λ-phage dsDNA was introduced into the nanochannels 104 through nanoparticle roof 110. Once the DNA was in the nanochannels 104, the nanochannel chip 120 was covered with 0.01×TBE buffer and heated at 95° C. on a heat block for 10 min to separate the dsDNA strands. After heating, the nanochannel chip 120 was snap cooled by placing it on atop a cold block for 5 min. Then the nanochannel chip 120 was stained with OliGreen and incubated at 1 hour at RT or 3-4 hours at 4° C., while protected from light. The nanochannel chip 120 was rinsed in TBE buffer to remove excess dye and stored in TBE buffer until imaged. The observed lengths are larger than the λ-phage DNA contour length due to pairing of multiple DNA molecules as a result of the self-complementary "sticky ends" of λ-phage DNA. Panels b) and c) show ex-situ heated and snap-cooled ssDNA in solution, introduced through pores and wells of the nanochannel chip 120, respectively. Panel b) is a shortly after the introduction and the ssDNA appears as bright, unresolved points. Panel c) was taken ~10 min. after introduction of the ssDNA, which appears as ~20 µm long streaks. The micrograph of panel d) was taken under similar conditions to panel a) but the dye was changed to YOYO, an intercalating dye that is dominantly specific for dsDNA, showing that a majority of the dsDNA has been converted to ssDNA.

By introducing the DNA strands into the nanochannels 104 (through either wells or nanopores on the porous roof) the ssDNA is initially folded into a small volume that appears as a bright unresolved point in our microscope (compare FIG. 14, panels b) and c)). Over a time scale of ~10- to 15-minutes, the ssDNA spontaneously stretches out to close to its full contour length (either 10- or 20-µm) in response to forces arising from electrostatic repulsion from wall charges (negative for SiO$_2$) and the negative charge on the ssDNA backbone, the resulting electric fields push the ssDNA to the center of the channel and exert a compressive force that leads to the elongation. The manipulation of the DNA strands may be advantageous for the sequencing operation since the stretching and unfolding facilitates the ssDNA introduction into the tortuous nanopores; providing a leading end and reducing entanglement. This process is assisted by the low ionic strength of the fluid which minimizes screening of the wall charges. This stretching of the ssDNA to its full contour length is very advantageous for sequencing operations.

Electric Fields

Another objective of the invention is to provide techniques to control the transport of the ssDNA in the nanochannels 104 and in the tortuous nanopores 114 by applying quasi-static electric fields (both static and time varying) to advance/slow/speed-up/reverse the ssDNA motion. This may be coupled with structural variations of the nanochannels and tortuous nanopores that provide additional control over the motion of the DNA. The variations include restricting the volume of water on the nanoparticle roof 110 of the nanochannels 104 to force the DNA back into the nanochannels 104 after it emerges through the tortuous nanopores 114; this allows using multiple tortuous nanopores to provide redundant measurements. The structural variations relate to the thickness and nanoparticle compositions of the nanoparticle roof 110 and the barriers 106 as well as ALD and CVD treatments as described above.

The application of electric fields to the chip provides a powerful technique to control the dynamics of nucleic acids (e.g., both dsDNA and ssDNA) motion through the nanochannels 104 and tortuous nanopores 114. With reference to FIG. 11A, an electrical voltage may be applied across electrodes 132, 134 by voltage source 130. As shown in FIG. 9B barriers 106 formed of a porous array of nanoparticles 101 can be fabricated to block the nanochannels 104. Importantly, the width of these barriers 106 along the direction of the nanochannels 104 may be much wider than the thickness of the roof, resulting in the DNA preferentially transiting the tortuous nanopores in the nanoparticle roof 110 under an applied field, rather than penetrating the thicker barriers 106. If there is a large water reservoir above the nanochannel chip 120, the DNA simply diffuses away from the nanochannel chip 120 once it has fully transited the tortuous nanopore 114. However, if the amount of water above the nanochannel chip 120 is restricted, either by only filling the nanochannels 104 from wells 108, 109 on the ends, or by adding a second cover slip 116 as shown in FIG. 8B, the DNA may be forced to transit the top of the barriers 106 by the applied electric field and then re-enters the nanochannel 104 rather than stay on top of the nanoparticle roof 110.

Figure 18:
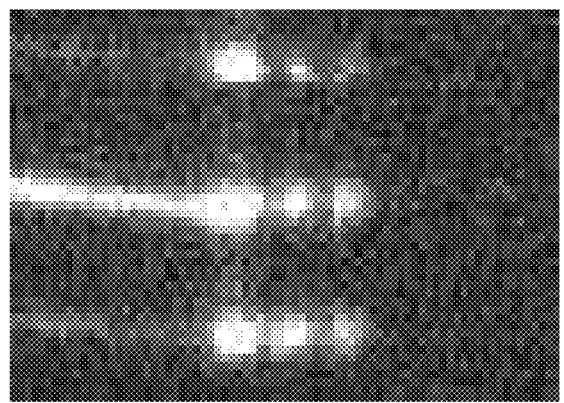
FIG. 18 shows a single frame of a movie where an electric field is used to move dsDNA (lambda phage) from left to right in the nanochannels. In the movie, the dsDNA is incident from the left, collects at the first (left most barrier), transits a tortuous nanopore in the roof to the top of the roof, moves across the barrier, reenters the nanochannel through a second tortuous nanopore after the barrier and repeats this process at the second and third barriers.

FIG. 18 shows a top-view fluorescence image from YOYO intercalated-dye-stained dsDNA (λ-phage) in 0.01× TBE buffer showing the DNA accumulating at three barriers under an applied electric field. The image in FIG. 18 is a still frame from a movie that was recorded using a 20× objective. The barriers 106 are 5 μm wide and are separated by 5 μm nanochannel segments. The nanochannel chip 120 was loaded with a drop of buffer solution without any DNA on the left well of the chip and a buffer solution with dsDNA on the right. Both buffer solutions filled the nanochannels 104 by capillary action. The current through the nanochannels 104 was monitored (many nanochannels electrically in parallel) to ensure that the nanochannels 104 were completely filled.

It may be observed that the nanochannels 104 are slightly tilted relative to the applied field, the direction of the nanochannels 104 may be observed by the bright lines to the left of the first barrier (the bright spots in a line just left of center). The electric field direction is given by a line connecting the dots at the three consecutive barriers. This change in direction confirms that some of the transport is on top of the chip and some is sterically confined in the nanochannels 104.

Figure 19A:
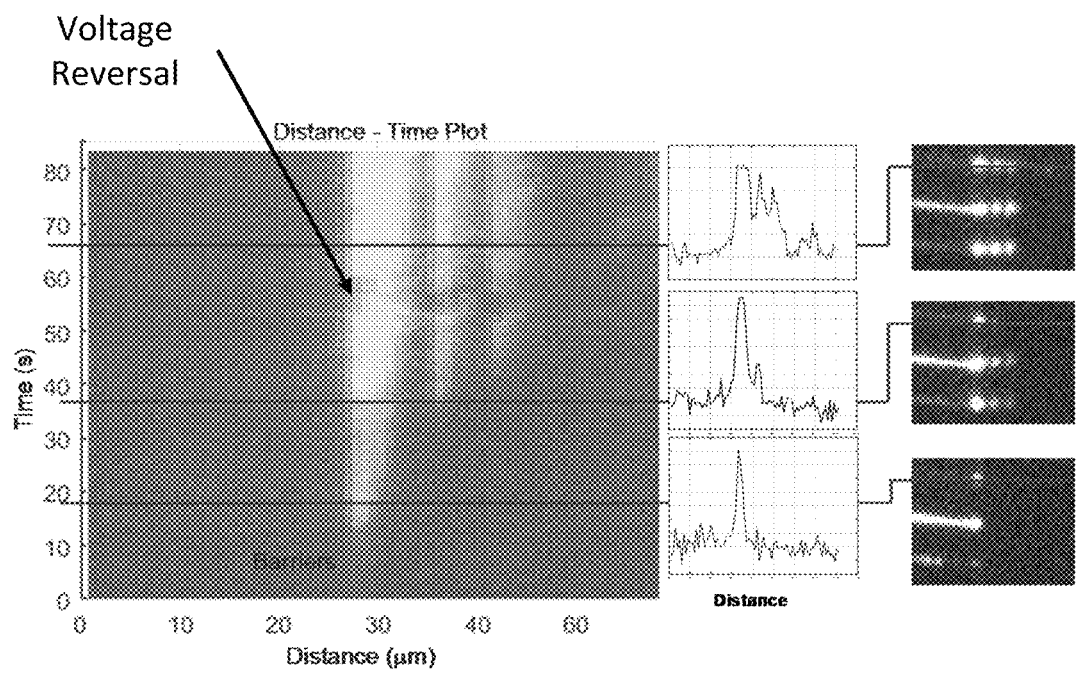
FIG. 19A is a false color, time-distance sequence showing the movement of DNA molecules in a nanochannel chip, according to various embodiments of the present disclosure. Time-distance map is on the left, the line graphs in the center are scans of a specific horizontal line of the images and the images on the right are the corresponding images.

FIG. 19A shows a time history (vertical axis) vs. distance along the nanochannel chip 120 for a single horizontal line of the frame of the recorded movie from which the image shown in FIG. 18 was taken. The intensity of the fluorescence signal is indicated by a false color (the yellow regions). Note that it takes ~16 sec from the appearance of the fluorescence at the first barrier until it appears on the second barrier. This can be taken as an indirect measurement of the 48,000-base-long, λ-phage, dsDNA transit time through the tortuous nanopore, demonstrating that the tortuous nanopore significantly slows the DNA transit compared with a simple thin-film nanopore where transit times are typically 1 base/μsec (or ~50 msec for λ-phage DNA).

The applied field was reversed for a short time (labeled on FIG. 19A) to demonstrate that the direction of DNA transport can be reversed with an applied field. This is shown in more detail in FIG. 20, taken using a higher magnification 60× objective, where the DNA fluorescence was recorded during several field reversals.

Figure 20:
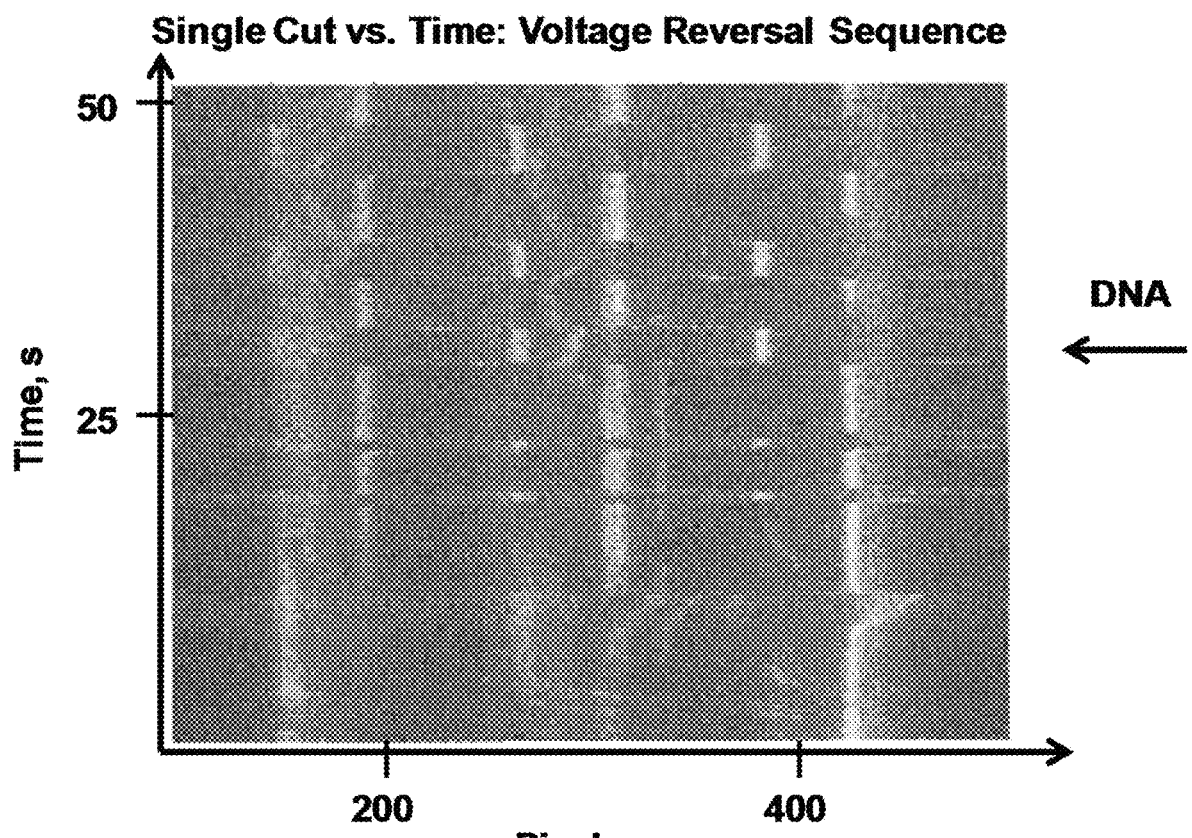
FIG. 20 is a similar false color representation of a film sequence showing multiple electric field reversals.

For these results, a 70 V potential was applied to electrodes separated by about one (1) cm placed in wells 108, 109 etched at opposite ends of the nanochannel chip 120. The electric field experienced by the DNA in the interior region of the nanochannel chip 120 is time dependent and is a function of both the applied voltage and the screening of the local field by the motion of free charges in the solution. This screening may be observed as a reduction in the motion of the DNA from the initial application of the voltage as the ions in the solution move to reduce the field in the interior regions of the nanochannels. This screening is a function of the concentrations of mobile ions (dissociated salts and hydrogen ions). The present experiments were conducted at close to neutral pH and with low salt concentration (0.01× TBE solution) to minimize these screening effects. FIG. 20 shows DNA accumulation on the barriers due to applying a negative potential to the well with DNA. Switching the polarity and/or slowly increasing the electric field about 10 seconds after the beginning of the experiment results in DNA movement in the opposite direction which was recorded during next 3 s. Each change of polarity from −70 to +70 and vice versa causes DNA movement to opposite barrier and accumulation in less than ⅕ s.

The images of FIGS. 19A, 19B, 20, and 21 suggest that a sequence of pulses may be more effective for controlling the DNA motion than a continuously applied (DC) voltage. Additional electrodes can be placed on the nanoparticle roof 110 of the nanochannels 104 and on a cover 116 incorporated above the nanochannels 104 to provide additional control.

Figure 19B:
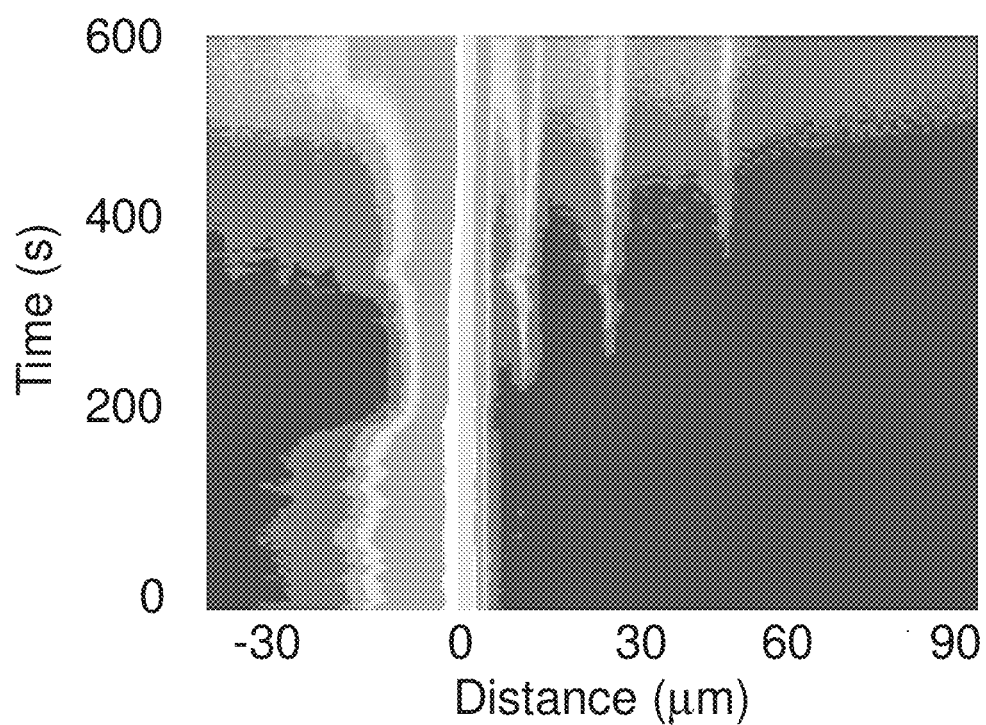
FIG. 19B shows a similar result to FIG. 19A, but with a chip with a 20 nm layer of CVD deposited SiO2 to reduce the tortuous nanopore density and average size. The time scale for the DNA to appear at the second barrier has been increased to ~200 sec.

As discussed above, various processes may be used to partially seal the tortuous nanopores 114 in the nanoparticle roof 110 to both reduce the density and to decrease the average size thereof. Both ALD and CVD have been demonstrated to successfully slow the DNA translocation through the tortuous nanopores. FIG. 19B shows a result similar to FIG. 19A, but for nanochannel chip 120 that has been treated with a $SiO_2$ chemical vapor deposited layer. The time scale for the dsDNA to transit the nanoparticle roof 110 and appear at the second barrier has been increased to about 200 sec. This nanochannel chip 120 had 5-mm wide barriers spaced at 10, 20, and 30 mm. The final barrier was 30 mm wide.

Figure 21:
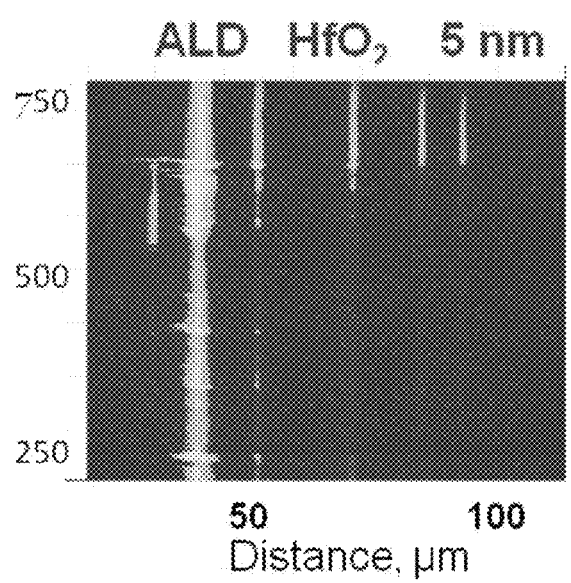
FIG. 21 is a similar false color representation of a film sequence for a chip that has been coated with ~5 nm $HfO_2$ using an ALD process. The time scale for the DNA to appear at the second barrier has been increased to ~600 sec.

FIG. 21 is a similar measurement made on a chip with 5 nm $HfO_2$ atomic layer deposition throughout the roof and the barriers. The time scale for the dsDNA to appear at the second barrier has been increased to over 600 s. This is adequate for Raman studies assuming a ⅓₀ s integration time for each base. Clearly by combining both ALD and CVD approaches, it is possible to tune the dsDNA translocation time over a wide range, suitable for measurements.

Figure 22:
FIG. 22 shows top down views of fluorescence from DNA molecules as they move across a series of barriers under the influence of an applied electric field. The barriers are separated from left to right by 10-, 20- and 30 micrometers. The first three barriers are five micrometers thick while the fourth barrier is 30 micrometers thick. Panel a illustrates λ-dsDNA stained with YOYO intercalated dye and panel b illustrates exonuclease produced λ-ssDNA stained with Oli-Green.
Figure 22:
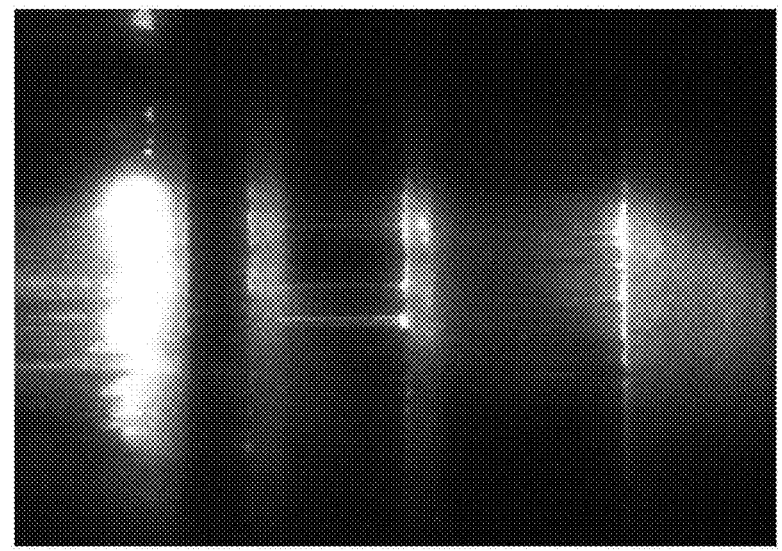

FIG. 22 shows top down measurements of fluorescence from dsDNA with intercalated YOYO dye (panel a) and from exonuclease-produced ssDNA with an OliGreen fluorophore (panel b). In both cases, the DNA has moved through and over the barriers under an applied electric field as described for FIGS. 18, 19A, 19B, 20, and 21. For this set of experiments, the barriers were separated (from left to right) by 10-, 20- and 30-micrometers and the first three barriers were 5 micrometers wide while the last barrier is 30-micrometers wide. This demonstrates that the transport is similar for both dsDNA and ssDNA.

Tethered Samples

Figures 23A, 23B, 23C:
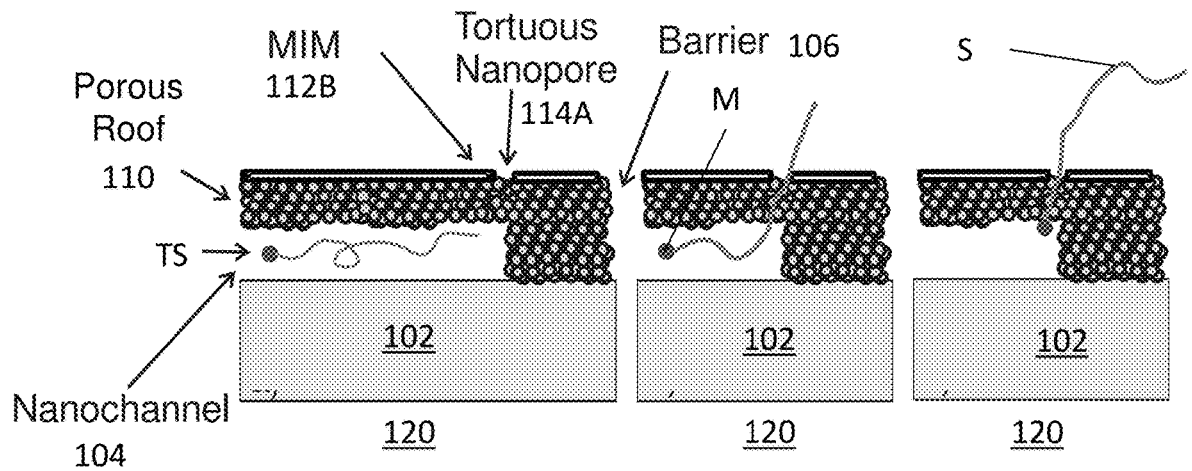

FIGS. 23A-23C illustrate successive stages of a tethered sample TS nanochannel chip detection method, according to various embodiments of the present disclosure. Referring to FIGS. 23A-23C, tethered samples TS may include nucleic acid sample molecules S that are modified to include a tethering moiety M. For example, the tethered samples TS may include dsDNA or ssDNA sample molecules S bonded to tethering moieties M configured to control the movement of the tethered samples TS through a nanochannel chip 120, due to the tethering moieties M having a particle size that is greater than the width of the nucleic acid sample molecules S. In particular, the particle size of the tethering moieties M may be selected to be small enough to pass through the nanochannels 104 of the chip 120, which may have widths ranging from about 100 nm to about 500 nm, and at the same time large enough to prevent the tethering moieties M from passing the nanopores 114, which may have diameters ranging from about 0.5 nm to about 5 nm. For example, the tethering moieties M may have diameters that range from about 10 nm to about 80 nm, such as from about 20 nm to about 70 nm, or from about 30 nm to about 60 nm, or about 50 nm.

For example, the tethering moieties M may include a semiconductor nanostructures such as quantum dots, metallic nanoparticles (e.g., Au or Ag), and/or a relatively large molecules such as Fullerenes. In some embodiments, the tethering moieties M may be attached to either the 5' end or the 3' end of a sample nucleic acid molecule, depending on the attachment mechanism used to attach the tethering moiety. Accordingly, the tethered samples TS may be referred to as having a "free end" that is not attached to a tethering moiety M and a "tethered end" which is attached to a tethering moiety M.

The tethering moieties may be attached to ends of ssDNA sample molecules S via ligation. For example, DNA-modifications/attachments can be achieved by ligating the end of the Lambda DNA to a biotinylated DNA fragment, complementary to one of the Lambda "sticky", unpaired 12-nucleotide-long ends. Commercially available gold or silver nanoparticles, quantum dots or fullerenes modified with streptavidin provide a very strong bond between the ssDNA and the tethering moiety.

Referring to FIG. 23A, the method may include loading the tethered samples TS into the nanochannel 104 of a nanochannel chip 120. An electric field may be applied to drive the tethered samples TS towards a barrier 106.

As shown in FIG. 23B, the free end of a tethered sample TS may enter a nanopore 114A adjacent to the barrier 106, before emerging from the roof 110 through an opening in the electromagnetic-field enhancement structure 112B. As the sample molecule S of the tethered sample TS emerges from the roof 110, the base sequence thereof may be optically detected, based on Raman spectral detection methods as described herein.

As shown in FIG. 23C, the tethering moiety M reaches the roof 110 and is prevented from entering the smaller nanopore 114A, such that the tethered sample TS becomes fixed in place by the blocked tethering moiety M. Continued application of the electric field may result in stretching of the sample molecule S. The method may also include changing the polarity of the applied electric field, in order to reverse the movement direction of the tethered sample TS. In some embodiments, changing the polarity may allow for a partial sequencing or resequencing of the local base sequence of the sample TS, by moving different bases into a hotspot of the electromagnetic-field enhancement layer 112B.

Epigenetic Detection

Epigenetic changes modify the activation of certain genes, but not the genetic code sequence of DNA. The microstructure (not code) of DNA itself or the associated chromatin proteins may be modified, causing activation or silencing. Thus, epigenetic changes enable differentiated cells in a multicellular organism to express only the genes that are necessary for their own activity. Epigenetic changes are preserved when cells divide. Most epigenetic changes only occur within the course of one individual organism's lifetime; however, these epigenetic changes can be transmitted to the organism's offspring through a process called transgenerational epigenetic inheritance. Moreover, if gene inactivation occurs in a sperm or egg cell that results in fertilization, this epigenetic modification may also be transferred to the next generation.

DNA methylation is a type of epigenetic change whereby methyl groups are added to a DNA molecule. Methylation may change the activity of a DNA segment without changing its sequence (e.g., without changing the sequence of bases adenine (A), guanine (G) and thymine (T), cytosine (C)). When located in a gene promoter, DNA methylation typically acts to repress gene transcription. DNA methylation is essential for normal development and is associated with a number of key processes including genomic imprinting, X-chromosome inactivation, repression of transposable elements, aging, and carcinogenesis.

The methylation of cytosine to form 5-methylcytosine (5mC) has been found to be widespread in both eukaryotes (cellular organisms) and prokaryotes (noncellular organisms, such as bacteria), even though the rate of cytosine DNA methylation can differ greatly between species. Adenine methylation has also been observed in bacterial, plant, and recently in mammalian DNA, but has received considerably less attention.

Conventional methylation measurement techniques, such as the Illumina Process, determine methylation by: a) sequencing the DNA reading both C and 5mC as "C"; b) converting the C's to U's (uracil) using a bisulfite treatment of the original DNA sample that does not alter the 5mC's; and c) resequencing and noting the conversions. Accordingly, such processes do not allow for the direct detection of cytosine methylation.

In contrast, various embodiments disclosed herein provide methods of nucleotide sequencing that also provide for the direct detection of methylation locations, using a much simpler Raman spectra-based approach. In particular, Raman spectra provide unique identification of each base. This is true both for isolated bases and for bases of a ssDNA molecule.

Figure 24:
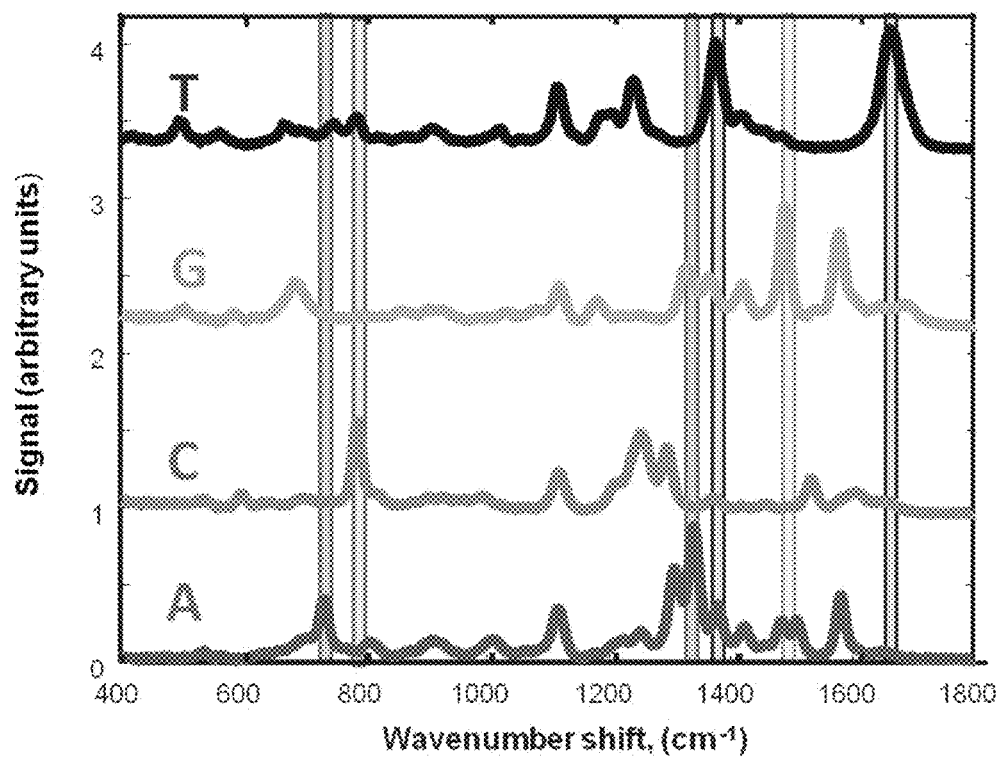
FIG. 24 is a spectral plot showing the Raman spectra of the deoxy-triphosphate forms of the DNA bases adenine, cytosine, guanine, and thymine, according to various embodiments of the present disclosure.

FIG. 24 shows Raman spectra for each of the tri-phosphate forms of the nucleotides: adenine (A), cytosine (C), guanine (G) and thymine (T). The vertical bands indicated on FIG. 24 show specific spectral features that can be used to uniquely identify each of the bases.

Before using these spectra to identify individual bases of ssDNA, it may be important to verify that these bands persist among various chemical forms of the molecules and as the bases are incorporated in a ssDNA oligonucleotide.

Figure 25:
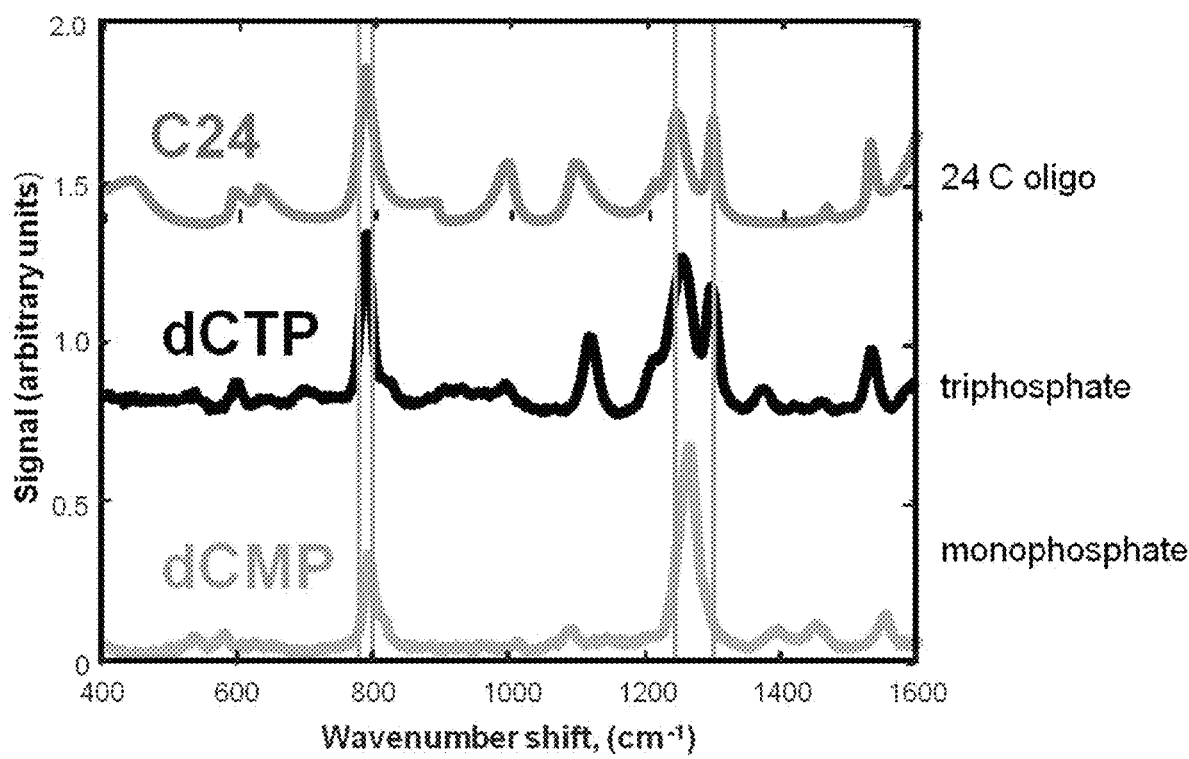
FIG. 25 is a Raman spectral plot showing a comparison of the Raman spectra of deoxy-monophosphate C; deoxy-triphosphate C, and a 24C oligonucleotide, according to various embodiments of the present disclosure.

FIG. 25 is a graph showing Raman spectra for three forms of cytosine: cytosine monophosphate (dCMP), cytosine triphosphate (dCTP), and 24-base synthetic cytosine oligonucleotide (C24). As shown in FIG. 25, the monophosphate exhibits two strong peaks, one at 789 $cm^{-1}$ and a second at about 1263 $cm^{-1}$. The 789 $cm^{-1}$ band persists across all three molecular variants. The 1263 $cm^{-1}$ band splits into two distinct peaks at 1244 $cm^{-1}$ and 1297 $cm^{-1}$ as well as an unresolved shoulder at about 1220 $cm^{-1}$ in the triphosphate and oligonucleotide. Additional peaks appear at about 1100 $cm^{-1}$ and 1550 $cm^{-1}$ in both the triphosphate and the oligonucleotide that are assigned to the phosphate backbone.

Figure 26:
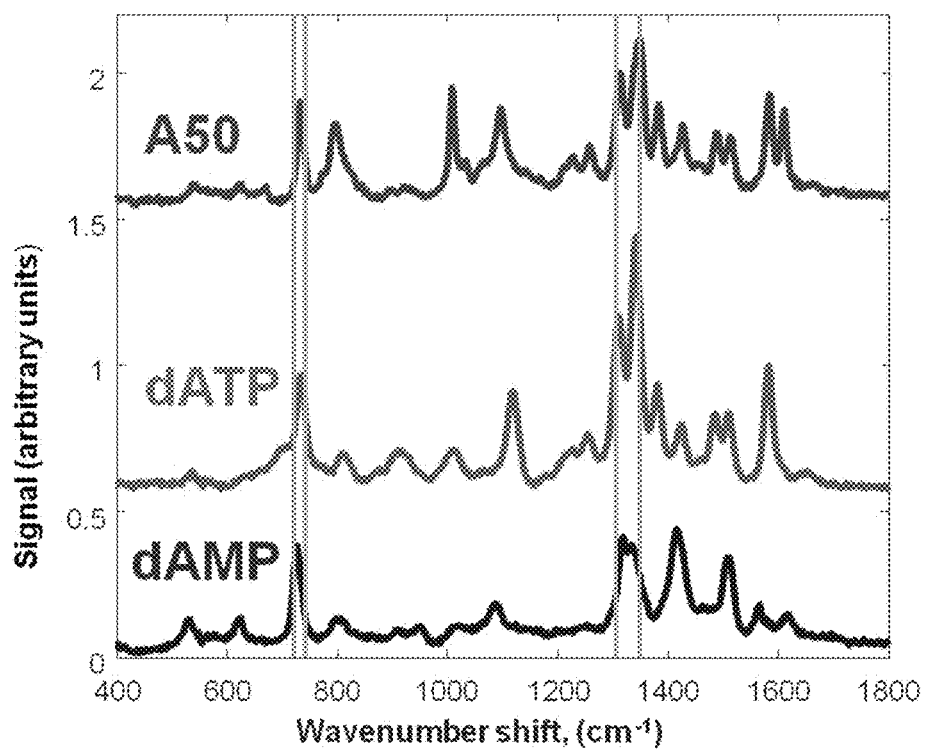
FIG. 26 is a Raman spectral plot showing a comparison of the Raman spectra of deoxy-monophosphate adenine, deoxy-triphosphate adenine, and a 50 adenine oligonucleotide, according to various embodiments of the present disclosure.
Figure 27:
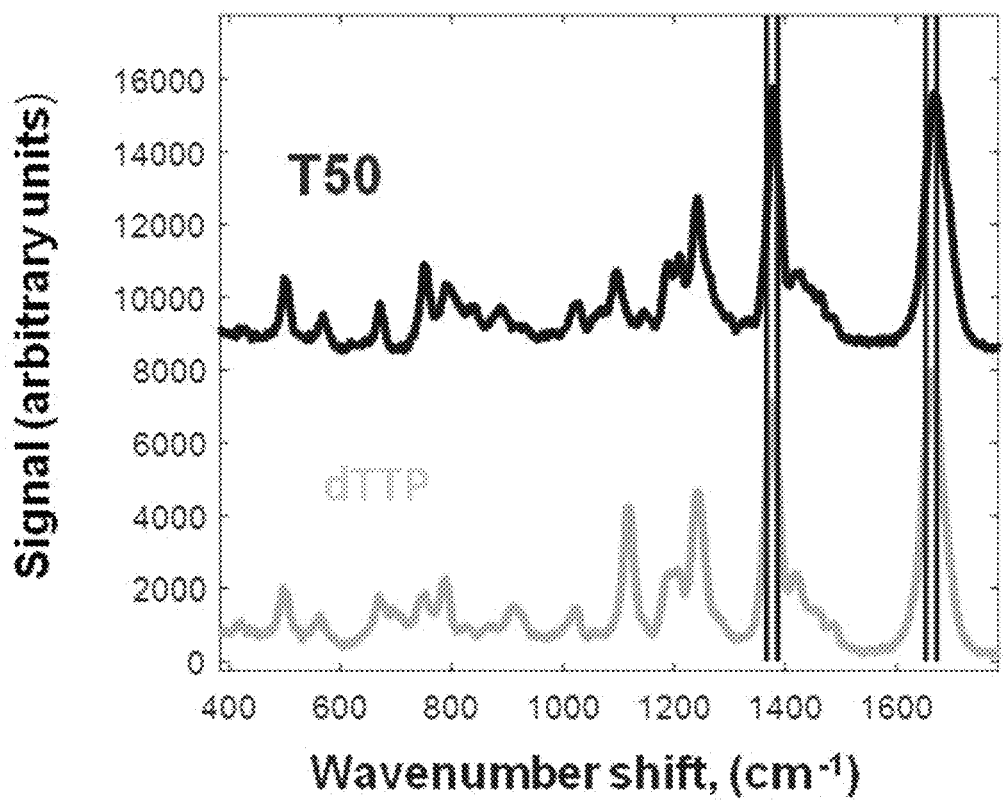
FIG. 27 is a Raman spectral plot showing a comparison of the Raman spectra deoxy-triphosphate thymine and a 50 thymine oligonucleotide, according to various embodiments of the present disclosure

FIG. 26 is a graph showing Raman spectra for three forms of adenine: adenine monophosphate (dAMP), adenine tri-phosphate (dATP), and a 50 base synthetic adenine oligonucleotide (A50). FIG. 27 is a graph showing Raman spectra for two forms of thymine: thymine tri-phosphate (dTTP), and a 50 base synthetic thymine oligonucleotide (T50). As shown in FIGS. 26 and 27, the different forms of adenine and thymine provide similar Raman spectra results.

The spectra become more complex as the additional atoms are added, but the characteristic features are retained. Long chains of guanine fold into secondary structures and precipitate from solution and no spectra beyond the tri-phosphate were obtained. However, as shown below the characteristic guanine features are retained in oligonucleotides that combine guanine with other bases.

Figure 28:
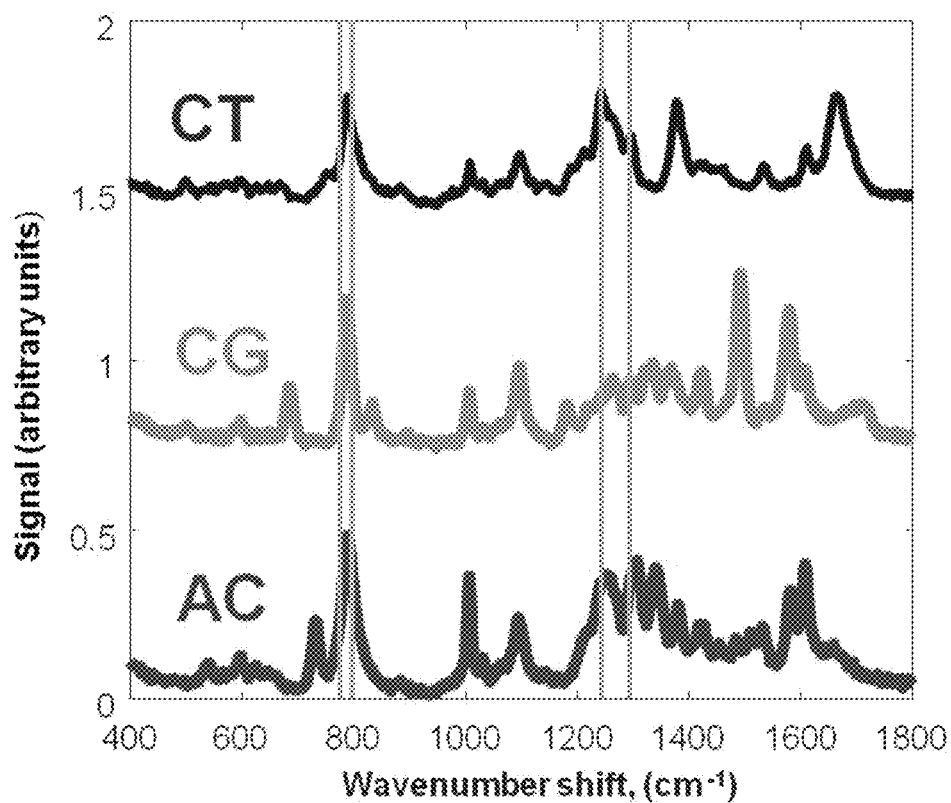
FIG. 28 is a Raman spectral plot showing a comparison of the Raman spectra of oligonucleotides consisting of alternating chains of AC, CG, and CT, showing that the characteristic peaks associated with the cytosine persist in all of the spectra.

The next step in complexity is to examine the Raman spectra of oligonucleotides with more than one nucleotide. FIG. 28 is a graph showing the Raman spectra of 20 base oligonucleotides of cytosine alternating with thymine (CT), guanine (CT), and adenine (CG). As shown in FIG. 28, the peak at 789 cm$^{-1}$ is consistently observed. The peaks around 1244 cm$^{-1}$ are present in all of the spectra, but are less pronounced for the CG oligonucleotide.

Figure 29:
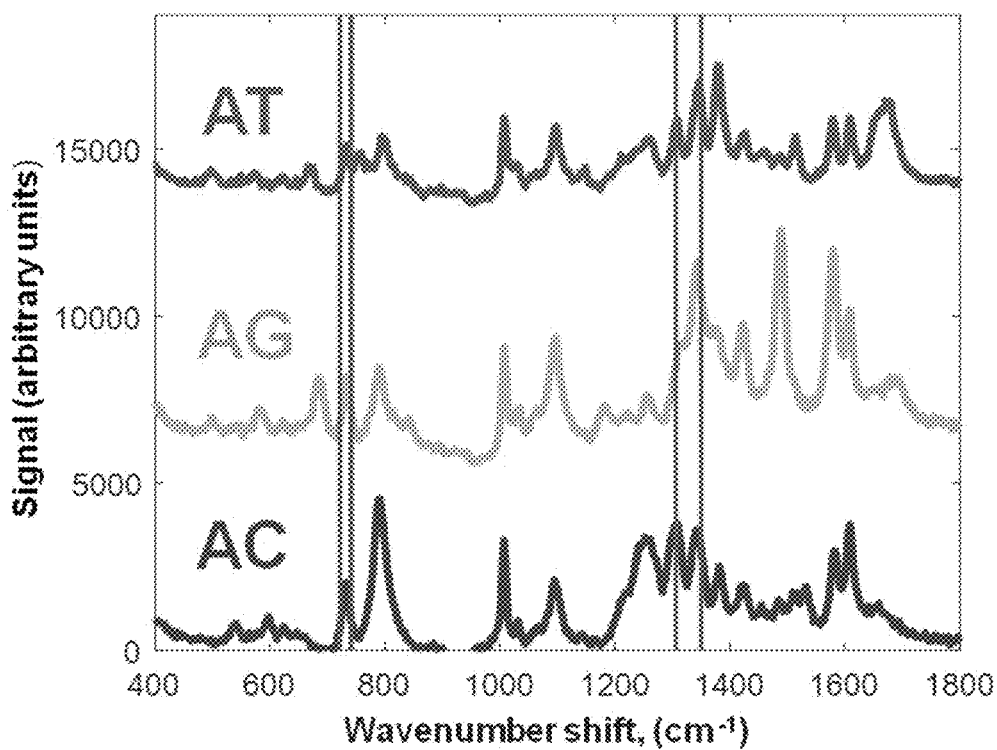
FIG. 29 is a Raman spectral plot showing a comparison of the Raman spectra of oligonucleotides consisting of alternating chains of AC, AG, and AT, showing that the characteristic peaks associated with the adenine persist in all of the spectra.
Figure 30:
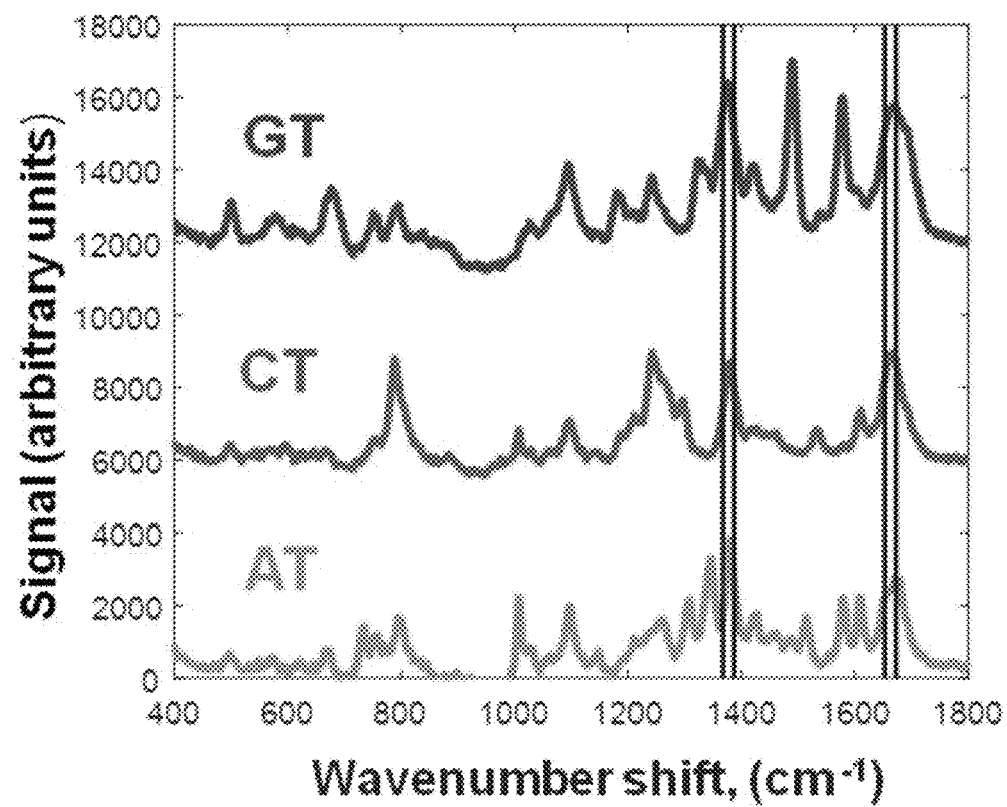
FIG. 30 is a Raman spectral plot showing a comparison of the Raman spectra of oligonucleotides consisting of alternating chains of AT, CT, and GT, showing that the characteristic peaks associated with the thymine persist in all of the spectra.
Figure 31:
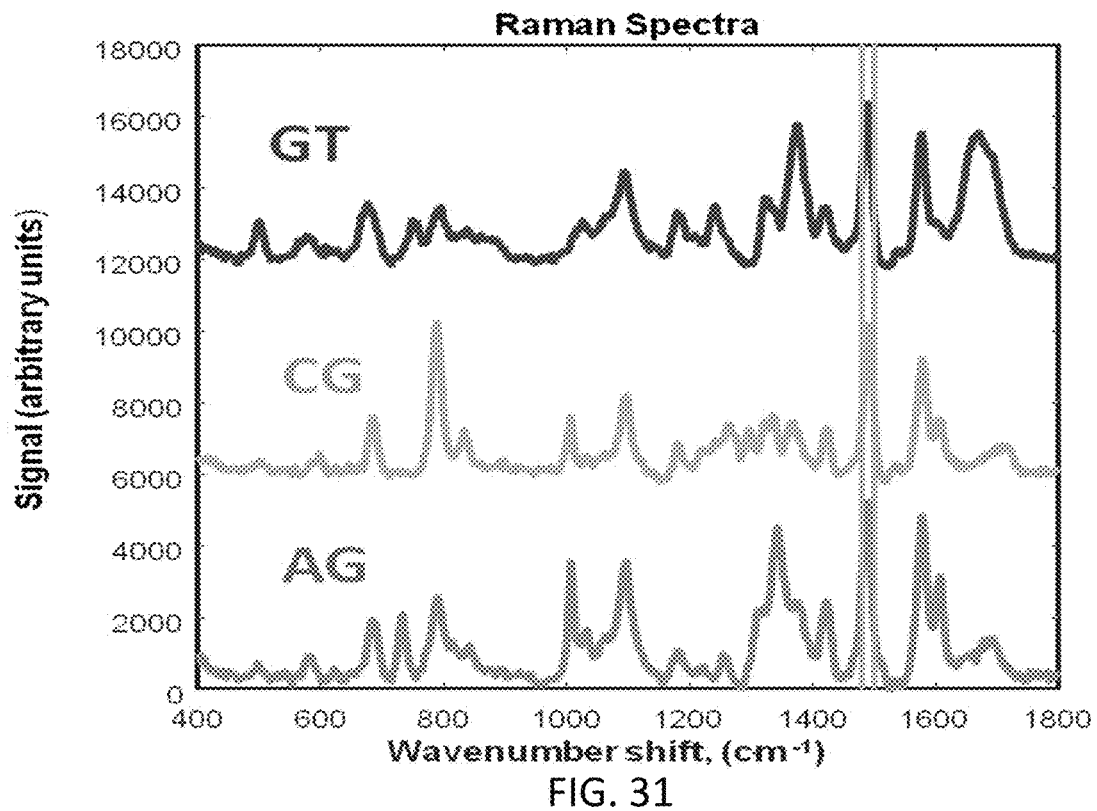
FIG. 31 is a Raman spectral plot showing a comparison of the Raman spectra of oligonucleotides consisting of alternating chains of AG, CG, and GT, showing that the characteristic peaks associated with the guanine persist in all of the spectra.

FIG. 29, FIG. 30, and FIG. 31 are graphs showing similar results for 48 base oligonucleotides of adenine, thymine, and guanine, respectively, in alternating arrangement with each of the other bases. As shown in FIG. 29, the adenine low-frequency peak at about 733 cm$^{-1}$ persists through all of the chains. The higher frequency bands near 1312- to 1345 cm$^{-1}$ are present with varying intensities in each of the cytosine containing oligonucleotide spectra.

As shown in FIG. 30, the thymine-containing oligonucleotides show persistent peaks at 1378 cm$^{-1}$ and 1672 cm$^{-1}$. As shown in FIG. 31, the guanine oligonucleotides all show a peak at around 1480 cm$^{-1}$.

The Raman spectra provide a vast amount of information on the local DNA sequence. Not only are the individual bases indicated by specific peaks, but adjacent bases may in some cases change the locations of the peaks and/or give rise to new peaks.

Figure 32:
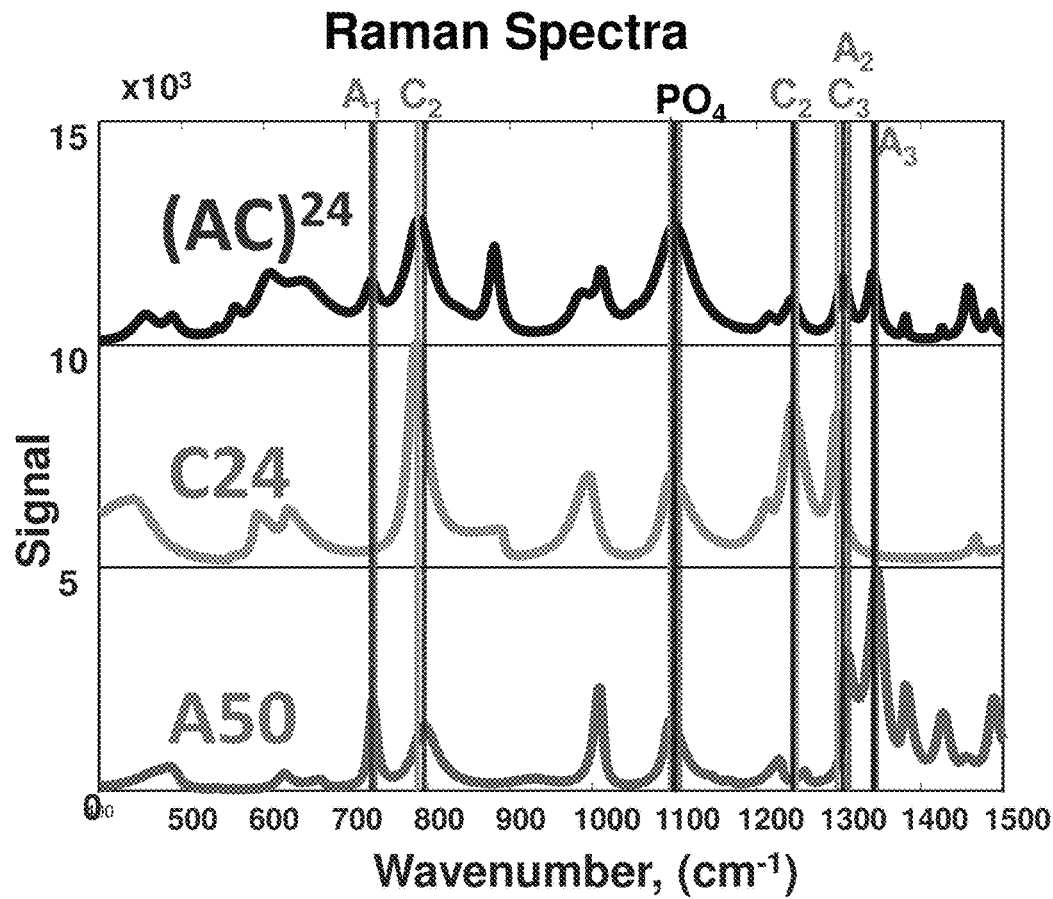
FIG. 32 is a Raman spectral plot showing a comparison of the Raman spectra of a 50A chain, a 24C chain, and an alternating $(AC)^{24}$ oligonucleotide.

FIG. 32 is a graph showing Raman spectra from three oligonucleotides: a 50 base adenine oligonucleotide (A50), a 24 base cytosine oligonucleotide (C24), and a 48 base oligonucleotide of alternating adenine and cytosine (AC)$^{24}$. As shown in FIG. 32, there are peaks associated with A and C bases in the respective spectra.

Figure 33:
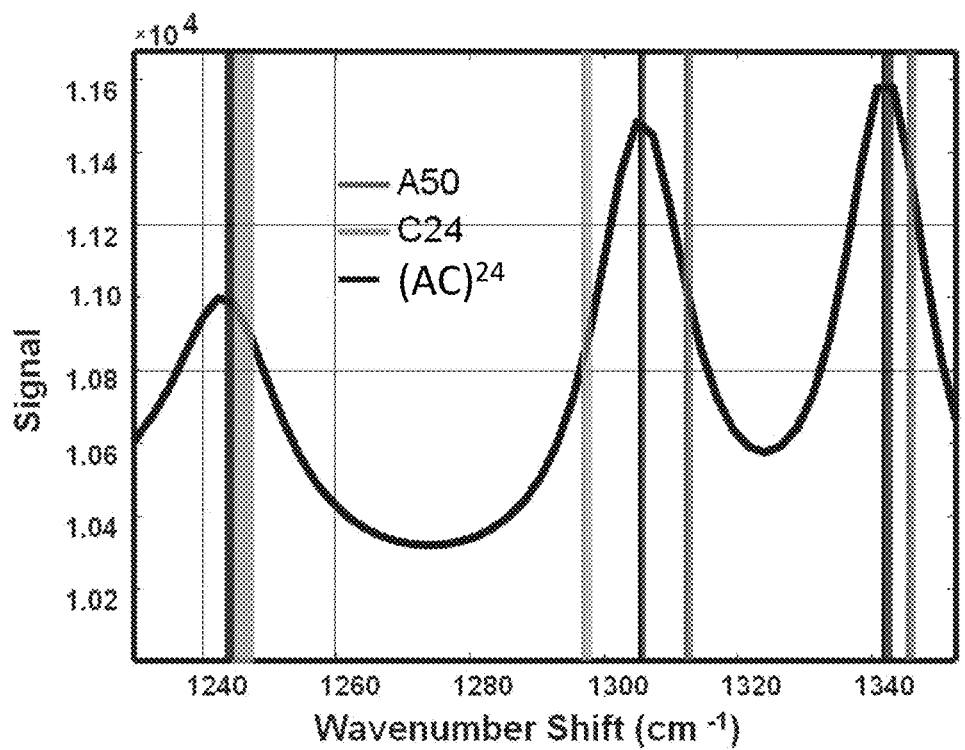
FIG. 33 is an expanded view of a section of FIG. 31 showing the peak frequencies measured on the 50A and 24C chains as well as the Raman spectral data for the $(AC)^{24}$ oligonucleotide. The 1240 $cm^{-1}$ peak is slightly shifted in the combined nucleotide. More significantly, the 1300 $cm^{-1}$ peak is shifted to an average shift from the value observed in the 50A and 24C oligonucleotides.

FIG. 33 is a graph showing an expanded view of the (AC)$^{24}$ spectrum in the region from 1235- to 1345 cm$^{-1}$ shift. As shown in FIG. 33, the peak at a 1240 cm$^{-1}$ shift, which is associated with cytosine, is only slightly shifted from 1244 cm$^{-1}$ in the (AC)$^{24}$ spectrum. The peak shift at a 1305 cm$^{-1}$ may result from a combination of the 1295 cm$^{-1}$ cytosine peak and the 1310 cm$^{-1}$ adenine peak. There is a clear shift of the 1345 cm$^{-1}$ adenine peak to 1341 cm$^{-1}$ in the (AC)$^{24}$ chain. It should be noted that multiple repeat measurements of the same oligonucleotides result in a variation of only about 1 cm$^{-1}$. There are many other nearest neighbor correlations that impact the Raman spectra and can be used to improve the readout accuracy. A straightforward approach for recognizing these correlations is to use a chemometric spectral analysis. This approach uses the entire spectrum and finds correlations by training a processor using known spectra.

In contrast to the labor-intensive, time-consuming, and expensive conventional techniques for detecting cytosine methylation, Raman scattering provides a direct measurement of the methylation, since the Raman spectra for deoxy-C and deoxy-5mC are distinct and easily resolved. Other DNA modifications, resulting from DNA damage, also exhibit unique Raman signatures and therefore can be identified. This capability of distinguishing cytosine and 5-methyl-cytosine is not available with any current commercial approach to sequencing. Raman scattering also provides a direct, single-step chemical identification, using unprocessed cellular DNA, for distinguishing between C and 5-methyl-C based on the unique vibrational frequencies of the DNA base molecules.

Figure 34:
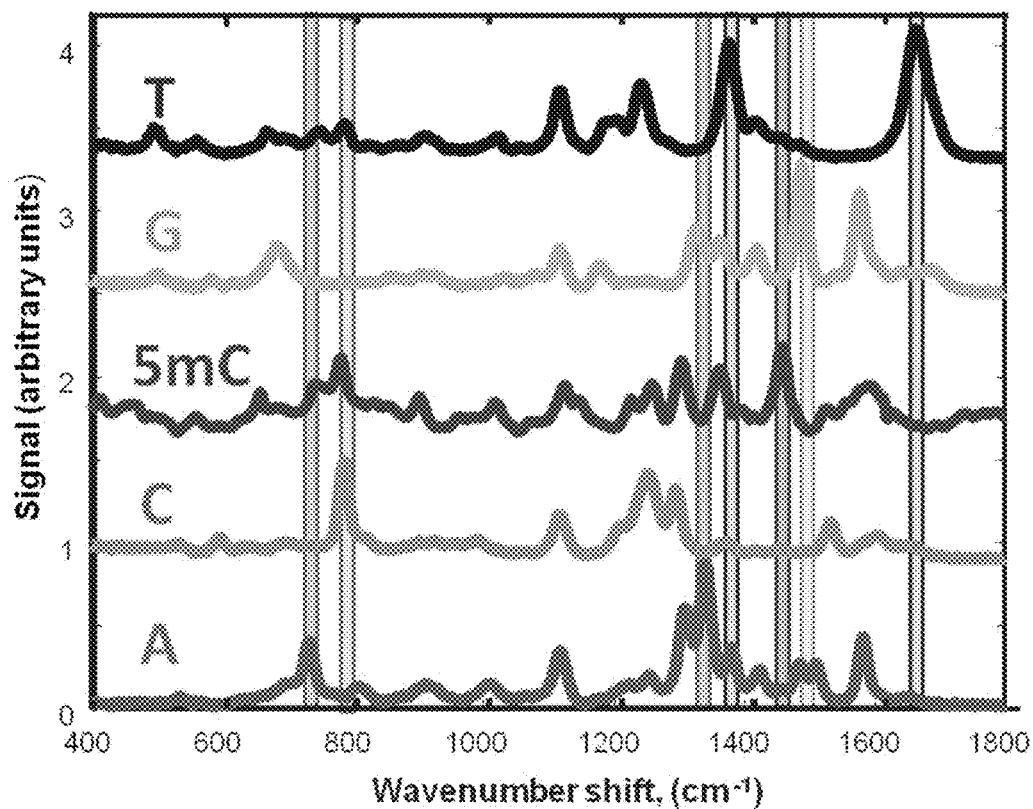
FIG. 34 is a repeat of FIG. 23 with the addition of the Raman spectral signature of deoxy-triphosphate-5-methyl-cytosine showing that its Raman signatures is easily distinguished from the Raman signatures of the bases A, C, G, and T.

This is shown in FIG. 34, which includes the spectral data of FIG. 24, with the addition of the 5methyl-cytosine Raman spectra. An additional peak at about 1430 cm$^{-1}$ has been indicated as a marker for 5-methyl-cytosine. However, as discussed above a full spectrum approach would provide an improvement in accuracy over monitoring individual peaks, particularly in the presence of non-resonant backgrounds arising from scattering and from broadband Raman scattering from the buffer solution and from the glass of the substrate and the porous material forming the walls and roof. By subjecting the sample DNA strands to a full or broader spectrum light source 162 (FIG. 11B), a characteristic peak may present itself during analysis to allow an observer to identify the presence of the methylated cytosine. In many conventional technologies a narrower spectrum of light may be employed. Consequently, certain characteristic peaks may not be revealed during the spectrum analysis. Thus, methylated bases may go undetected in conventional technologies. The various embodiments disclosed herein seek to perform a full spectrum analysis that may reveal the presence of methylated bases.

Figure 35:
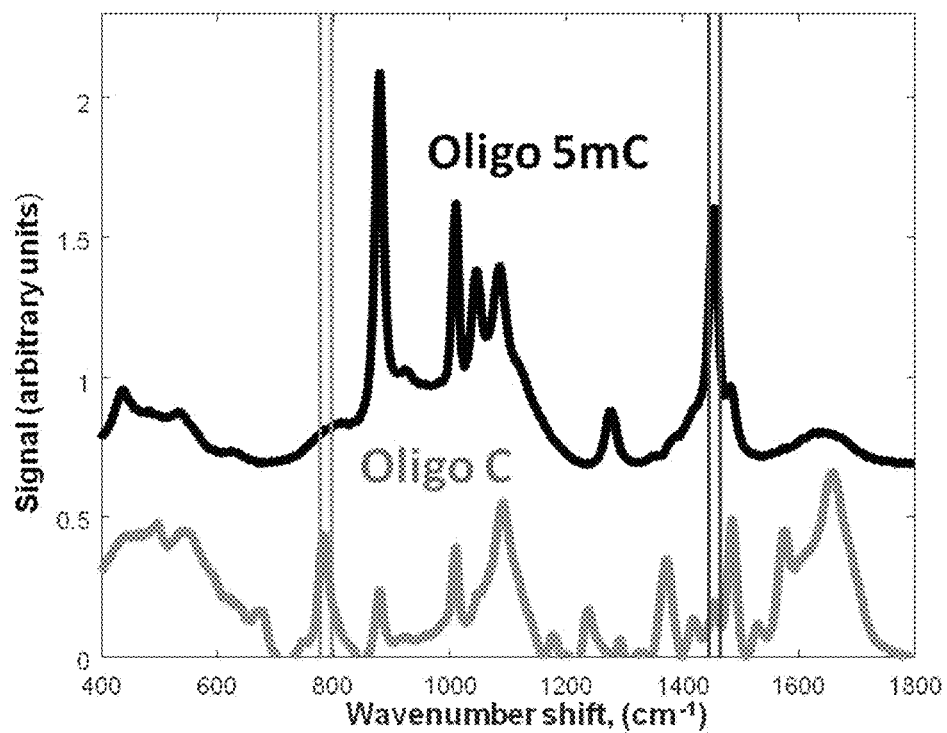
FIG. 35 shows that the Raman spectral plot of an oligonucleotide containing 5-methyl-C is easily distinguished from an identical oligonucleotide where all of the 5-methyl-C bases are replaced with unmethylated cytosine.

FIG. 35 is a graph showing a comparison of Raman Spectra of 22 base DNA oligomers containing 5-methyl-cytosine (Oligo 5mC) and un-methylated cytosine (Oligo C), in the same sequence (TC*G-TTC*-GTT-C*GT-C*TC*-GTC*-TC*GT, where the C* represents cytosine or 5-methyl-cytosine in identical sequences). As shown in FIG. 35, 5-methyl-cytosine spectral peaks are also preserved in complex oligonucleotides, and the distinctions between the deoxy-C-triphosphate and deoxy-5-methyl-C-triphosphate monomers are clearly evident. In particular, the deoxy-5-methyl-C triphosphate monomer has a strong feature at about 1430 cm$^{-1}$ that is absent for the deoxy-C triphosphate.

Accordingly, various embodiments provide methods of nucleotide sequencing that include the detection of methylated bases. In particular, the methods may include using a sequencing system including a nanochannel chip as described above, to identify the Raman spectra of each base of a sample nucleotide. The detected Raman spectra for each base may range from about wavenumber 400 cm$^{-1}$ to about 1800 cm$^{-1}$ and may be referred to herein as a "full Raman spectra".

Based on the full Raman spectra of each base, the method may include determining the base sequence of a sample nucleotide and may also include determining whether bases such as cytosine and adenine are methylated or un-methylated. The full Raman spectra may also be analyzed to determine whether the detected base sequence is accurate. In particular, spectral peaks know to be affected by adjacent bases may be analyzed and compared to the detected bases of adjacent nucleotides.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

EXAMPLE(S)

The following description provides details and results of a study concerning a comparative analysis of several approaches to introduce long single-stranded DNA (ssDNA) molecules into nanochannels of a nanochannel chip consistent with the present disclosure, as well as a description of ssDNA behavior in ~300×500 nm² cross-section nanochannels with porous roofs. The study was performed to demonstrate that the initial extension of ssDNA molecules depends on the methods of preparation and on introduction into the nanochannels, as well as further demonstrate that it is possible to manipulate DNA in the nanochannels in situ, by adding reagents through the porous roof, as will be described in greater detail herein.

Single-molecule ssDNA analysis is essential for the precise sequencing and mapping technologies that are currently under intensive development. Nanometer-scale structures, in turn, play an important role in many single-molecule manipulations. The ability to separate, stretch and visualize long single DNA molecules within nanochannels is essential for many applications ranging from DNA imaging and sequencing to the detection of new microorganisms. There is a large body of research on the behavior of long dsDNA molecules in nanochannels. dsDNA has been stretched and measured, manipulated with an applied electric field and its behavior explained and correlated with polymer physics models. Single DNA molecules had been visualized using scanning and transmission electron microscopy and high-resolution fluorescence microscopy. Much less information has been accumulated on single ssDNA molecular behavior on a surface or in nanochannels, even though it is, in fact, ssDNA that is required in the vast majority of sequencing applications. There are several reasons why studying ssDNA, and particularly long ssDNA is more difficult compared to duplex, dsDNA studies.

While there are a number of fluorescent dyes that strongly bind to dsDNA, with high fluorescence quantum yield and good photostability, the selection of readily available dyes is rather scarce for ssDNA. In addition, the higher flexibility of ssDNA leads to an ease of self-pairing within a long molecule, resulting in the formation of tangled, balled-up conformations that may complicate entrance into nanochannels and DNA stretching. In fact, special techniques involving coating ssDNA with a special polypeptide polymer sometimes have been used to prevent this self-pairing.

In this study, several approaches to introduce long ssDNA in nanochannels using λ-dsDNA as the DNA source. The λ-dsDNA is introduced into the nanochannels of a nanochannel chip with ordered nanochannel arrays as previously described herein, including nanochannels with a porous roof. The porous roof allows manipulation of DNA in situ, by adding buffers, enzymes, small oligos, or other reagents through the roof.

1. Nanochannel Chips Fabrication and Description

The study utilized nanochannel chips consistent with the present disclosure, including nanochannel chips fabricated in accordance with methods previously described herein. In brief, interferometric lithography may be used to define parallel lines of photoresist at a ~1 μm pitch on a silicon or silica substrate. Fabrication may further involve multiple spin coatings of ~single monolayers of nominally 50-nm diameter colloidal silica nanoparticles on the nanopatterned photoresist surface, which results in formation of porous walls and roofs over the nanochannels. The nanoparticles essentially "stack up" between the photoresist pattern features and ultimately form the walls and roof enclosing the resist lines. After the nanoparticles have been deposited, a 800° C. calcination step (air ambient) may be performed to remove the photoresist and sinter the nanoparticles. In turn, tortuous (convoluted and extended) nanopores extending through the ceiling of the nanochannels may self-assemble in this process. Finally, wells (ports) are etched at both ends of the nanochannel array by reactive ion etching (locally removing the roof and most of the nanochannel walls) to facilitate DNA solution penetration into the channels.

2. Preparation of Double-Stranded Lambda DNA (λ-dsDNA)

λ-dsDNA (48.5 kpb, stock concentration 500 μg/ml) was purchased from New England Biolabs. The DNA solution was diluted to 5 μg/ml in 0.01×Tris-EDTA (TE) buffer (1:100 dilution from 1×TE buffer (Sigma) to "0.01×TE", and was used for all the experiments included in this study described herein. The final solution was at pH ~8 with a NaCl concentration of ~1 mM. The 1 mM YOYO-1 dye (Molecular Probes) was diluted in 0.01×TE buffer and used at a ratio of 1 molecule per 8 base pairs for labeling λ-dsDNA.

3. Preparation of Single-Stranded Lambda DNA (λ-ssDNA)

λ-ssDNA was prepared by either heating and snap-cooling, or by Lambda Exonuclease digestion of λ-dsDNA.

a. Heating and Snap Cooling of λ-dsDNA

Heat-denatured and snap-cooled ssDNA was prepared either: a) in bulk/ex situ (heated and cooled in a tube and then loaded onto the chip); or b) heated and snap-cooled after introduction into the nanochannels (in situ).

For the ex situ preparation, 100 μl of 5 ng/μl λ-dsDNA solution was heated at 95° C. for 10 min to induce duplex melting and strand separation, and snap cooled on ice water for 2 min to avoid duplex renaturation. Quant-iT™ OliGreen™ ssDNA fluorescent dye (Molecular Probes) was used to stain ssDNA. An aqueous working solution of the OliGreen reagent was prepared by making a 200-fold dilution of the concentrated stock solution (concentration of the stock, in DMSO, was not disclosed by the manufacturer) in 0.01×TE buffer pH 8.0. The λ-ssDNA solution with OliGreen was incubated at room temperature for 1-hour and 1- to 2 μl of λ-ssDNA stained with OliGreen was introduced either through the chip roof, or through the wells at one side of the chip. Fluorescence images were taken using an Olympus Prior microscope at 60× magnification. The approximately 200×200 μm field of vision contains about 150-200 parallel nanochannels.

For the in situ preparation and staining of λ-ssDNA, first 1- to 2 μl of 5-ng/μl λ-dsDNA was introduced through the roof of the nanochannels, and the chip was heated at 95° C. for 10 min covered with 0.01×TE buffer. After 10 min, the chip was quickly transferred onto a pre-chilled to 0° C. Petri dish for snap-cooling for 2 min, washed once with 0.01×TE buffer and stained with OliGreen or YOYO-1 dye by incubation with the dye solutions for 1-hour at room temperature in the dark. After the incubation, the chip was washed with 0.01×TE buffer twice for 5 minutes to remove any excess dye.

b. Lambda Exonuclease Digestion of λ-dsDNA

Similar to the heating and snap cooling of λ-dsDNA, Lambda Exonuclease digestion to generate λ-ssDNA was also performed either ex situ or in situ.

For the ex situ digestion of λ-dsDNA by Lambda Exonuclease, 1 μl (5 U) of Lambda Exonuclease enzyme (New England Biolabs) was added to 2 μl of λ-dsDNA stock solution (1 μg) in a 20 μl 1× Exonuclease reaction buffer, and samples were incubated at 37° C. for 60 min. After incubation Exonuclease-digested sample was run through an Oligo-clean and Concentrator kit (Zymogen) following the manufacturers' protocol to remove the enzyme and monomer bases. Purified ssDNA was eluted in 20 μl 0.01×TE, and the DNA concentration was monitored with a Nanodrop 2000 Spectrophotometer. The ssDNA was diluted to 5 ng/μl with 0.01×TE and stained with OliGreen by incubation with the dye solution at room temperature in the dark for 1-hour. Exonuclease-digested, OliGreen-stained λ-ssDNA was introduced into the nanochannels through the roof or through the wells. As a control for completion of the digestion (absence of dsDNA), some samples were stained with YOYO-1, that is activated by intercalation into dsDNA and produces only a weak signal when bound to ssDNA.

For the in situ digestion of λ-dsDNA by Lambda Exonuclease, a 1 μl drop of DNA was loaded onto the roof and allowed to air-dry for 2-3 minutes. Once DNA entered the channels, 20 μl of Exonuclease reaction mixture containing 5 U of Lambda Exonuclease was added onto the chip surface where the DNA drop had been placed earlier. The chip was incubated at 37° C. for 60 min to allow the reaction to complete. Then the chip was heated at 75° C. for 10 min to inactivate the enzyme. A quick wash was done with 0.01×TE after deactivation. The chip was incubated with OliGreen dye in 0.01×TE for an hour at room temperature in the dark. Two 5 min washes were done to remove the excess dye, and the chip was stored in 0.01×TE buffer until imaged. Control experiments were done using YOYO-1 dye to check for the presence of undigested λ-dsDNA. In this case, instead of the OliGreen, after Exonuclease digestion the chip was stained with YOYO-1 dye for 1-hour at room temperature followed by washes.

c. Size Distribution Histograms

Fluorescence images of DNA molecules visualized by fluorescent dyes (YOYO-1 for ds-DNA and OliGreen for ssDNA) were taken with the emCCD camera and analyzed using the Software package CellSense (Olympus). About 100 molecules in multiple micrograph images were measured for each analysis. The exposure, gain, and other parameters of microscopy were kept constant across all images. Quantitation of stained DNA did not involve any background subtraction and raw images were directly used for quantification. The histograms show the number of molecules of a certain length in the analyzed population.

4. Introduction of λ-dsDNA and λ-ssDNA

λ-dsDNA or λ-ssDNA were introduced either through a well at one end of the chip or through the porous roof. DNA was allowed to migrate by capillary forces with default flow-rates, and without any external pressure or electric field. An additional 1-5 μl of 0.01×TBE was introduced after the introduction of the DNA to promote efficient capillary forces.

5. Formamide and Heat Denaturation

To induce separation of λ-DNA "sticky" protruding ends and prevent formation of dimers, either formamide at a 10% concentration or elevated nanochannel chip temperature were used. For ds-DNA 2 μl of formamide (stock 99.5%, Sigma) was added to 18 μl of YOYO-1 stained ds-DNA. 1-2 μl of this solution was introduced through wells from the side of the chip. Images were taken at 60× magnification. Formamide was found to interfere with OliGreen binding to ssDNA, so elevated temperature was used instead for the ssDNA experiments. λ-ssDNA stained with OliGreen was introduced either through the roof or through the wells from the side of the chip. The chip was transferred on to a small heat block (maintained at 45° C.), which was placed on the microscope stage below the objective. 0.01×TE buffer was added continuously to keep the chip from drying out. Images were taken at 60× magnification while the chip was on the heat block.

Results

1. λ-dsDNA in Nanochannels

At certain experimental conditions (ambient room temperature, low ionic strength (<1 mM Na$^+$ equivalent) λ-dsDNA spontaneously stretches in the nanochannels to almost full size. Capillary forces favor DNA entering the nanochannels with the liquid flow; however, the effective diameter of the Lambda-size (48,500 bp) statistical polymer coil is about 1 μm at physiological salt conditions, larger than the nanochannel dimension, and at low ionic strength used in the experiments it should be significantly larger because of the increase of DNA persistence length with a lower salt concentration. Thus, the entrance into nanochannels requires a certain degree of unfolding of the DNA "coil". In addition, the nanochannel walls are negatively charged and therefore add electrostatic repulsion to facilitate DNA unfolding and stretching. Further, at the low salt concentration of our 0.01×TBE solution, the double layer extends fully across the width of the nanochannel, forcing negative charged moieties, such as DNA, to the center of the channels.

Figure 36:
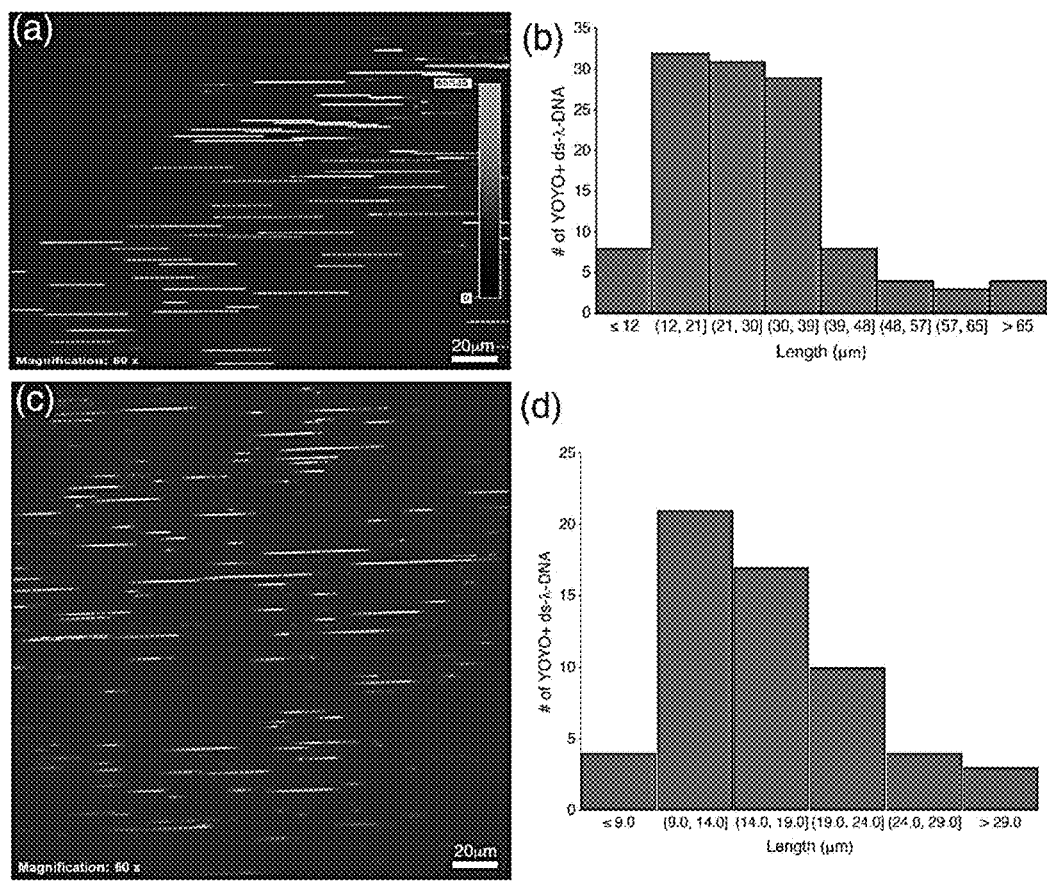
FIG. 36A shows results for YOYO-1-stained λ-dsDNA in the nanochannels and FIG. 36B shows a corresponding histogram illustrating a size distribution of the λ-dsDNA length relative to a number of measured molecules of a given size range.
FIG. 36C shows results for the YOYO-1-stained λ-dsDNA treated with 10% formamide to induce melting of the sticky ends and FIG. 36D shows a corresponding histogram illustrating a size distribution of the λ-dsDNA length relative to a number of measured molecules of a given size range and the effect of the 10% formamide treatment.

FIG. 36A shows a typical image of YOYO-1-stained λ-dsDNA in nanochannels, and FIG. 36B illustrates corresponding size histogram. In particular, FIG. 36A shows results for YOYO-1-stained λ-dsDNA in the nanochannels and FIG. 36B shows a corresponding histogram illustrating a size distribution of the λ-dsDNA length relative to a number of measured molecules of a given size range. FIG. 36C shows results for the YOYO-1-stained λ-dsDNA treated with 10% formamide to induce melting of the sticky ends and FIG. 36D shows a corresponding histogram illustrating a size distribution of the λ-dsDNA length relative to a number of measured molecules of a given size range and the effect of the 10% formamide treatment.

In all cases where individual micrographs are shown, the accompanying histograms are compiled from a number of micrographs to provide a more statistically appropriate number of molecules (~100 for each histogram).

FIG. 36A illustrates λ-dsDNA stained with YOYO-1 in the nanochannels and the histogram of FIG. 36B illustrates the size (length in μm) relative to a number of measured molecules of this size range. The calculated contour length of λ-dsDNA with intercalated YOYO-1 should be about 17 mm. While there are virtually no molecules shorter than 10, the majority of them are equally distributed in the range of 12- to 39-mm, that includes single molecules and dimers held together by the intermolecular hybridization of sticky ends.

FIG. 36C illustrates λ-dsDNA with 10% formamide treatment to induce melting of the sticky ends and the histogram of FIG. 35D shows the corresponding size distribution of dsDNA of FIG. 35C after addition of 10% formamide. In this case, the number of dimer-sized molecules is drastically reduced. Scale bars are 20 mm.

Lambda DNA sticky ends make it difficult to isolate and observe single molecules, so the population is often a mixture of monomers and dimers. At the relatively low concentration of DNA in our solutions, formation of higher-order multimers becomes highly unlikely, as is reflected in the virtual absence of molecules longer than approximate double-length >39 μm). To reduce the dimer formation, we have tried two approaches: adding a denaturing agent, formamide (10%), or increasing the chip temperature by placing it on a metal block heated by a low electric current to constant temperature of ~45° C. Both approaches were sufficient to induce melting of the 12-nucleotide long sticky ends, while keeping the dsDNA structure intact. FIGS. 36C and 36D show the effect of adding 10% formamide to dsDNA solution. The result, as the histogram on FIG. 36D shows, is the absence of dimer-length molecules; the maximum of the distribution lies below 19 μm, consistent with the prevalence of monomer molecules with various degrees of stretching.

2. λ-ssDNA in Nanochannels

Figure 6:
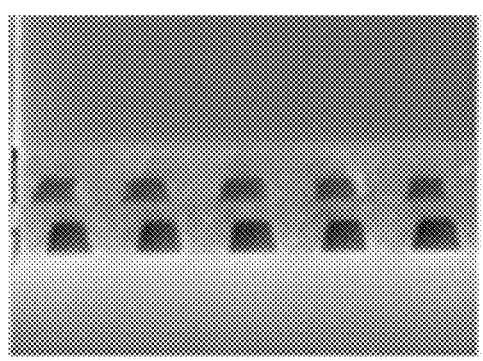
FIG. 6 is an SEM image showing a multi-layered nanochannel structure formed using the techniques described herein.
Figure 37:
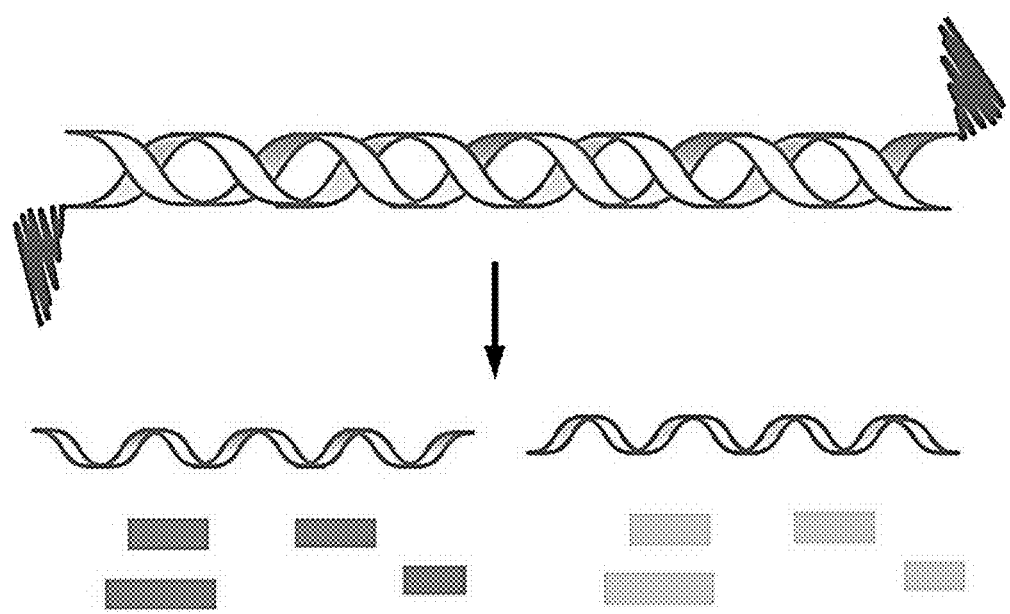
FIG. 37 illustrates a scheme of lambda exonuclease digestion of duplex DNA resulting in production of two non-complementary single strands of approximately half-size.

The ssDNA was prepared using two methods: 1) heat denaturation followed by quick cooling ("snap-cooling"); and 2) exonuclease digestion. While the snap-cooling method should provide full-length ssDNA (48.5 kb), exonuclease digestion results in approximately half-size molecules (24.3 kb) due to the fact that the enzyme acts from both 5' ends of dsDNA, and stops when the duplex no longer exists, i.e., both strands have been digested to a "meeting point" somewhere near the middle (FIG. 6). FIG. 37 illustrates a scheme of lambda exonuclease digestion of duplex DNA resulting in production of two non-complementary single strands of approximately half-size. The two methods of introducing the DNA into the nanochannels (through the side wells, or through the porous roof) were also compared.

a. Introducing ssDNA into Nanochannels Through the Wells

FIG. 38A shows results for OliGreen-dyed λ-ssDNA, which were prepared in bulk by heating and snap cooling λ-dsDNA, and introduced through the wells from the side of the chip into the nanochannels and FIG. 38B shows a corresponding histogram illustrating a size distribution of the λ-ssDNA length relative to a number of measured molecules of a given size range. FIG. 38C shows results for OliGreen-dyed λ-ssDNA, which were prepared by lambda exonuclease digestion, and introduced through the wells from the side of the chip into the nanochannels and FIG. 38D shows a corresponding histogram illustrating a size distribution of the λ-ssDNA length relative to a number of measured molecules of a given size range.

Figure 38:
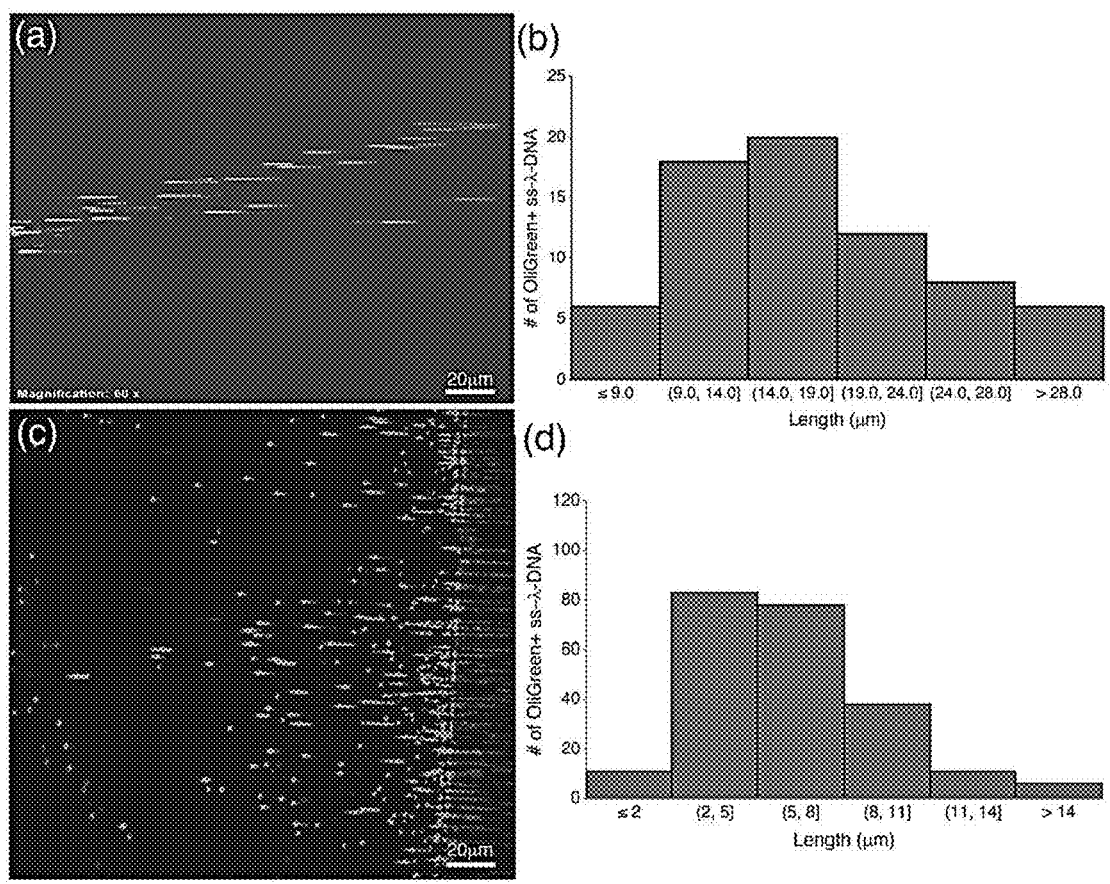
FIG. 38A shows results for OliGreen-dyed λ-ssDNA, which were prepared in bulk by heating and snap cooling λ-dsDNA, and introduced through the wells from the side of the chip into the nanochannels
FIG. 38B shows a corresponding histogram illustrating a size distribution of the λ-ssDNA length relative to a number of measured molecules of a given size range.
FIG. 38C shows results for OliGreen-dyed λ-ssDNA, which were prepared by lambda exonuclease digestion, and introduced through the wells from the side of the chip into the nanochannels
FIG. 38D shows a corresponding histogram illustrating a size distribution of the λ-ssDNA length relative to a number of measured molecules of a given size range.

FIG. 38 shows ssDNA generated by snap-cooling (FIG. 38A) and by Lambda Exonuclease digestion (FIG. 38C) introduced into the nanochannels through side wells. DNA was prepared ex situ and stained with OliGreen before being loaded into the wells. As a control for the full extent of DNA conversion from ds to ss form, Exonuclease-digested ssDNA was also stained with YOYO-1, specific for dsDNA (YOYO-1 needs to intercalate into dsDNA to produce high-intensity fluorescence), and no long dsDNA molecules were seen (data not shown); only some short "ball-like" fluorescent spots consistent with short self-paired dsDNA regions. Both snap-cooled and exonuclease-digested stretched linear molecules are clearly visible; the micrographs are shown at the same magnification, and the length difference is obvious, confirmed by the length histograms in panels FIGS. 38B and 38D. The average size in FIG. 38A is over 20 μm versus 2-8 μm in FIG. 38C, consistent with shorter molecules produced by Lambda Exonuclease digestion. The length of snap-cooled ssDNA is, in fact, longer than a full length of the parent λ-dsDNA molecule (about 17 μm), suggesting that, as in the case of λ-dsDNA some single-stranded molecules form dimers held together by complementary sticky ends. To test for this assumption, the chip was maintained with ssDNA at 45° C. (see experimental section for details). The result is shown in FIGS. 39A and 39B.

FIG. 39A shows results for OliGreen-dyed λ-ssDNA, which were prepared in bulk by heating and snap cooling λ-dsDNA, and introduced through the porous roof of the chip, in which the chip was placed on a heated platform to induce melting of dimers (45° C.), and FIG. 39B shows a corresponding histogram illustrating a size distribution of the λ-ssDNA length relative to a number of measured molecules of a given size range. The length maximum of the distribution is now better defined, and falls in 10-14 μm region, much more consistent with a single Lambda molecule. Moreover, at an elevated chip temperature no bright YOYO-1 fluorescence was observed (data not shown) from ssDNA samples, suggesting that short self-complementary duplex DNA regions, where YOYO-1 could intercalate, were disrupted and denatured at higher temperature.

b. Introducing ssDNA into Nanochannels Through the Porous Roof

The unique fabrication process (spin-coating the channels with layers of dispersed silicon oxide nanoparticles and then sintering them at 800° C.), creates a porous roof, with an approximate size of pores about 10 nm (calculated from the nominal nanoparticle diameter of 50 nm). This size is sufficient to allow DNA molecules (~0.2 nm diameter) to migrate into the nanochannels by reptation motion (snake-like movement) driven, most likely, by capillary forces. FIGS. 40A and 41A show the results of this migration for snap-cooled DNA and Lambda Exonuclease-produced ssDNA, respectively.

FIG. 40A shows results for OliGreen-dyed λ-ssDNA, which were prepared in bulk by heating and snap cooling λ-dsDNA, and introduced through the porous roof of the chip and FIG. 40B shows a corresponding histogram illustrating a size distribution of the λ-ssDNA length relative to a number of measured molecules of a given size range. FIG. 40C shows results for OliGreen-dyed λ-ssDNA, which were prepared in bulk by heating and snap cooling λ-dsDNA, and introduced through the porous roof of the heated chip to induce melting of the intramolecular hydrogen bonds and FIG. 39D shows a corresponding histogram illustrating a size distribution of the λ-ssDNA length relative to a number of measured molecules of a given size range.

Unlike the images of long linear molecules in FIG. 38, ssDNA introduced through the roof has more ball-like shape rather than a stretched linear configuration. This is most likely due to the fact that moving through tortuous nanopores, with even more limited space than in nanochannels, short self-complementary regions, inevitably present in DNA of Lambda phage size, come into close proximity and form duplex regions with higher probability. The result is "balled-up" DNA or DNA much shorter visually than the same DNA introduced through the wells (see FIGS. 38A-38D). Raising the ambient temperature or adding a denaturing agent should disrupt these errant hydrogen bonds. Thus, to test the assumption that intra-molecular base-pairing is, in fact, responsible for ssDNA balling up inside the channels after going through tortuous nanopores, this experiment with snap-cooled ssDNA was repeated with the chip maintained at 45° C. (see experimental section and the results shown in FIG. 40C). Heating the chip results in stretching most of the ball-like structures.

FIG. 41A shows results for OliGreen-dyed λ-ssDNA, which were prepared in bulk by pre-digestion with lambda exonuclease, and introduced through the porous roof of the chip and FIG. 41B shows a corresponding histogram illustrating a size distribution of the λ-ssDNA length relative to a number of measured molecules of a given size range. FIG. 41A shows similar results for ssDNA prepared in bulk with Lambda exonuclease and introduced into the nanochannels through the tortuous nanopores in the roof. The corresponding histogram is shown in FIG. 41B.

c. Producing ssDNA In Situ in the Nanochannels by Snap-Cooling

The unique fabrication process (spin-coating the channels with layers of dispersed silicon oxide nanoparticles and then sintering them at 800° C.), creates a porous roof, with an approximate size of pores about 10 nm (calculated from the nominal nanoparticle diameter of 50 nm). This size is sufficient to allow DNA molecules (~0.2 nm diameter) to migrate into the nanochannels by reptation motion (snake-like movement) driven, most likely, by capillary forces. FIGS. 40A and 41A show the results of this migration for snap-cooled DNA and Lambda Exonuclease-produced ssDNA, respectively.

It is interesting to compare ssDNA prepared in bulk and then introduced into nanochannels to ssDNA introduced into the nanochannels as dsDNA and converted in situ into ss form. "Snap-cooling" was mimicked by heating the chip to 95° C. and then cooling it on ice after the introduction of the dsDNA. The extent of the DNA conversion into ss form was confirmed by staining with the ds-specific intercalated dye YOYO-1, with only minimal fluorescence (FIGS. 42A-42C).

Figure 42:
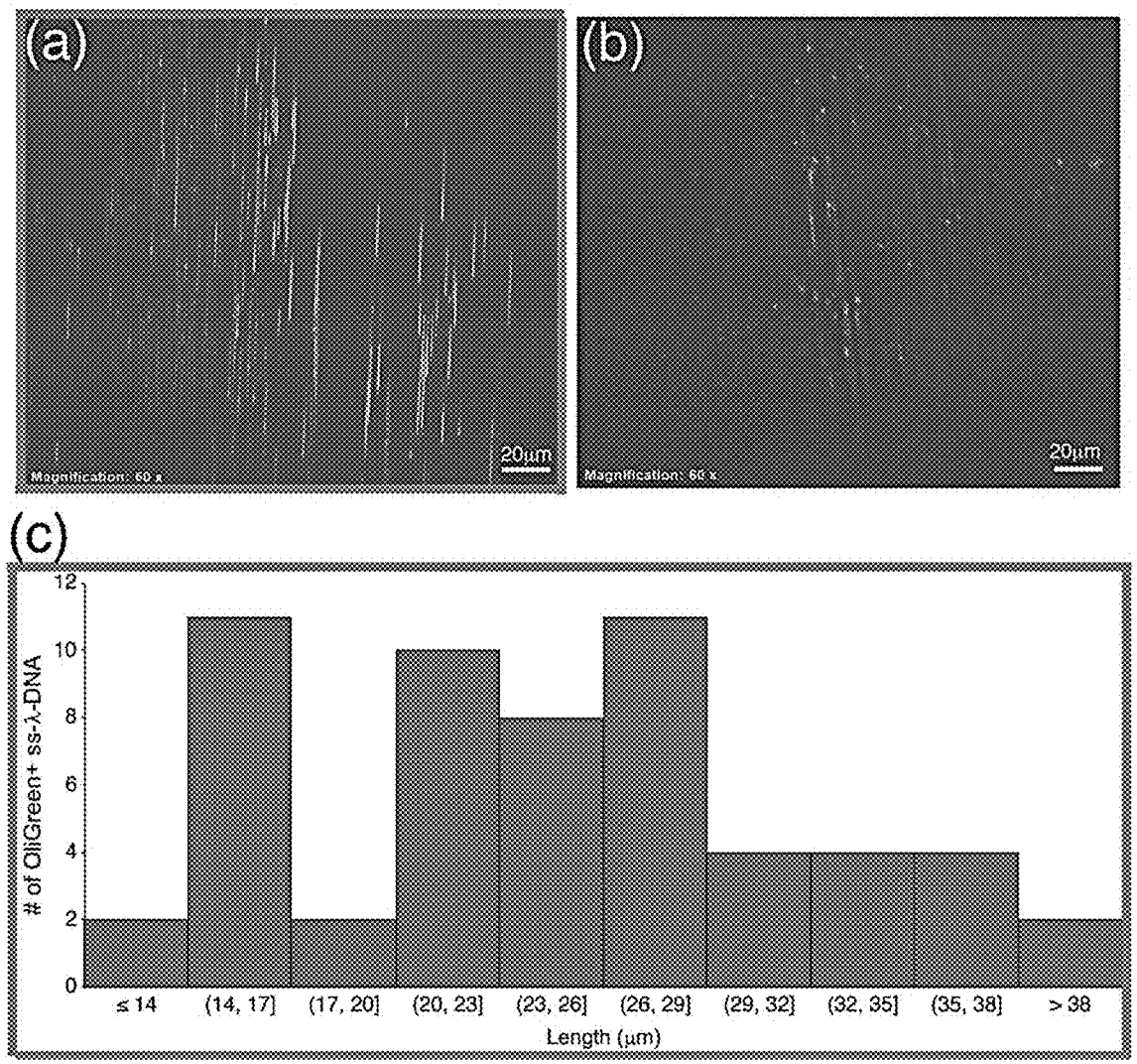
FIG. 42A shows results for OliGreen-dyed λ-ssDNA which were introduced into the nanochannels as λ-dsDNA and converted to λ-ssDNA via heating and snap cooling of the λ-dsDNA in situ.
FIG. 42B shows results for YOYO-1-stained λ-ssDNA which were introduced into the nanochannels as λ-dsDNA and converted to λ-ssDNA via heating and snap cooling of the λ-dsDNA in situ.
FIG. 42C shows a corresponding histogram (of the λ-ssDNA of FIG. 41A) illustrating a size distribution of the λ-ssDNA length relative to a number of measured molecules of a given size range.

FIG. 42A shows results for OliGreen-dyed λ-ssDNA which were introduced into the nanochannels as λ-dsDNA and converted to λ-ssDNA via heating and snap cooling of the λ-dsDNA in situ. FIG. 42B shows results for YOYO-1-stained λ-ssDNA which were introduced into the nanochannels as λ-dsDNA and converted to λ-ssDNA via heating and snap cooling of the λ-dsDNA in situ. FIG. 42C shows a corresponding histogram (of the λ-ssDNA of FIG. 42A) illustrating a size distribution of the λ-ssDNA length relative to a number of measured molecules of a given size range. Unlike snap-cooled ssDNA introduced through the roof, ssDNA molecules produced in situ are fully stretched. The reason is, most likely, the fact that the "parent" dsDNA molecules were already stretched in the nanochannels before denaturation. Confinement in the limited nanochannel space should significantly slow down or completely preclude folding back into a "coil" with the formation of hydrogen bonds in self-complementary regions. However, end-to-end dimer formation in this case is not precluded; in addition, stretched ss DNA molecules confined in the limited nanochannel space may form dimers, or even multimers with their partially complementary regions, resulting in two side-by-side ssDNA molecules. This would also explain why some molecules look brighter than others (two ssDNA side-by-side in the same channel, held together by short base-paired regions that give rise to the YOYO fluorescence in FIG. 42B), and why, while the main "single molecule" distribution peak is around 14-17 μm, similar to the ss DNA introduced through the wells of the heated chip (FIGS. 39A and 39B), there is a significant population of molecules spanning the 20-30 μm length.

d. Producing ssDNA In Situ in the Nanochannels by Lambda Exonuclease Digestion

Figure 43:
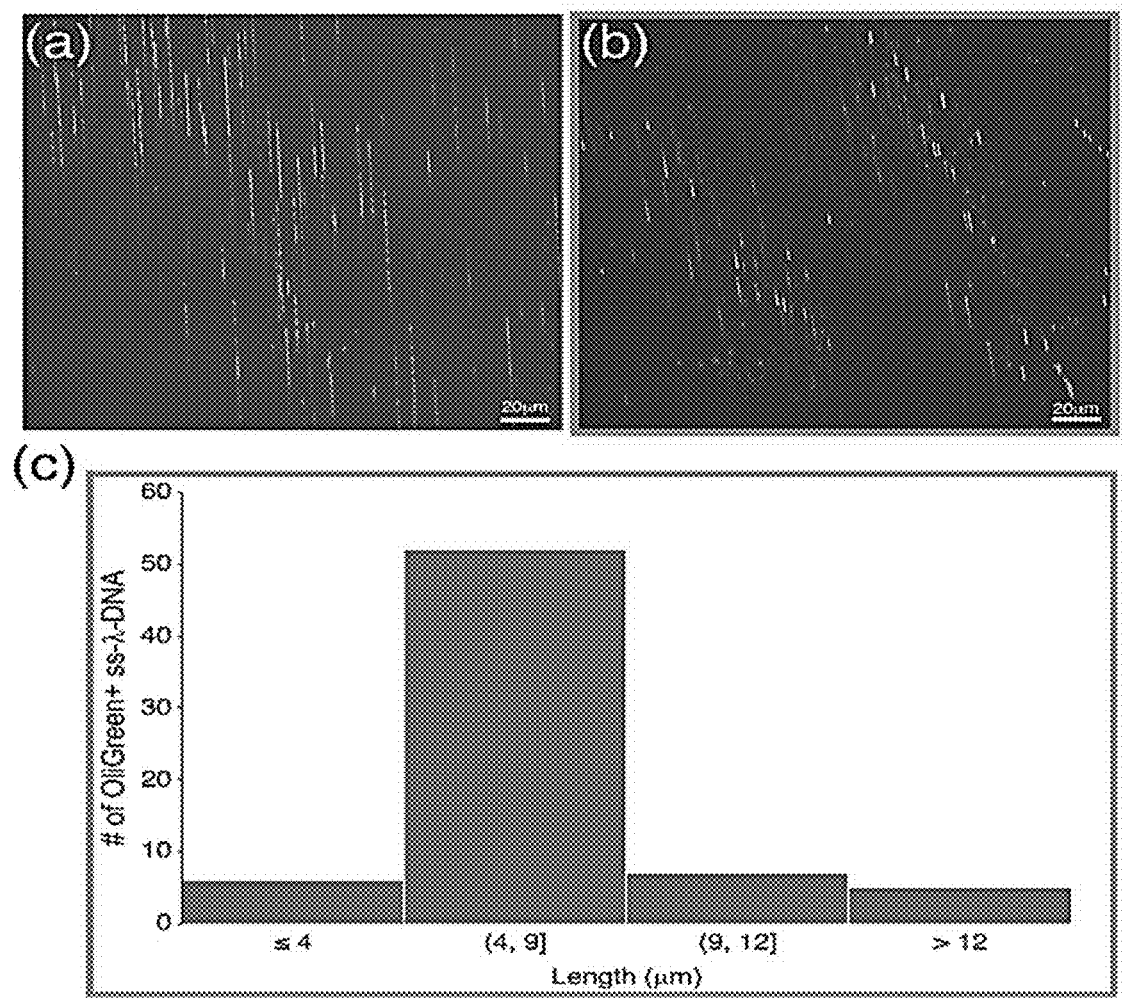
FIG. 43 shows results for in situ generation of λ-ssDNA from λ-dsDNA in the nanochannels via addition of lambda exonuclease through a porous roof, including FIG. 43A which shows results for YOYO-1-stained λ-dsDNA in the nanochannels prior to introduction of the lambda exonuclease.

The unique porous roof also allows introducing various agents to DNA after it enters the nanochannels. FIG. 43 shows results for in situ generation of λ-ssDNA from λ-dsDNA in the nanochannels via addition of lambda exonuclease through a porous roof, including FIG. 43A which shows results for YOYO-1-stained λ-dsDNA in the nanochannels prior to introduction of the lambda exonuclease, FIG. 43B shows OliGreen-dyed λ-ssDNA generated from lambda exonuclease digestion of the λ-dsDNA in situ, and FIG. 43C introduced through the porous roof of the chip, and FIG. 43C shows a corresponding histogram (of the λ-ssDNA of FIG. 42B) illustrating a size distribution of the λ-ssDNA length relative to a number of measured molecules of a given size range. Again, the result is fully stretched ssDNA (FIG. 43B), approximately one half the length of the dsDNA.

Discussion

Long single-stranded DNA molecules are ideal for long-read single-molecule sequencing, and many other analytical and diagnostic applications. Many computational and modeling efforts have been made to determine ssDNA polymer properties. The results presented herein, while mostly empirical, are nevertheless important for understanding and manipulating the behavior of the long ssDNA molecules in confined spaces.

The results show that ssDNA spontaneously enters the nanochannels and that this process does not require any additional pressure or electric field and is driven entirely by capillary forces. However, the shape of ssDNA in nanochannels is to a large extent determined by the method of its introduction. ssDNA efficiently stretches and unfolds when introduced through the wells. This unfolding happens within the few minutes that are needed to mount the slide under the microscope and without any special effort—somewhat contrary to previous observations where a polypeptide copolymer coating was needed to induce the unfolding. The explanation probably lies in the very low ionic strength used in our experiments and therefore to the double layer potential extending across the nanochannels.

Figure 39:
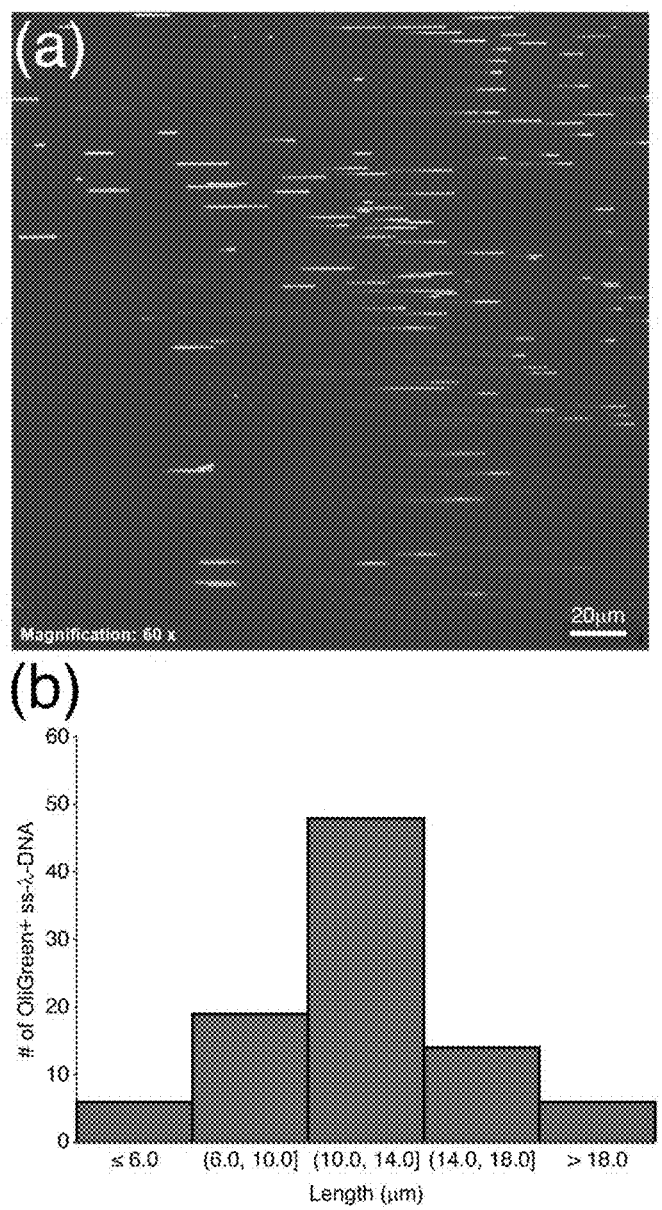
FIG. 39A shows results for OliGreen-dyed λ-ssDNA, which were prepared in bulk by heating and snap cooling λ-dsDNA, and introduced through the porous roof of the chip
FIG. 39B shows a corresponding histogram illustrating a size distribution of the λ-ssDNA length relative to a number of measured molecules of a given size range.

The "sticky" complementary 5' overhangs of λ-dsDNA result in a tendency to form end-to-end dimer molecules, both for ds and full-size ssDNA. Heating the chip slightly or adding the denaturing agent, formamide, at a moderate concentration to the DNA solution results in denaturing these short (12 nucleotide long) regions, while keeping the main duplex intact (the ends should melt at ~28° C. at the ionic conditions used, while the long λ-dsDNA should be stable up to ~60° C. Ten percent formamide reduces the DNA melting temperature by ~6° C., so that the dimers fall apart at room temperature. The length distribution maximum of dsDNA falls into 9-19 μm range with 10% formamide, down from 12-40 without it (see FIG. 36C). Similarly, when the chip with snap-cooled, presumably full-size, ssDNA is maintained at elevated temperature, the length distribution maximum is decreased from 17- to 23 μm at room temperature region down to 10- to 14-μm at 45° C. (FIGS. 39A and 39B). Elevated temperature produced no effect on the average length of the exonuclease-generated ssDNA (data not shown)—and the absence of a temperature effect is consistent with the elimination, by exonuclease digestion, of the 5' protruding sticky ends. When introduced through the wells at the side of the chip, the length of the snap-cooled full-size λ-ssDNA and exonuclease-generated, (roughly half-length) ssDNA (FIGS. 38 and 39) correlate reasonably well (10- to 14 µm for snap-cooled (with the dimers eliminated by heating the chip) and 2- to 8 µm for Exonuclease-generated).

Figure 40:
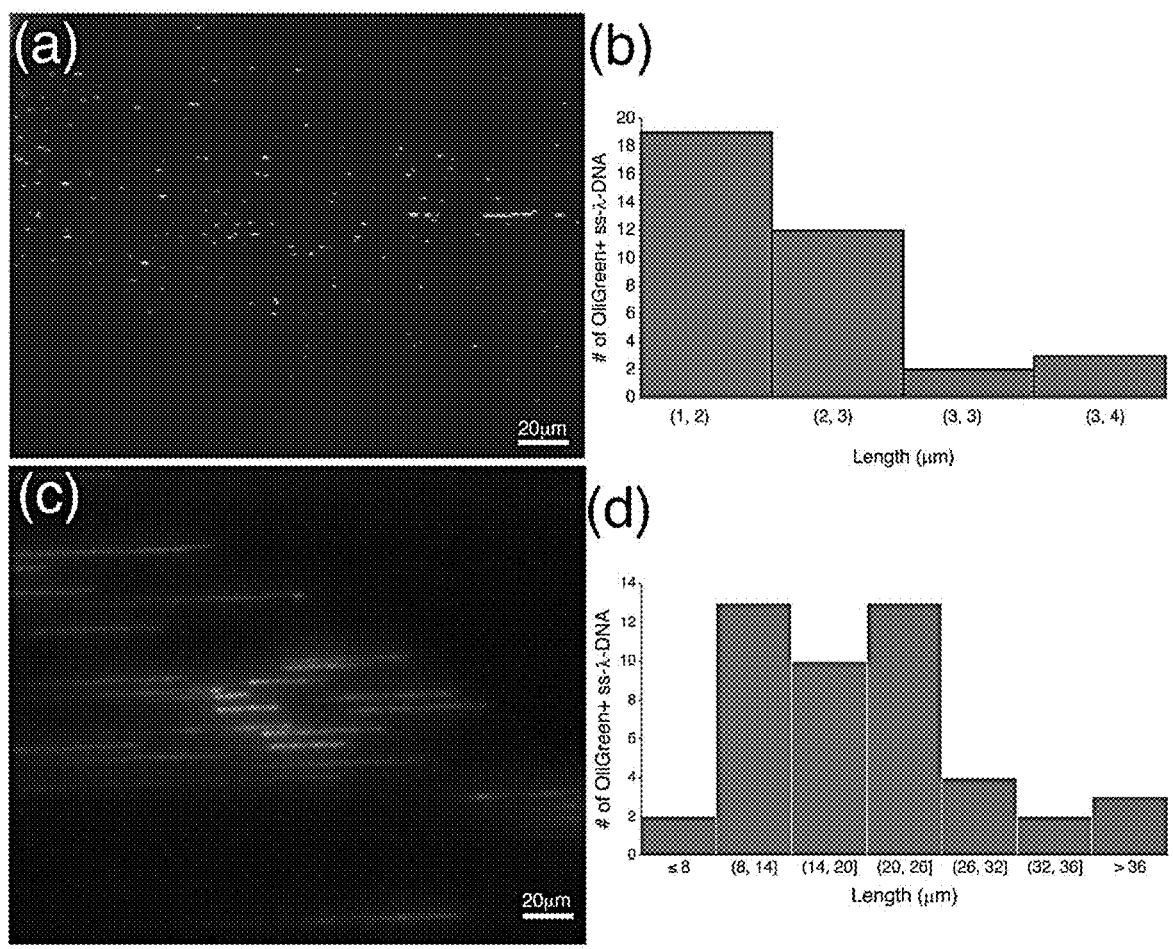
FIG. 40A shows results for OliGreen-dyed λ-ssDNA, which were prepared in bulk by heating and snap cooling λ-dsDNA, and introduced through the porous roof of the chip
FIG. 40B shows a corresponding histogram illustrating a size distribution of the λ-ssDNA length relative to a number of measured molecules of a given size range.
FIG. 40C shows results for OliGreen-dyed λ-ssDNA, which were prepared in bulk by heating and snap cooling λ-dsDNA, and introduced through the porous roof of the heated chip to induce melting of the intramolecular hydrogen bonds
FIG. 40D shows a corresponding histogram illustrating a size distribution of the λ-ssDNA length relative to a number of measured molecules of a given size range.
Figure 41:
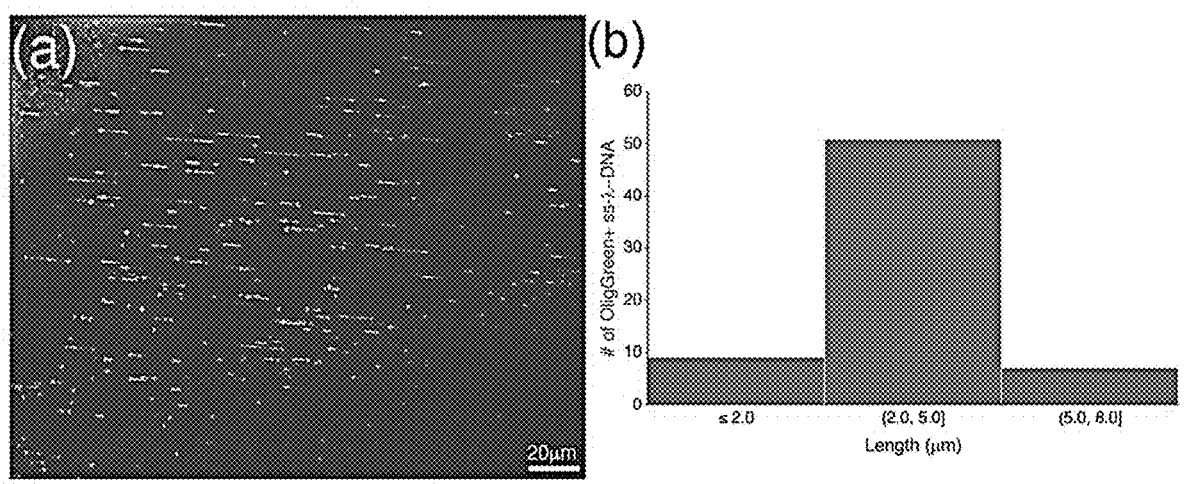
FIG. 41A shows results for OliGreen-dyed λ-ssDNA, which were prepared in bulk by pre-digestion with lambda exonuclease, and introduced through the porous roof of the chip
FIG. 41B shows a corresponding histogram illustrating a size distribution of the λ-ssDNA length relative to a number of measured molecules of a given size range.

Another important result is the ability to introduce DNA and other agents through the roof, albeit with a change in the length distribution (FIGS. 40 and 41). In the case of introduction through the roof, for highly flexible ssDNA in a highly confined nanopore space, it should be, actually, thermodynamically favorable to adopt a compact shape, with as many intra-strand base pairs as possible, even at low ionic strength. These balled up molecules have an average length of less than 5 µm, both for snap-cooled full-length ssDNA, and Exonuclease-produced shortened ssDNA. Most likely the balled-up shape is stabilized by inter- and intra-molecular hydrogen bonds formed in the tight confinement of the tortuous nanopores. Such hydrogen bonds should be disrupted by elevated temperature, and this is exactly what happens when the chip is heated to 45° C. (FIG. 39C). These hydrogen bonds dissociate very rapidly at elevated temperature resulting in the stretching of the molecules. However, there is a sizeable population of long molecules in FIGS. 40C and 40D. Two possible interpretations for this observation are that some remaining inter-molecular hydrogen bonds hold two full-size molecules together, or increased stretching of ssDNA at elevated temperature. This requires further investigation.

Similar persistence of dimer-sized molecules, in addition to the single molecules in the 14-19 µm length range, is evident for the snap-cooled DNA prepared in situ (FIGS. 42A-42C). In the case of in situ conversion, the "starting point" is dsDNA, which, because of its much higher rigidity and lower flexibility quickly stretches and linearizes inside the nanochannels. Hence, further manipulations (snap-cooling or exonuclease digestion) happen on already stretched molecules, and this conformation is thermodynamically favorable because of the minimized electrostatic interactions with the nanochannel walls, so it is a long-lived one. However, the physical proximity of the denatured, but still complementary ssDNA halves of the original ds duplex may result in partially paired dimer-sized ssDNA molecules seen in FIGS. 42A-42C. The effect of elevated temperature and denaturing agents on the length distribution will be investigated separately.

In contrast, conversion of dsDNA into ssDNA by exonuclease added to the nanochannels through the roof nanopores (FIGS. 41A and 41B) gives a narrow size distribution of the resulting ssDNA molecules. In this case, there are no sticky ends (these are removed by the exonuclease) and a much lower potential for inter-molecular hydrogen bonds since, again, the remaining ssDNA fragments of the original ds λ-DNA are non-complementary (see the schematic drawing in FIG. 37). The length peaks between 4 and 9 µm and reflects the population of approximately half-size molecules in various degrees of stretching.

Overall, results obtained with in situ and ex situ preparation of ssDNA correlate well for both snap-cooling and exonuclease digestion. The ability to add enzymes or other DNA-manipulating or DNA-binding agents to already stretched ssDNA molecules in the nanochannels opens up the possibility of many innovative diagnostic applications.

What is claimed is:

1. A method for sequencing nucleic acids, comprising:
   introducing a buffer solution comprising long-chain nucleic acids to a nanochannel chip, the nanochannel chip comprising:
   at least one nanochannel formed in an upper surface of the nanochannel chip and configured to receive the buffer solution, the at least one nanochannel having a passivation agent coating uniformly provided thereon, the passivation agent coating being configured to provide uniform nucleic acid propagation through the at least one nanochannel by reducing trapping interactions between long-chain nucleic acids and walls of the nanochannels as result of inhomogeneities in the formation of the at least one nanochannel;
   a roof covering the nanochannel and comprising nanopores;
   an electromagnetic-field enhancement structure configured to spatially localize incident electromagnetic fields to a spatial scale of about 1 nm$^3$; and
   a barrier disposed in the nanochannel;
   applying a voltage potential across the nanochannel chip to drive the nucleic acids through the nanochannel in a first direction, towards the barrier, and to translocate the nucleic acids through nanopores adjacent to the barrier, such that bases of each of the nucleic acids pass through the electromagnetic-field enhancement structure one base at a time and emerge onto an upper surface of the roof;
   detecting the Raman spectra of the bases of the nucleic acids as each base passes through the electromagnetic-field enhancement structure; and
   identifying the sequence of bases in the nucleic acids based on the detected Raman spectra.

2. The method of claim 1, wherein the electromagnetic-field enhancement structure is configured to spatially localize incident electromagnetic fields to a spatial scale of about 1 nm$^3$ in combination with the nanopores.

3. The method of claim 1, wherein the detecting the Raman spectra comprises:
   illuminating a rectangular region of the roof with the long dimension of the rectangle perpendicular to the nanochannel direction, and the short dimension of the rectangle in the vicinity of a nanochannel barrier where the ssDNA is forced to transit the roof;
   focusing light inelastically scattered from moieties in the rectangular region onto an input slit of a spectrometer;
   generating image data by recording Raman spectral data output from an outlet of the spectrometer using a camera; and
   providing the image data to a processor configured to sequence the nucleic acids based on the image data.

4. The method of claim 3, wherein the illuminating a rectangular region of the nanochannel chip comprises focusing at least one laser beam onto the nanochannel chip.

5. The method of claim 4, wherein the laser beam passes through a lower surface of the nanochannel chip before illuminating the rectangular region of the roof.

6. The method of claim 3, wherein:
   the illuminating a rectangular region of the roof comprises illuminating multiple rectangular regions of the roof; and
   the focusing comprises focusing light from the rectangular regions onto corresponding input slits of the spectrometer.

7. The method of claim 1, wherein the nanochannel is coated with the passivation agent prior to introducing the buffer solution.

8. The method of claim 7, wherein the passivation agent comprises a lipid bilayer.

9. The method of claim 7, wherein the passivation agent comprises bovine serum albumin.

10. The method of claim 1, wherein the nucleic acids comprise single-stranded deoxyribonucleic acids (ssDNA).

11. The method of claim 10, wherein the ssDNA is added to the buffer solution before the introduction of the buffer solution to the nanochannel chip.

12. The method of claim 10, wherein the ssDNA is formed after the buffer solution is introduced to the nanochannel chip by digesting double-stranded DNA using an exonuclease.

13. The method of claim 1, wherein the ssDNA is formed after the buffer solution is introduced to the nanochannel chip by heating and snap cooling double-stranded DNA.

14. The method of claim 1, wherein the applying the voltage potential comprises applying a constant direct current component and applying a time varying current component comprising a pulsed or alternating current.

15. The method of claim 14, wherein the applying the voltage potential comprises periodically reversing the polarity of the applied voltage potential to drive the nucleic acids in an opposing direction.

16. The method of claim 15, wherein the detecting the Raman spectra comprises detecting the Raman spectra as the nucleic acids move in the second direction and the bases pass through the electromagnetic-field enhancement structure multiple times, in order to provide detection redundancy and increase sequencing accuracy.

17. The method of claim 1, wherein the sequencing comprises distinguishing between cytosine (C) and 5-methyl-cytosine (5mC) bases using the detected Raman spectra.

18. The method of claim 1, wherein the sequencing comprises distinguishing between adenine (a) and 5-methyl-adenine (5 mA) bases using the detected Raman spectra.

19. The method of claim 1, wherein:
the detecting the Raman spectra comprises detecting a Raman spectra ranging from a wavenumber of about 500 $cm^{-1}$ to a wavenumber of about 1700 $cm^{-1}$; and
the sequencing the nucleic acids comprises analysis of the spectra by statistical procedures.

20. The method of claim 1, wherein:
the nucleic acids comprise single-stranded deoxyribonucleic acids (ssDNA) bonded to tethering moieties; and
the tethering moieties are configured to prevent the complete translocation of the ssDNA through the nanopores, during the applying a voltage potential across the nanochannel chip.

21. The method of claim 20, wherein the tethering moieties comprise quantum dots, metal nanoparticles, fullerene molecules, or any combinations thereof.

22. The method of claim 1, wherein the electromagnetic-field enhancement structure comprises a metal-insulator-metal (MIM) layer.

23. The method of claim 22, wherein the detecting the Raman spectra further comprises detecting a combination of pump, Stokes, and anti-Stokes wavelengths interacting resonantly with individual bases.

24. The method of claim 1, wherein the electromagnetic-field enhancement structure comprises a structured metal film.

25. The method of claim 24, wherein the electromagnetic-field enhancement structure comprises a metal-insulator-metal (MIM) film comprising holes that are self-aligned to pores in the roof of the nanochannels.

26. The method of claim 24, wherein the electromagnetic-field enhancement structure comprises a metal film comprising holes that are self-aligned to pores in the roof of the nanochannels.

27. The method of claim 24, wherein the electromagnetic-field enhancement structure comprises an array of metal-insulator-metal (MIM) structures with at least one structural resonance tuned to the vicinity of one of the laser fields used for the Raman measurement.

28. The method of claim 24, wherein the electromagnetic-field enhancement structure comprises an array of metal structures with individual structural resonances of the array elements tuned to the vicinity of one of the laser fields used for the Raman measurement.

* * * * *